US009175269B2

(12) United States Patent
Wakita et al.

(10) Patent No.: US 9,175,269 B2
(45) Date of Patent: Nov. 3, 2015

(54) MODIFIED HUMAN HEPATITIS C VIRUS GENOMIC RNA THAT CAN BE AUTONOMOUSLY REPLICATED

(71) Applicants: TOKYO METROPOLITAN INSTITUTE OF MEDICAL SCIENCE, Tokyo (JP); TORAY INDUSTRIES, INC., Tokyo (JP)

(72) Inventors: Takaji Wakita, Tokyo (JP); Takanobu Kato, Aichi (JP); Tomoko Date, Kanagawa (JP); Michiko Miyamoto, Tokyo (JP); Ralf Bartenschlager, Schriesheim (DE); Jun-ichi Tanabe, Kanagawa (JP); Saburo Sone, Kanagawa (JP)

(73) Assignees: TORAY INDUSTRIES, INC., Tokyo (JP); TOKYO METROPOLITAN INSTITUTE OF MEDICAL SCIENCE, Tokyo (JP)

( * ) Notice: Subject to any disclaimer, the term of this patent is extended or adjusted under 35 U.S.C. 154(b) by 163 days.

(21) Appl. No.: 13/734,630

(22) Filed: Jan. 4, 2013

(65) Prior Publication Data

US 2013/0115592 A1    May 9, 2013

Related U.S. Application Data

(62) Division of application No. 11/660,794, filed as application No. PCT/JP2005/015833 on Aug. 24, 2005, now Pat. No. 8,454,973.

(30) Foreign Application Priority Data

| Aug. 24, 2004 | (JP) | 2004-243975 |
| Oct. 1, 2004 | (JP) | 2004-290801 |
| Mar. 11, 2005 | (JP) | 2005-069527 |
| Mar. 11, 2005 | (JP) | 2005-069725 |

(51) Int. Cl.
| A61K 39/29 | (2006.01) |
| C12N 7/02 | (2006.01) |
| C12N 7/00 | (2006.01) |
| C12N 15/86 | (2006.01) |
| C12Q 1/68 | (2006.01) |
| A61K 48/00 | (2006.01) |
| A61K 39/00 | (2006.01) |

(52) U.S. Cl.
CPC *C12N 7/00* (2013.01); *C12N 15/86* (2013.01); *C12Q 1/6883* (2013.01); *A61K 48/00* (2013.01); *A61K 2039/525* (2013.01); *C12N 2770/24221* (2013.01); *C12N 2770/24243* (2013.01); *C12N 2840/203* (2013.01)

(58) Field of Classification Search
None
See application file for complete search history.

(56) References Cited

U.S. PATENT DOCUMENTS

| 6,387,662 | B1 | 5/2002 | Liang et al. | |
| 8,604,179 | B2 * | 12/2013 | Akazawa et al. | 536/23.72 |
| 2005/0250093 | A1 | 11/2005 | Gates et al. | |
| 2006/0210969 | A1 | 9/2006 | Rice et al. | |
| 2008/0032323 | A1 | 2/2008 | Wakita et al. | |
| 2008/0311158 | A1 | 12/2008 | Merola | |

FOREIGN PATENT DOCUMENTS

| CA | 2 603 711 C | 6/2013 |
| JP | 2001-504337 A | 4/2001 |
| JP | 2002-171978 A | 6/2002 |
| WO | WO 98/21338 A1 | 5/1998 |
| WO | WO 00/75338 A2 | 12/2000 |
| WO | WO 01/47551 A2 | 7/2001 |
| WO | WO 02/08292 A2 | 1/2002 |
| WO | WO 03/085084 A2 | 10/2003 |
| WO | WO 2004/104198 A1 | 12/2004 |
| WO | WO 2006/096459 A2 | 9/2006 |

OTHER PUBLICATIONS

Canadian Office Action, dated Jun. 20, 2013, for Patent Application No. 2,578,021.
11th International Symposium on Hepatitis C Virus and Related Viruses, Heidelberg, Oct. 3-7, 2004.
Advisory Action dated Sep. 23, 2011, for U.S. Appl. No. 11/660,794, pp. 1-3.
Advisory Action dated Sep. 28, 2010, for U.S. Appl. No. 11/660,794, pp. 1-3.
Applicant-Initiated Interview Summary dated Apr. 9, 2012, for U.S. Appl. No. 11/660,794, pp. 1-3.
Bartenschlager, "Hepatitis C virus molecular clones: from cDNA to infectious virus particles in cell culture", Current Opinion in Microbiology, vol. 9, No. 4, pp. 416-422 (Aug. 2006).
Bartosch et al., "In vitro assay for neutralizing antibody to hepatitis C virus: evidence for broadly conserved neutralization epitopes," Proceedings of the National Academy of Sciences of the United States of America, vol. 100 No. 24, pp. 14199-14204 (Epub Nov. 2003).

(Continued)

*Primary Examiner* — Stacy B Chen
(74) *Attorney, Agent, or Firm* — Birch, Stewart, Kolasch & Birch, LLP

(57) ABSTRACT

The present invention provides modified hepatitis C virus genomic RNA, comprising nucleotide sequences of genomic RNA portions of two or more types of hepatitis C viruses, which comprises a 5' untranslated region, a core protein coding sequence, an E1 protein coding sequence, a p7 protein coding sequence, an E2 protein coding sequence, an NS2 protein coding sequence, an NS3 protein coding sequence, an NS4A protein coding sequence, an NS4B protein coding sequence, an NS5A protein coding sequence, an NS5B protein coding sequence, and a 3' untranslated region, and which can be autonomously replicated. In particular, the present invention relates to modified hepatitis C virus genomic RNA, which can be autonomously replicated by substitution of the RNA sequence portion encoding NS3, NS4, NS5A, and NS5B proteins of hepatitis C virus genomic RNA with a partial RNA sequence encoding NS3, NS4, NS5A, and NS5B proteins of a JFH1 strain shown in SEQ ID NO: 1.

12 Claims, 16 Drawing Sheets
(5 of 16 Drawing Sheet(s) Filed in Color)

(56) References Cited

OTHER PUBLICATIONS

Corrected Notice of Allowance with Examiner's Interview Summary and Supplemental Examiner's Amendment dated Jan. 3, 2013, for U.S. Appl. No. 11/660,794, pp. 1-8.
Date T. et al., J. Biol. Chem., May 21, 2004, vol. 279, No. 21, p. 22371-22376.
Duverlie et al., "Cell culture systems for the hepatitis C virus", World Journal of Gastroenterology, vol. 13, No. 17, pp. 2442-2445 (May 2007).
English translation of International Report on Patentability dated Mar. 8, 2007.
Final Office Action dated Jun. 16, 2011, for U.S. Appl. No. 11/660,794, pp. 1-13.
Final Office Action dated May 11, 2012, for U.S. Appl. No. 11/660,794, pp. 1-11.
Final Office Action dated May 14, 2010, for U.S. Appl. No. 11/660,794, pp. 1-10.
Gates AT et al., Virus Res, Mar. 2004, vol. 100, No. 2, p. 213-222.
International Search Report mailed Nov. 22, 2005, for International Patent Application No. PCT/JP2005/015833.
Kato et al., Gastroenterology, vol. 125, 2003, XP005313661, pp. 1808-1817.
Kato et al., Journal of Medical Virology, vol. 64, 2001, XP002986251, pp. 334-339.
Keck et al., Journal of Virology, vol. 78, No. 13, Jul. 2004, XP002413541, pp. 7257-7263.
Lindenbach BD. et al., Science, Jul. 25, 2005, vol. 309, No. 5734. pp. 623-626.
Ma Yuanyuan et al., J. Biol. Chem., Jun. 11, 2004, vol. 279, No. 24, pp. 25474-25482.
Miscellaneous Communication-No Action Count dated Oct. 25, 2012, for U.S. Appl. No. 11/660,794, pp. 1-2.
Moradpour et al., "Tightly Regulated Expression of the Entire Hepatitis C Virus Structural Region in Continuous Human Cell Lines," Biochemical and Biophysical Research Communications, vol. 246 No. 3, pp. 920-924 (May 1998).
Non-Final Office Action dated Feb. 15, 2011, for U.S. Appl. No. 11/660,794, pp. 1-11.
Non-Final Office Action dated Jan. 17, 2012, for U.S. Appl. No. 11/660,794, pp. 1-6.
Non-Final Office Action dated Jan. 29, 2010, for U.S. Appl. No. 11/660,794, pp. 1-20.
Notice of Allowance with Examiner's Interview Summary and Examiner's Amendment dated Oct. 2, 2012, for U.S. Appl. No. 11/660,794, pp. 1-9.
Notice of Panel Decision from Pre-Appeal Brief Review dated Sep. 17, 2012, for U.S. Appl. No. 11/660,794, pp. 1-2.
Paredes et al., "A Genetic Interaction between Hepatitis C Virus NS4B and NS3 is Important for RNA Replication", Journal of Virology, vol. 82, No. 21, pp. 10671-10683 (Nov. 2008).
Pietschmann et al., Journal of Virology, vol. 76, No. 8, Apr. 2002, XP002377301, pp. 4008-4021.
Restriction Requirement dated Oct. 14, 2009, for U.S. Appl. No. 11/660,794, pp. 1-9.
Supplementary European Search Report dated Oct. 25, 2007, for EP Application No. 05 78 1421.
Wakita T. et al., Nat. Med., Jul. 2005, vol. 11, No. 7, pp. 1-6.
Yanagi et al., Hepatitis C Virus: An Infectious Molecular Clone of a Second Major Genotype (2a) and Lack of Viability of Intertypic 1a and 2a Chimeras, Virology, vol. 262 No. 1, pp. 250-263 (Sep. 1999).
Canadian Office Action, Issued in Canadian Application No. 2,578,021 on Jan. 11, 2013, 2 pages.

\* cited by examiner

Fig. 6
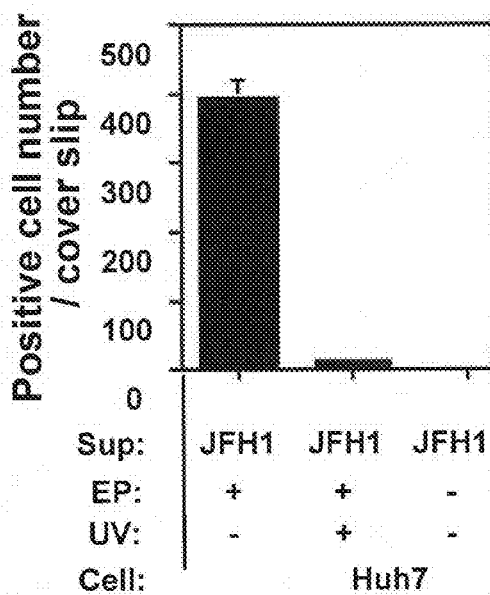
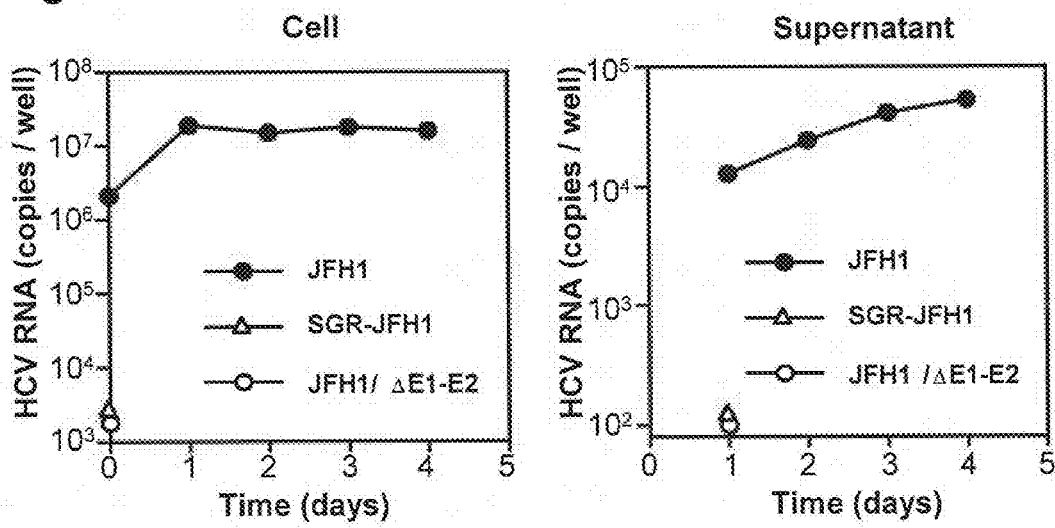

Fig. 9 rFGREP-TH/JFH1
1µg RNA transfection

Fig. 12
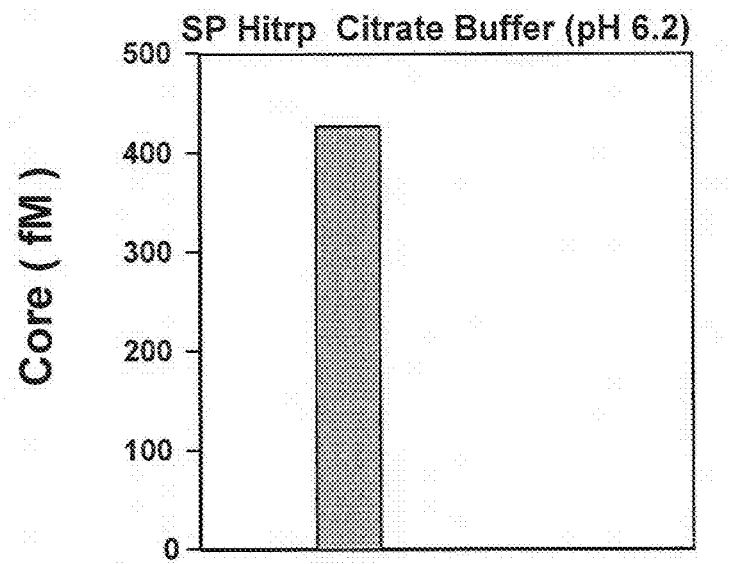
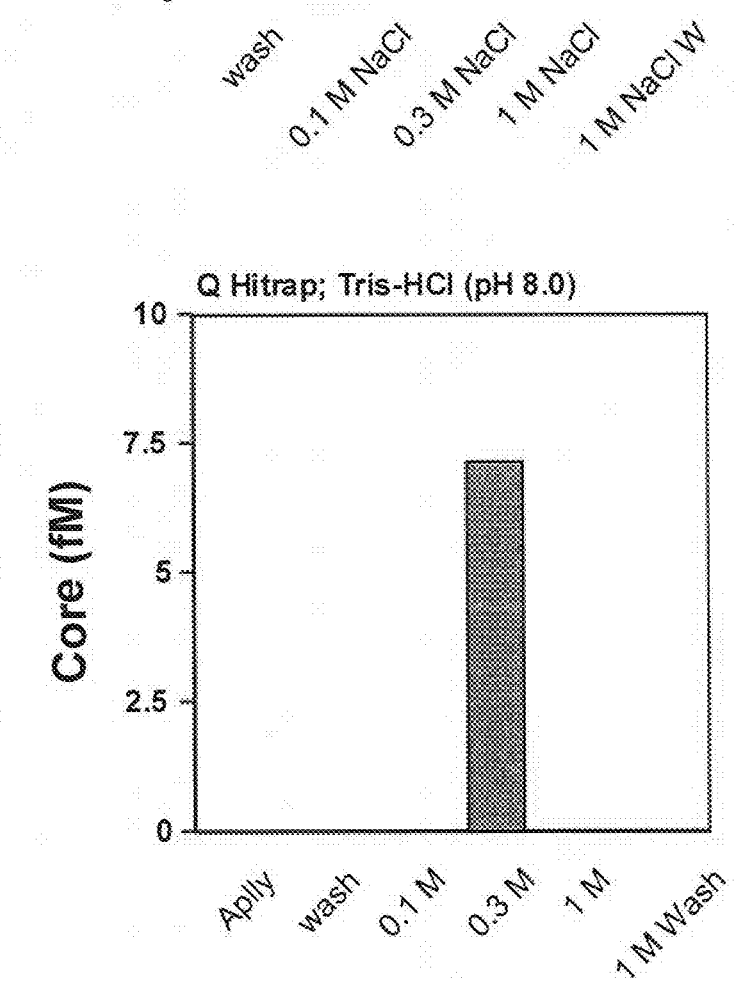

Fig. 14
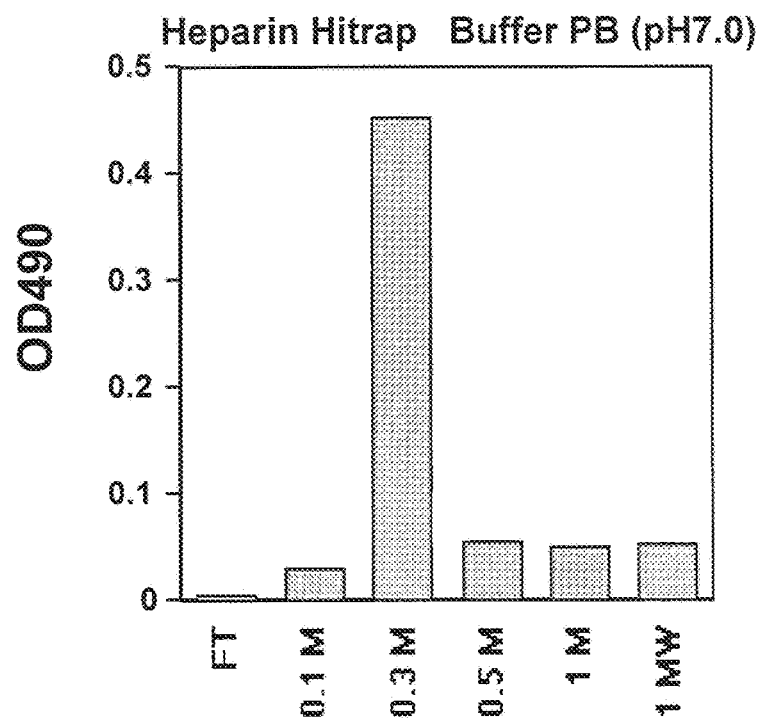
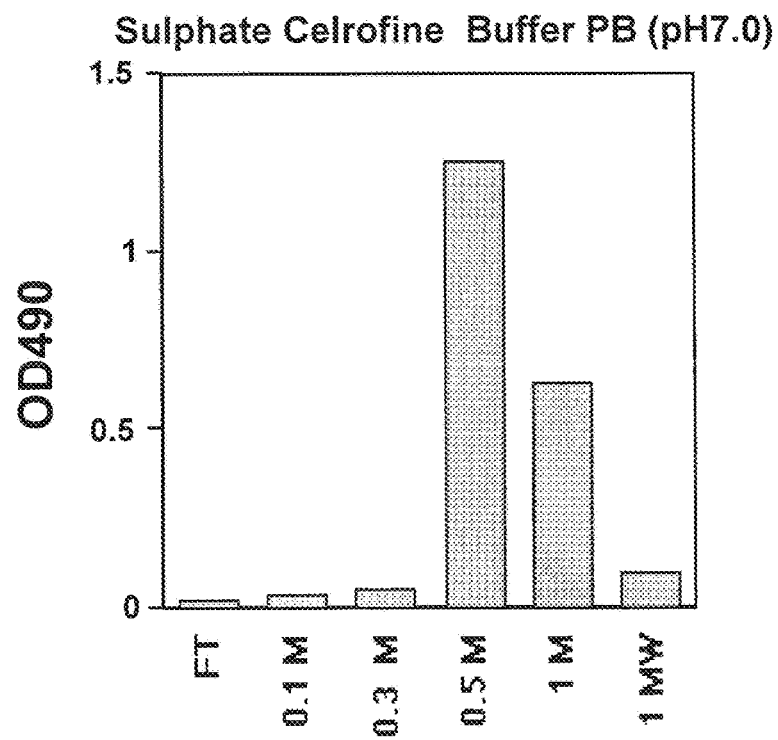

Fig. 16
A
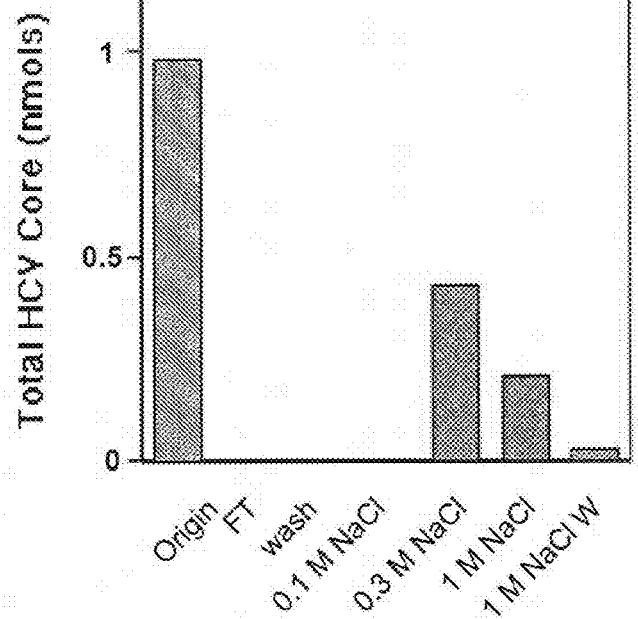
B
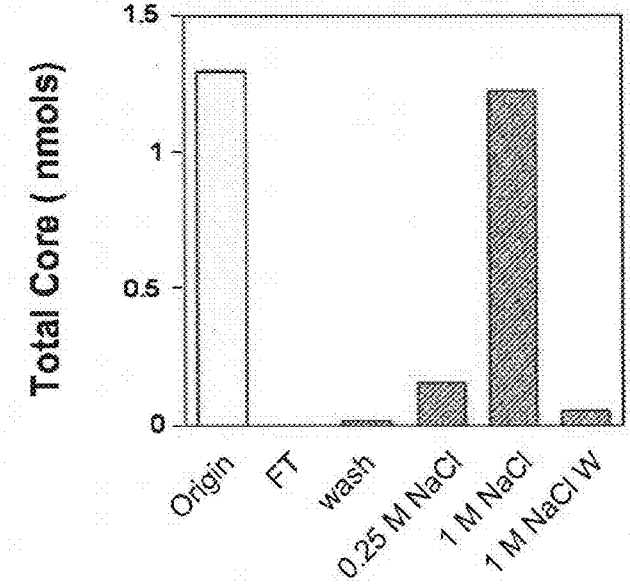

MODIFIED HUMAN HEPATITIS C VIRUS GENOMIC RNA THAT CAN BE AUTONOMOUSLY REPLICATED

CROSS REFERENCE TO RELATED APPLICATIONS

This application is a Divisional of co-pending application Ser. No. 11/660,794 filed on Feb. 22, 2007, which is the national phase of PCT International Application No. PCT/JP2005/015833 filed on Aug. 24, 2005, and which claims the benefit of priority of Japanese Application No. 2004-243975 filed on Aug. 24, 2004; Japanese Application No. 2004-290801 filed on Oct. 1, 2004; Japanese Application No. 2005-069725 filed on Mar. 11, 2005; and Japanese Application No. 2005-069527 filed on Mar. 11, 2005. The entire contents of all of the above applications are hereby incorporated by reference.

TECHNICAL FIELD

The present invention relates to: a method for autonomously replicating human hepatitis C viruses (HCV) with various genotypes in a cultured cell system; modified HCV genomic RNA used therefor; and a cell that replicates the above-described HCV genomic RNA.

BACKGROUND ART

As a result of the recent studies, it has been clarified that hepatitis C virus is classified into a large number of types, depending on genotype or serotype. In accordance with the phyloanalysis method of Simmonds et al. using the nucleotide sequences of HCV strains, which is presently being used as a mainline HCV genotype classification method, HCV is classified into the following 6 types: genotype 1a, genotype 1b, genotype 2a, genotype 2b, genotype 3a, and genotype 3b (Non-Patent Document 1). These types are further classified into several subtypes. The nucleotide sequences of the full-length genomes of a plurality of genotypes of HCV have also been determined (Patent Document 1 and Non-Patent Documents 2 to 4).

HCV causes chronic hepatitis as a result of persistent infection. A main cause of chronic hepatitis, which is recognized on a global scale, is persistent HCV infection. As a matter of fact, approximately 50% of persistently infected patients develop chronic hepatitis, and approximately 20% of the patients shift to hepatocirrhosis over 10 to 20 years. Moreover, some patients thereof develop fatal pathologic conditions such as liver cancer.

At present, the main treatments for hepatitis C include the use of interferon-α or interferon-β, and the combined use of interferon-α with ribavirin, which is a purine-nucleoside derivative. However, although these treatments are performed on patients, the therapeutic effects thereof are observed only in approximately 60% of such patients. If the treatments are terminated after such therapeutic effects have been obtained, more than half of the patients develop recurrent disease. It has been known that the therapeutic effects of interferon depend on the genotype of HCV. That is, it is said that the effects of interferon are low on genotype 1b and that the effects thereof are high on genotype 2a (Non-Patent Document 5). Moreover, the substrate specificity of protease of HCV is different depending on genotype. The inhibitory activity of an inhibitor developed using NS3 protease of genotype 1b is 50 times or more inferior to those developed using NS3 proteases of other genotypes (Non-Patent Document 6). Accordingly, in order to develop an HCV therapeutic agent with efficiency, it is required to develop the agent, while confirming the reactivity of each of the genotypes of HCV.

Recently, an HCV subgenomic RNA replicon has been produced as RNA derived from HCV which can be autonomously replicated (Patent Documents 2 and 3 and Non-Patent Documents 7 to 9). Thereby, it became possible to analyze HCV replication mechanisms, using cultured cells. Such an HCV subgenomic RNA replicon is produced by substituting a structural protein existing downstream of HCV IRES, in the 5' untranslated region of HCV genomic RNA, with a neomycin resistance gene and EMCV-IRES that is ligated downstream thereof. This RNA replicon was introduced into human liver cancer cells Huh7, and the cells were then cultured in the presence of neomycin. As a result, it was demonstrated that the RNA replicon autonomously replicates in Huh7 cells. Moreover, it was also demonstrated that several HCV subgenomic RNA replicons autonomously replicate in cells other than Huh7, such as human cervical cancer cells HeLa, or human liver cancer cells HepG2 (Patent Document 3).

However, such HCV intracellular RNA replication systems have been produced for limited genotypes, or rather, such systems have been produced only using genomic RNAs of a limited number of HCV strains. Thus, with regard to HCV having a large number of genotypes, it is extremely difficult to analyze differences in therapeutic effects of the developed HCV therapeutic agents that are caused by differences in the genotypes of the above agents. Such an RNA replicon is an experimental system, which is only useful for evaluating the replication of virus RNA during the growth and replication process of an HCV virus. Hence, it is impossible for such an RNA replicon to evaluate processes, such as formation of HCV virus particles in an infected cell, the release thereof out of the cell, or infection of a new cell.

Currently, application of a method for evaluating such processes as formation of HCV virus particles, the release thereof out of the cell, and infection of a new cell is limited to an experimental system using animals such as chimpanzees (Non-Patent Document 10). However, such an experimental system, in which living animal bodies are directly used, involves complicated operations, and thus it is extremely difficult to conduct analyses with such an experimental system. Accordingly, in order to analyze such processes as formation of HCV virus particles, the release thereof out of the cell, and infection of a new cell, or in order to develop an anti-HCV agent using inhibition of such processes as an action mechanism, it is necessary to construct an extremely simplified experimental system capable of replicating such processes; namely, an HCV virus particle replication system using a cultured cell system.

If it became possible to stably supply HCV virus particles from such a cultured cell system, a virus could be attenuated, or a noninfectious HCV virus could be produced by means based on molecular biology, thereby using such viruses as vaccines. However, since HCV protein sequences differ depending on genotype, the antigenicity of HCV also differs depending on genotype. In fact, the presence of various genotypes constitutes a significant impediment to the production of HCV vaccines (Non-Patent Document 11). Accordingly, in order to efficiently produce HCV vaccines as well, it has been desired that HCV virus particles with various genotypes be stably produced in a cultured cell system.

It has been known that HCV is a spherical particle with a size between 55 and 65 nm, which exists in the blood of a patient infected with HCV. As a method for purifying HCV existing in human serum, affinity chromatography using lectin (Non-Patent Document 12) and chromatography using heparin (Non-Patent Document 13) have been known. However, by these methods, only less than 1 ml of virus can be purified at a concentration of approximately 1 M copies/ml. Thus, these methods are not industrially applicable.

Several methods for purifying virus particles other than HCV have been created to date (Patent Documents 4, 5, and 6, for example). However, as is clear from these publications, virus particles have various properties, and thus the particles give no useful information regarding an optimal method for purifying human hepatitis C virus. Patent Document 7 discloses that human hepatitis A virus, which is also a hepatitis virus, can be purified by eliminating DNA according to anion exchange chromatography. However, although hepatitis A virus is also a hepatitis virus, it is a virus having DNA as a gene. As is clear from the fact that hepatitis C virus has RNA as a gene, there are no relevant similarities between hepatitis A virus and hepatitis C virus, and thus no information is given regarding relevant purification methods. In order to use human hepatitis C virus particles as vaccines or the like in the industrial field in the future, it is required to highly purify such particles in high volume. Under such circumstances, the development of a purification method is anticipated.

[Patent Document 1]
JP Patent Publication (Kokai) No. 2002-171978 A
[Patent Document 2]
JP Patent Publication (Kokai) No. 2001-17187 A
[Patent Document 3]
WO2004/104198A1
[Patent Document 4]
Japanese Patent No. 3313117
[Patent Document 5]
JP Patent Publication (Kohyo) No. 2002-503484 A
[Patent Document 6]
JP Patent Publication (Kohyo) No. 2000-510682 A
[Patent Document 7]
JP Patent Publication (Kokoku) No. 6-48980 B (1994)
[Non-Patent Document 1]
Simmonds P. et al., Hepatology, 10 (1994) pp. 1321-1324
[Non-Patent Document 2]
Choo Q. L. et al., Science, 244 (1989) pp. 359-362
[Non-Patent Document 3]
Okamoto H. et al., J. Gen. Virol., 73 (1992) pp. 673-679
[Non-Patent Document 4]
Mori S. et al., Biochem. Biophis. Res. Commun. 183 (1992) pp. 334-342
[Non-Patent Document 5]
Yoshioka K. et al., Hepatology, 16 (1992) pp. 293-299
[Non-Patent Document 6]
Thibeault D. et al., J. Virol., 78 (2004) pp. 7352-7359
[Non-Patent Document 7]
Blight et al., Science, 290 (2000) pp. 1972-1974
[Non-Patent Document 8]
Friebe et al., J. Virol., 75 (2001) pp. 12047-12057
[Non-Patent Document 9]
Kato T. et al., Gastroenterology, 125 (2003) pp. 1808-1817
[Non-Patent Document 10]
Kolykhalov et al., Science, 277 (1997) pp. 570-574
[Non-Patent Document 11]
Farci P. et al., Semin Liver Dis 20 (2000) pp. 103-126
[Non-Patent Document 12]
Virology, 196 (1993) pp. 354-357
[Non-Patent Document 13]
Journal of General Virology 86 (2005) pp. 677-685

DISCLOSURE OF THE INVENTION

It is an object of the present invention to provide a method for replicating and amplifying hepatitis C viruses with various genotypes in a cultured cell system.

As a result of intensive studies-directed towards achieving the aforementioned object, the present inventors have produced modified hepatitis C virus genomic RNA by combining genomic RNA of an HCV JFH1 strain that can be autonomously replicated with genomic RNA of an HCV strain that cannot be autonomously replicated in vitro. The inventors have found that the thus produced genomic RNA can be autonomously replicated in a cultured cell system. Specifically, regarding the aforementioned invention, the present inventors have found that introduction of a genomic portion ranging from the NS3 protein coding sequence of the JFH1 strain to the 3'-terminus thereof enables modification of HCV genomic RNA that cannot be autonomously replicated in vitro to result in RNA that can be autonomously replicated in a cultured cell system.

That is to say, the present invention relates to modified hepatitis C virus genomic RNA, comprising nucleotide sequences of genomic RNA portions of two or more types of hepatitis C viruses, which comprises a 5' untranslated region, a core protein coding sequence, an E1 protein coding sequence, an E2 protein coding sequence, a p7 protein coding sequence, an NS2 protein coding sequence, coding sequences of NS3, NS4A, NS4B, NS5A, and NS5B proteins of a JFH1 strain, and a 3' untranslated region, and which can be autonomously replicated.

Specifically, in one embodiment, the present invention provides modified hepatitis C virus genomic RNA, which is produced by substituting a hepatitis C virus genomic RNA portion ranging from an NS3 protein coding sequence to an NS5B protein coding sequence, which is a genome sequence at the 3'-terminus, with a partial RNA sequence encoding the NS3, NS4, NS5A, and NS5B proteins of a JFH1 strain shown in SEQ ID NO: 1 (RNA sequence obtained by substituting T with U in a sequence corresponding to 3867-9678 of the DNA sequence deposited under Genbank Accession No. AB047639), and which can be autonomously replicated.

In another embodiment, the present invention provides modified hepatitis C virus genomic RNA, which is produced by substituting the NS5B protein coding sequence of hepatitis C virus genomic RNA with the NS5B protein coding sequence of a JFH1 strain shown in SEQ ID NO: 2, and which can be autonomously replicated.

Preferred examples of the two or more types of hepatitis C viruses used herein may include a hepatitis C virus with genotype 1b and a hepatitis C virus with genotype 2a. Examples of the virus strain with genotype 1b may include an HCV-con1 strain, an HCV-TH strain, an HCV-J strain, an HCV-JT strain, and an HCV-BK strain. Examples of the virus strain with genotype 2a may include an HCV-J6 strain, an HCV-JFH1 strain, and HCV-JCH1 strain.

The modified hepatitis C virus genomic RNA of the present invention may further comprise at least one selective marker gene and/or at least one reporter gene, and at least one IRES sequence.

In this case, the modified hepatitis C virus genomic RNA comprises the above-described 5' untranslated region, at least one selective marker gene and/or at least one reporter gene, at least one IRES sequence, a core protein coding sequence, an E1 protein coding sequence, an E2 protein coding sequence, a p7 protein coding sequence, an NS2 protein coding sequence, an NS3 protein coding sequence, an NS4A protein coding sequence, an NS4B protein coding sequence, an NS5A protein coding sequence, an NS5B protein coding sequence, and a 3' untranslated region, in this order, in the direction from the 5'-terminus to the 3'-terminus.

As an example of the aforementioned modified hepatitis C virus genomic RNA, the present specification describes modified hepatitis C virus genomic RNA, which comprises:
(a) RNA having the nucleotide sequence shown in SEQ ID NO: 11; or
(b) RNA having a nucleotide sequence comprising a deletion, substitution, or addition of one or more, preferably 100, more preferably 50, and further more preferably 10 nucleotides, with respect to the nucleotide sequence shown in SEQ ID NO: 11, and which can be autonomously replicated and generate hepatitis C virus particles.

In addition, the present invention also provides a cell into which the modified hepatitis C virus genomic RNA of the present invention is introduced, and which replicates the above-described hepatitis C virus genomic RNA and can generate virus particles. Herein, a proliferative cell is preferably used as a host cell. Particularly preferred examples of such a host cell may include eukaryotic cells, including human liver-derived cells such as Huh7 cells, HepG2 cells, IMY-N9 cells, HeLa cells, or 293 cells, human cervical cells, and human fetal kidney-derived cells.

Moreover, the present invention also provides: a method for producing hepatitis C virus particles, which is characterized in that the method comprises culturing the aforementioned cell and recovering virus particles from the culture; and hepatitis C virus particles produced by the above method.

Furthermore, the present invention also provides: a method for producing a hepatitis C virus-infected cell, which is characterized in that the method comprises culturing the aforementioned cell and infecting another cell with virus particles contained in the culture; and a hepatitis C virus-infected cell produced by the above method. In the present invention, such HCV particles are purified by column chromatography and/or density gradient centrifugation, so as to obtain HCV particles with purity that allows for industrial use for pharmaceuticals. Chromatography used herein is one or more types of chromatography selected from ion exchange chromatography, gel filtration chromatography, and affinity chromatography. Density gradient centrifugation is carried out using one or more solutes selected from cesium chloride, sucrose, and polymers of sugar, so as to purify HCV.

Still further, the present invention also provides a method for screening an anti-hepatitis C virus substance using the cell of the present invention or a hepatitis C virus-infected cell. This method is characterized in that the method comprises culturing the cell of the present invention or a hepatitis C virus-infected cell in the presence of a test substance and detecting hepatitis C virus RNA or virus particles in the culture, thereby evaluating the effects of anti-hepatitis C virus in the above-described test substance.

Still further, the present invention also provides a method for producing a hepatitis C vaccine using the hepatitis C virus particles of the present invention or a portion thereof as an antigen.

Still further, the present invention also provides: a method for replicating and/or expressing a foreign gene in a cell, which is characterized in that the method comprises inserting RNA encoding the foreign gene into the modified hepatitis C virus genomic RNA of the present invention and introducing genomic RNA into a cell of interest, so as to replicate or express the foreign gene therein; and a hepatic cell-directed virus vector, which comprises the modified hepatitis C virus genomic RNA of the present invention.

According to the present invention, HCV virus particles having infectivity can be produced using a cultured cell system. Moreover, even in the case of an HCV strain that cannot be autonomously replicated and that is isolated from patients, a region thereof corresponding to the region from the NS3 region to the 3'-terminus is substituted with JFH1 virus genomic RNA, or the NS5B region is substituted with JFH1 NS5B, so that the above HCV strain can autonomously replicate in vitro. Accordingly, HCV virus particles with various genotypes can be produced in a cultured cell system, and these virus particles are effectively used for studies regarding the HCV infection process, or for production of a screening system for various substances that affect such an HCV infection process and an HCV vaccine.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 1 is a schematic view showing the procedures for constructing template DNA used for producing the HCV genomic RNA of the present invention. The figure shows the structure of a plasmid clone pJFH1 produced by inserting full-length HCV genome downstream of a T7 promoter. The symbols shown in the figure have the following meanings. T7: T7 RNA promoter; 5'-UTR: 5' untranslated region; C: core protein; E1, E2: envelope proteins; NS2, NS3, NS4A, NS4B, NS5A, NA5B: nonstructural proteins; 3'-UTR: 3' untranslated region; AgeI, PmeI, XbaI: the cleavage sites of restriction enzymes of AgeI, PmeI, and XbaI; and GDD: the position of an amino acid motif GDD corresponding to the active center of an NS5B protein;

FIG. 2 is a photograph showing the results of Northern blot analysis indicating replication of rJFH1 in Huh7 cells, into which the rJFH1 that is HCV genomic RNA has been introduced;

FIG. 3 shows the results regarding detection of an HCV core protein, an NS3 protein, an NS5A protein, and an E2 protein, in a medium;

FIG. 4 shows the results regarding the time course of changes in the release of a core protein from cells, into which HCV genomic RNA has been introduced, into a medium;

FIG. 5 includes graphs each showing the amount of an HCV core protein and the amount of HCV genomic RNA in each fraction obtained by fractionating in a sucrose density gradient manner the culture supernatant of Huh7 cells, into which rJFH1 has been introduced. The closed circle represents an HCV Core (core) protein, and the open circle represents HCV genomic RNA. FIG. 5A shows the results of untreated rJFH1-introduced Huh7 cells. FIG. 5B shows the results of RNase-treated rJFH1-introduced Huh7 cells. FIG. 5C shows the results of NP40-treated rJFH1-introduced Huh7 cells. FIG. 5D shows the results of NP40+RNase-treated rJFH1-introduced Huh7 cells;

FIG. 6 shows the infectivity of virus particles secreted in the culture solution of rJFH1-introduced Huh7 cells. FIG. 6A includes photographs showing the results of immunostaining with an anti-core antibody (left) and with an anti-NS5A antibody (right). FIG. 6B is a graph showing the number of positive cells stained with an anti-core antibody. FIG. 6C includes graphs showing a change over time of HCV RNA level in the cells (left) and in the supernatant (right);

FIG. 7 shows the infectivity of virus particles secreted in the culture solution of rJCH1/NS5B(jfh1)-introduced Huh7 cells. FIG. 7A is a graph showing amplification of the HCV RNA of virus particles secreted in the culture solution of rJCH1/NS5B(jfh1)-introduced Huh7 cells, in naïve Huh7 cells. FIG. 7B is a graph showing the number of positive cells stained with an anti-core antibody;

FIG. 8 shows the structure of a TH/JFH1 chimeric replicon;

Figure 9:
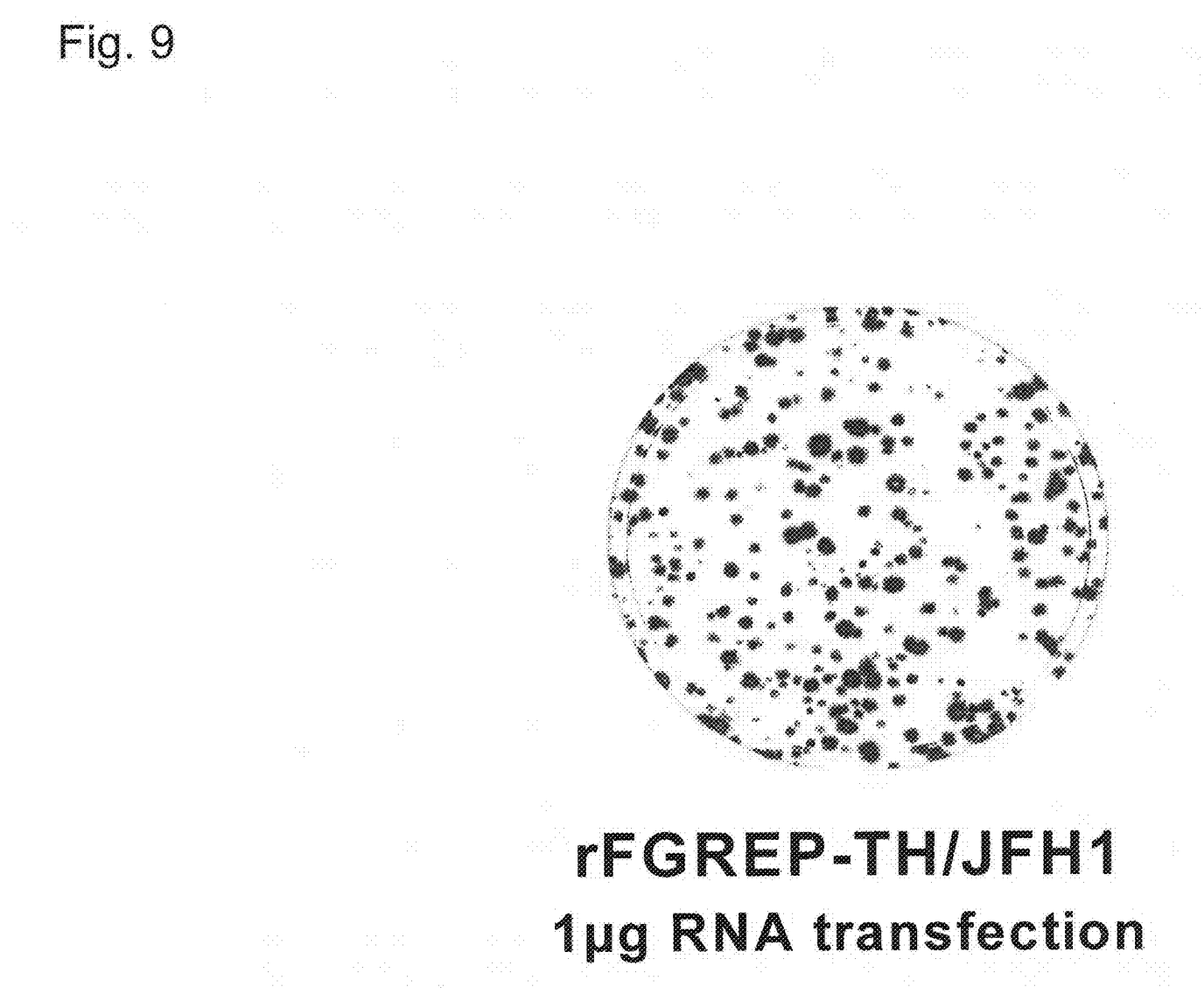

FIG. 9 shows the results regarding formation of colonies by transfection of rTH/JFH1 chimeric replicon RNA;

Figure 11:
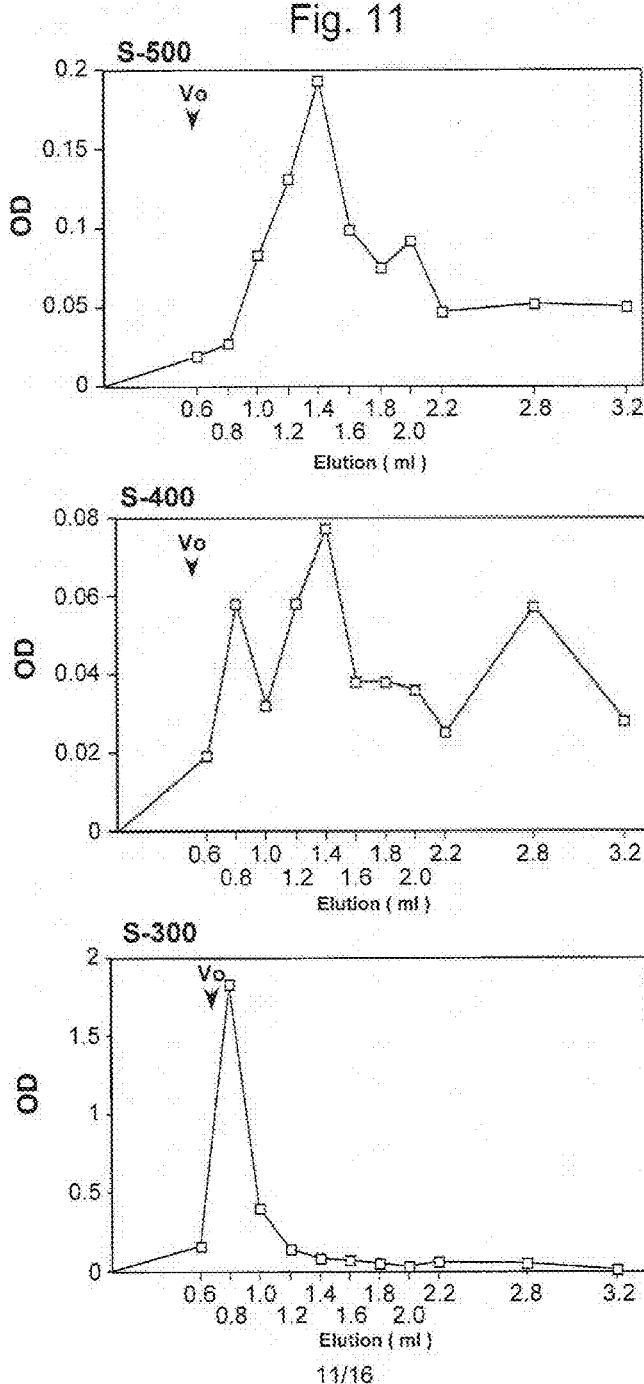
Figure 13:
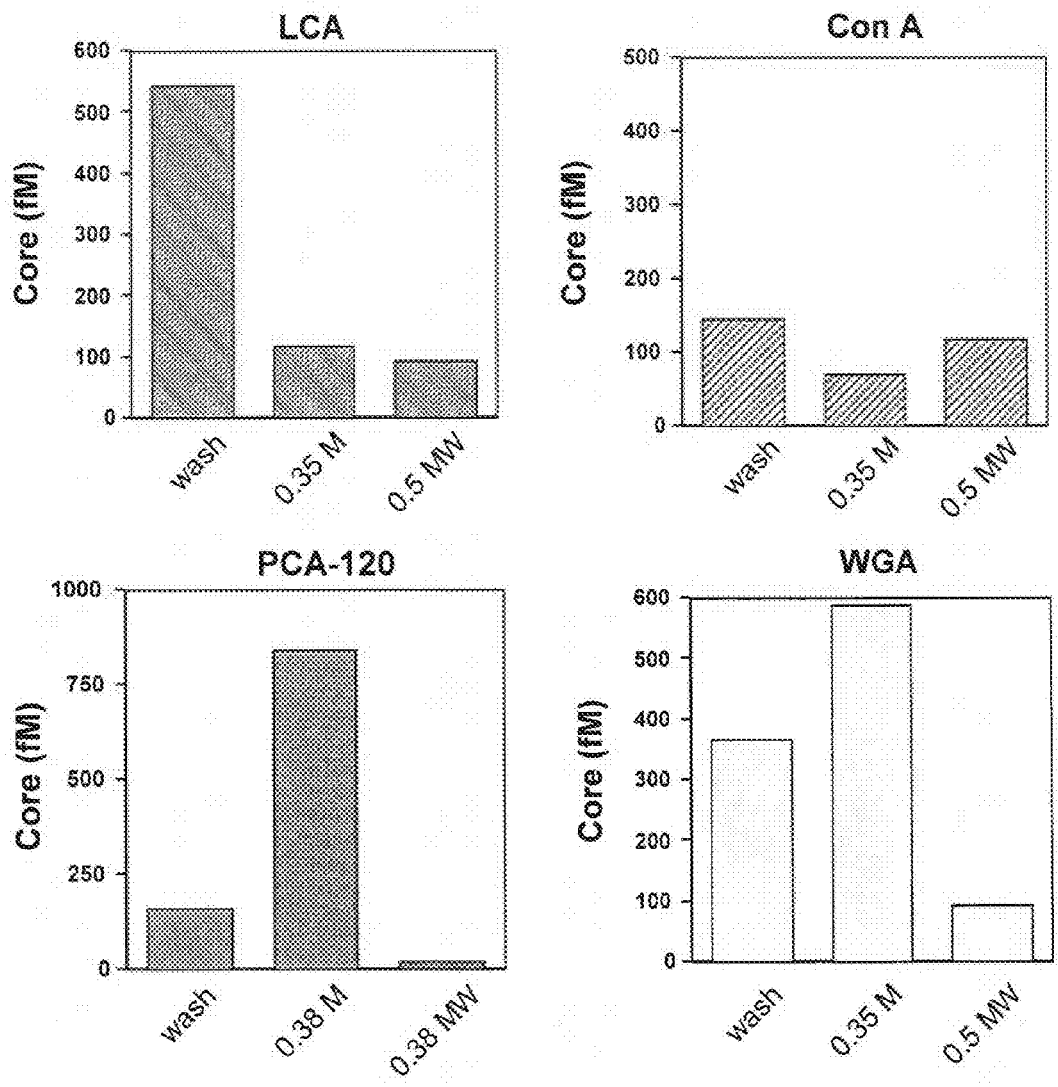
Figure 15:
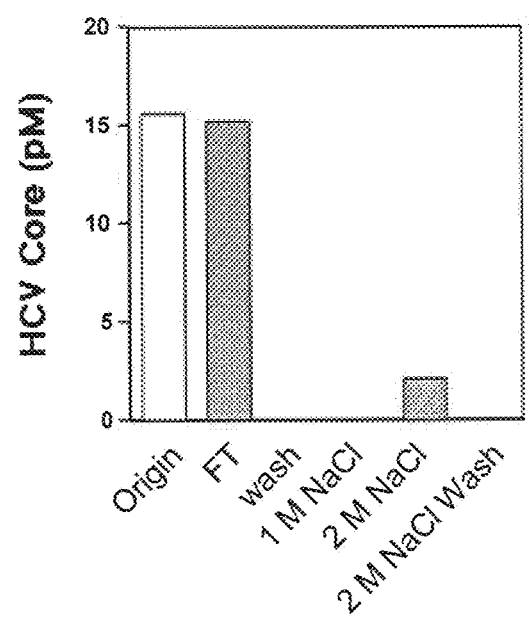

FIG. 11 shows elution profiles in gel filtration chromatography. The longitudinal axis represents absorbance at a wavelength of 490 nm. S-300, S-400, and S-500 represent Sephacryl® S-300, S-400, and S-500, respectively. The horizontal axis represents the elution amount eluted from the column;

FIG. 12 shows elution profiles in ion exchange chromatography. The longitudinal axis represents the amount of a core protein in HCV particles;

FIG. 13 shows elution profiles in lectin affinity chromatography. The longitudinal axis represents the amount of a core protein in HCV particles;

FIG. 14 shows elution profiles in two types of affinity chromatography using heparin and sulfated cellulofine. The longitudinal axis represents absorbance at a wavelength of 490 nm;

FIG. 15 shows an elution profile in blue dye affinity chromatography. The longitudinal axis represents the amount of a core protein in HCV particles; and FIG. 16 shows purification profiles involving the combined use of column chromatography with sucrose density gradient centrifugation. The longitudinal axis represents the amount of a core protein in HCV particles. With regard to sucrose density gradient centrifugation, the density of each fraction solution as well as the amount of a core protein in HCV are shown in the longitudinal axis.

This specification includes the contents as disclosed in the specification and/or drawings of Japanese Patent Application Nos. 2004-243975, 2004-290801, 2005-69527, and 2005-69725, which are priority documents of the present application.

BEST MODE FOR CARRYING OUT THE INVENTION

The present invention will be described in detail below.

1. Modified Chimeric Hepatitis C Virus Genomic RNA

The genome of a hepatitis C virus (HCV) is single-stranded RNA that is (+) strand consisting of approximately 9,600 nucleotides. This genomic RNA comprises a 5' untranslated region (which is also referred to as 5'-NTR or 5'-UTR), a translated region composed of a structural region and a nonstructural region, and a 3' untranslated region (which is also referred to as 3'-NTR or 3'-UTR). The structural region encodes HCV structural proteins, and the nonstructural region encodes a plurality of nonstructural proteins.

Such HCV structural proteins (core, E1, and E2) and HCV nonstructural proteins (NS2, NS3, NS4A, NS4B, NS5A, and NS5B) are translated as one continuous polyprotein from the translated region. Thereafter, the polyprotein is subjected to limited digestion with protease, so that the proteins can be released and generated. Among these structural and nonstructural proteins (namely, HCV virus proteins), core is a core protein, and E1 and E2 are envelope proteins. The nonstructural protein is a protein associated with replication of a virus per se. It has been known that NS2 has metalloprotease activity and that NS3 has serine protease activity (one third of the N-terminal side) and helicase activity (two thirds of the C-terminal side). Moreover, it has also been reported that NS4A is a cofactor to the protease activity of NS3 and that NS5B has RNA-dependent RNA polymerase activity.

At present, it has been known that the genotypes of HCV are classified into at least type 1 to type 6. HCV is classified into various genotypes (HCV1a, HCV1b, HCV2a, HCV2b, etc.) depending on its sequence, in accordance with the international classification of Simmonds et al. (refer to Simmonds P. et al., Hepatology, (1994) 10, pp. 1321-1324). In the present invention, HCV genomic RNA that cannot be autonomously replicated is not limited to the aforementioned known virus types, but it includes all types of HCV genomic RNA that cannot be autonomously replicated, that is, ability to release infectious particles out of the cell. In the present invention, the expression RNA "can be autonomously replicated" or "is autonomously replicated" is used to mean that when HCV genomic RNA is introduced into a cell, the HCV genomic RNA autonomously replicates, that is, it can release infectious particles out of the cell.

In the present specification, RNA including the aforementioned HCV genomic RNA that can be autonomously replicated in a cultured cell system is referred to as "replicon RNA" or "RNA replicon." In the present specification, the replicon RNA of the present invention comprising the full-length replicon RNA is referred to as "full-length HCV replicon RNA." The full-length HCV replicon RNA of the present invention has ability to generate virus particles. Moreover, the modified hepatitis C virus genomic RNA of the present invention is full-length HCV replicon RNA.

The modified hepatitis C virus genomic RNA of the present invention includes modified hepatitis C virus genomic RNA, which has the nucleotide sequences of genomic RNA portions of two or more types of hepatitis C viruses, comprising a 5' untranslated region, a core protein coding sequence, an E1 protein coding sequence, an E2 protein coding sequence, a p7 protein coding sequence, an NS2 protein coding sequence, the protein coding sequence of each of NS3, NS4A, NS4B, NS5A, and NS5B of a JFH1 strain, and a 3' untranslated region, and which can be autonomously replicated. Specifically, in one embodiment, the present invention includes modified hepatitis C virus genomic RNA, which is produced by substituting a hepatitis C virus genomic RNA portion ranging from the NS3 protein coding sequence to the NS5B protein coding sequence that is a genome sequence at the 3'-terminus, with a partial RNA sequence encoding the NS3, NS4, NS5A, and NS5B proteins of the JFH1 strain shown in SEQ ID NO: 1 (RNA sequence obtained by substituting T with U in a sequence corresponding to 3867-9678 of the DNA sequence deposited under Genbank Accession No. AB047639), and which can be autonomously replicated.

In another embodiment, the present invention provides modified hepatitis C virus genomic RNA, which is produced by substituting the NS5B protein coding sequence of hepatitis C virus genomic RNA with the NS5B protein coding sequence of the JFH1 strain shown in SEQ ID NO: 2, and which can be autonomously replicated.

Preferably, the present invention includes modified hepatitis C virus genomic RNA obtained using hepatitis C viruses with genotypes 1b and 2a, which has a nucleotide sequence, comprising a 5' untranslated region, a core protein coding sequence, an E1 protein coding sequence, an E2 protein coding sequence, a p7 protein coding sequence, an NS2 protein coding sequence, the protein coding sequence of each of NS3, NS4A, NS4B, NS5A, and NS5B of the JFH1 strain, and a 3' untranslated region, and which can be autonomously replicated.

The above-described modified hepatitis C virus genomic RNA may further comprise at least one selective marker gene and/or at least one reporter gene, and at least one IRES sequence.

In the present invention, using an HCV strain that can be autonomously replicated in a cultured cell system with the combination of an HCV strain that cannot be autonomously replicated in such a cultured cell system, as two or more types of hepatitis C viruses, the HCV strain that cannot be autonomously replicated can be modified to be made autonomously replicated. Otherwise, a virus strain that is autonomously replicated efficiently can be modified to be made autonomously replicated very efficiently.

Specific examples of a known HCV strain with type 1a may include an HCV-1 strain, an HCV-H strain, and an HCV-J1 strain. Specific examples of a known HCV strain with type 1b may include an HCV-con1 strain, an HCV-TH strain, an HCV-J strain, an HCV-JT strain, and an HCV-BK strain. Specific examples of a known HCV strain with type 2a may include an HCV-J6 strain, a JFH-1 strain, and JCH1 strain. An example of a known HCV strain with type 2b may be an HC-J8 strain. An example of a known HCV strain with type 3a may be an E-b1 strain. The structure of these viruses is basically composed of 5'-UTR, core, E1, E2, p7, NS2, NS3, NS4a, NS4b, NS5a, NS5b, and 3'-UTR (as described above). The nucleotide sequence of each region of the aforementioned each HCV strain has been determined. For example, the nucleotide sequences of regions corresponding to core, E1, E2, p7, and NS2 have been determined on the full-length sequence of the TH strain. In addition, on the sequence of the HCV-JT strain, regions corresponding to core, E1, E2, p7, and NS2 have been determined. An example of the replicon RNA of the present invention may be chimeric HCV replicon RNA, which is obtained, using a JFH1 strain with HCV type 2a, and strains other than the JFH1 strain with type HCV type 2a, such as an HCV-1 strain, an HCV-H strain, an HCV-J1 strain, an HCV-con1 strain, an HCV-TH strain (Wakita et al., J. Biol. Chem., (1994) 269, pp. 14205-14210; and Moradpour et al., Biochem. Biophys. Res. Commun., (1998) 246, pp. 920-924), an HCV-J strain, an HCV-JT strain, an HCV-BK strain, an HCV-J6 strain, a JCH1 strain, an HC-J8 strain, or an E-b1 strain.

Furthermore, a preferred example of the modified HCV genomic RNA of the present invention may be HCV genomic RNA obtained by substituting a region corresponding to the region from the NS3 region to the 3'-terminal side in the HCV genomic RNA of the hepatitis C virus JFH1 strain with the virus genomic RNA of JFH1, or by substituting the NS5B protein coding sequence with the NS5B protein coding sequence of another HCV genomic RNA or inserting the above sequence therein. For example, in the case of HCV genomic RNA JCH1(ref) that has been known as being incapable of replicating in vitro, a region corresponding to the region from the NS3 region thereof to the 3'-terminal side is substituted with the virus genomic RNA of JFH1, so that the HCV genomic RNA can be modified to result in HCV genomic RNA that can autonomously replicate.

Moreover, in the case of HCV genomic RNA Con-1 clone (ref) with HCV genotype 1b (EMBL Accession No. AJ238799), an RNA sequence portion thereof encoding NS3, NS4, NS5A, and NS5B proteins is substituted with the RNA sequence of a JFH1 strain that encodes NS3, NS4, NS5A, and NS5B proteins, or only the RNA sequence portion encoding the NS5B protein of the Con-1 clone (ref) with HCV genotype 1b is substituted with the RNA sequence that encodes the NS5B protein of the JFH1 strain, so that the HCV genomic RNA can be modified to result in HCV genomic RNA that can autonomously replicate.

The full-length replicon using a Con-1 clone gene can be autonomously replicated, but does not form HCV particles (refer to Pietschmann et al., Journal of Virology, (2002) 76, pp. 4008-4021). However, as described in the example of the present invention, such HCV particles can be formed by substituting an RNA sequence portion encoding NS3, NS4, NS5A, and NS5B proteins with the RNA sequence that encodes the NS3, NS4, NS5A, and NS5B proteins of the JFH1 strain. That is to say, according to the method of the present invention, hepatitis C virus genomic RNA that can be autonomously replicated but is unable to form HCV particles can be converted to modified hepatitis C virus genomic RNA that can form particles.

Moreover, even in the case of HCV that is unable to produce a replicon that can be autonomously replicated, such as a TH strain or a JCH strain, HCV particles are formed by producing a chimeric gene thereof with the JFH-1 strain, as described in the example of the present invention. Accordingly, the present invention enables conversion of HCV genomic RNA that cannot be autonomously replicated to modified hepatitis C virus genomic RNA that can form HCV particles.

Furthermore, by introducing mutation into NS5B of the RNA sequence portion of the JFH1 strain, the growth of HCV genomic RNA is terminated, and the particle generation of HCV is also terminated. Thus, apparently, NS5B plays an important role in allowing the HCV genomic RNA to be autonomously replicated and generate particles.

Currently, HCV is classified into various genotypes (HCV1a, HCV1b, HCV2a, HCV2b, etc.) depending on its sequence, in accordance with the international classification of Simmonds et al. (refer to Simmonds P. et al., Hepatology, (1994) 10, pp. 1321-1324). In the present invention, HCV genomic RNA that cannot be autonomously replicated is not limited to the aforementioned known virus types, but it includes all types of HCV genomic RNA that cannot be autonomously replicated.

In the present specification, the NS5B protein coding sequence is the coding sequence of the NS5B protein derived from the JFH1 strain (SEQ ID NO: 3), and it has the nucleotide sequence shown in SEQ ID NO: 2. However, the NS5B protein coding sequence of the present invention also includes nucleotide sequences that can hybridize with the nucleotide sequence shown in SEQ ID NO: 2 under stringent conditions, as long as such nucleotide sequences encode amino acids that function as an NS5B protein (for example, an NS5B protein comprising conservative substitution).

The term "stringent conditions" is used to mean, for example, conditions consisting of a sodium concentration between 300 and 2,000 mM and a temperature between 40° C. and 75° C., and more preferably, a sodium concentration between 600 and 900 mM and a temperature of 65° C. Persons skilled in the art can easily obtain the aforementioned NS5B homolog, with reference to Molecular Cloning (Sambrook J. et al., Molecular Cloning: A Laboratory Manual $2^{nd}$ ed., Cold Spring Harbor Laboratory Press, 10 Skyline Drive Plainview, N.Y. (1989)).

The HCV genomic RNA of the present invention has an RNA sequence portion that encodes NS3, NS4, NS5A, and NS5B proteins in the JFH1 HCV genomic RNA, or an NS5B protein coding sequence.

In one embodiment, the HCV genomic RNA of the present invention is RNA, which has a nucleotide sequence that includes a 5' untranslated region, a core protein coding sequence, an E1 protein coding sequence, an E2 protein coding sequence, an NS2 protein coding sequence, an NS3 protein coding sequence, an NS4A protein coding sequence, an NS4B protein coding sequence, an NS5A protein coding sequence, an NS5B protein coding sequence, and a 3' untranslated region, on hepatitis C virus strain genomic RNA. Moreover, in the above RNA, the aforementioned RNA sequence portion encoding NS3, NS4, NS5A, and NS5B proteins is an RNA sequence portion encoding NS3, NS4, NS5A, and NS5B proteins, which is derived from extraneously introduced JFH1 HCV genomic RNA. Preferably, this is RNA, wherein the NS5B protein coding sequence thereof is an NS5B protein coding sequence derived from extraneously introduced JFH1 HCV genomic RNA.

In the specification of the present application, the "5' untranslated region (5'-NTR or 5'-UTR)," "core protein coding sequence (core region or C region)," "E1 protein coding sequence (E1 region)," "E2 protein coding sequence (E2 region)," "NS2 protein coding sequence (NS2 region)," "NS3 protein coding sequence (NS3 region)," "NS4A protein coding sequence (NS4A region)," "NS4B protein coding sequence (NS4B region)," "NS5A protein coding sequence (NS5A region)," "NS5B protein coding sequence (NS5B region)," "3' untranslated region (3'-NTR or 3'-UTR)," and other specific regions or sites, have already been known in various genotypes. The aforementioned regions or sites of an unknown HCV strain can easily be determined by aligning the full-length genomic RNA sequence of a known HCV with that of the above HCV strain.

The term "selective marker gene" is used in the present invention to mean a gene, which can impart to cells, selectivity for selecting only the cells wherein the gene has been expressed. A common example of such a selective marker gene may be an antibiotic resistance gene. Examples of such a selective marker gene that can preferably be used in the present invention may include a neomycin resistance gene, a thymidine kinase gene, a kanamycin resistance gene, a pyrithiamin resistance gene, an adenylyl transferase gene, a zeocin resistance gene, and a puromycin resistance gene. Of these, a neomycin resistance gene and a thymidine kinase gene are preferable, and a neomycin resistant gene is more preferable. However, selective marker genes used in the present invention are not limited thereto.

The term "reporter gene" is used in the present invention to mean a marker gene that encodes a gene product that acts as an indicator of the expression of the gene. A common example of such a reporter gene may be a structural gene of enzyme that catalyzes a luminous reaction or a color reaction. Examples of a reporter gene that can preferably be used in the present invention may include a chloramphenicol acetyl transferase gene derived from transposon Tn9, a β-glucuronidase or β-galactosidase gene derived from *Escherichia coli*, a luciferase gene, a green fluorescent protein gene, an aequorin gene derived from jellyfish, and a secreted form of human placental alkaline phosphatase (SEAP) gene. However, reporter genes used in the present invention are not limited thereto.

Either one of the aforementioned selective marker gene and reporter gene may be contained in replicon RNA, or both of them may also be contained therein. With regard to such a selective marker gene or reporter gene, one gene may be contained in modified hepatitis C virus genomic RNA, or two or more genes may also be contained therein.

The HCV genomic RNA of the present invention may further comprise RNA encoding any foreign gene that is to be expressed in cells, into which the full-length HCV genomic RNA is introduced. Such RNA encoding a foreign gene may be ligated downstream of the 5' untranslated region, or may be ligated upstream of the 3' untranslated region. Also, such RNA may be inserted into any space among a core protein coding sequence, an E1 protein coding sequence, an E2 protein coding sequence, an NS2 protein coding sequence, an NS3 protein coding sequence, an NS4A protein coding sequence, an NS4B protein coding sequence, an NS5A protein coding sequence, and an NS5B protein coding sequence.

When HCV genomic RNA comprising RNA encoding a foreign gene is translated in cells, into which the RNA has been introduced, it allows a gene product encoded by the foreign gene to express. Accordingly, such HCV genomic RNA comprising RNA encoding a foreign gene can preferably be used also for the purpose of generating the gene product of the foreign gene in cells.

In the HCV genomic RNA of the present invention, the aforementioned virus protein coding sequences, a foreign gene and others are ligated to one another, such that they can be translated from the HCV genomic RNA, using a correct reading frame. Proteins encoded by the HCV genomic RNA are preferably ligated to one another via protease cleavage sites or the like, such that the proteins are translated in the form of a continuous polypeptide and it is allowed to express, and such that the polypeptide is then cleaved with protease into each protein and then released.

The thus produced HCV genomic RNA comprising an RNA sequence portion encoding the NS3, NS4, NS5A, and NS5B proteins of the JFH1 strain is introduced into suitable host cells, so as to obtain recombinant cells that can autonomously replicate the HCV genomic RNA, and preferably can persistently autonomously replicate the HCV genomic RNA (that is, can replicate HCV genomic RNA). Hereinafter, in the present specification, such recombinant cells that can replicate HCV genomic RNA comprising an RNA sequence portion encoding the NS3, NS4, NS5A, and NS5B proteins of the JFH1 strain is referred to as "HCV genomic RNA-replicating cells."

The type of host cells used for such "HCV genomic RNA-replicating cells" is not particularly limited, as long as they can be subcultured. Eukaryotic cells are preferable. Human cells are more preferable, and human liver-derived cells, human cervical cells, and human fetal kidney-derived cells are further more preferable. Moreover, proliferative cell lines including cancer cell strains or stem cell strains are preferable. Among others, Huh7 cells, HepG2 cells, IMY-N9 cells, HeLa cells, 293 cells, and the like, are particularly preferable. Commercially available cells may be used as such cells, or such cells may also be procured from cell depository institutions. Otherwise, cells established from any cells (cancer cells or stem cells, for example) may also be used.

HCV genomic RNA can be introduced into host cells using any known technique. Examples of such an introduction method may include electroporation, the particle gun method, the lipofection method, the calcium phosphate method, the microinjection method, and the DEAE sepharose method. Of these, a method involving electroporation is particularly preferable.

HCV genomic RNA may be introduced singly, or it may be mixed with another nucleic acid and then introduced. In order to change the amount of HCV genomic RNA introduced while the amount of RNA introduced is kept constant, a certain amount of HCV genomic RNA may be mixed with total cellular RNA extracted from cells, into which the HCV genomic RNA is to be introduced, so as to prepare a certain total amount of RNA, and thereafter, the total amount of RNA may be introduced into cells. The amount of HCV genomic RNA introduced into cells may be determined depending on an introduction method used. The amount of such HCV genomic RNA introduced is preferably between 1 picogram and 100 micrograms, and more preferably between 10 picograms and 10 micrograms.

Replication of HCV genomic RNA in the "HCV genomic RNA-replicating cells" can be confirmed by any known RNA detection method. For example, total RNA extracted from cells is subjected to the Northern hybridization method using a DNA fragment specific to the introduced HCV genomic RNA as a probe, or to the RT-PCR method using primers specific to the introduced HCV genomic RNA.

Moreover, when an HCV protein is detected in proteins extracted from the "HCV genomic RNA-replicating cells," it can be determined that the cells replicate HCV genomic RNA. Such an HCV protein can be detected by any known method for detecting protein. For example, such an HCV protein can be detected by allowing an antibody reacting with an HCV protein that must be expressed from the introduced HCV genomic RNA to react with a protein extracted from the cells. More specifically, a protein sample extracted from the cells is blotted on a nitrocellulose membrane, an anti-HCV protein antibody (e.g., an anti-NS3-specific antibody, or an antiserum collected from a patient with hepatitis C) is then allowed to react therewith, and the anti-HCV protein antibody is then detected, for example.

The fact that HCV genomic RNA can be autonomously replicated can be confirmed, for example, by transfecting Huh7 cells with RNA as a target, culturing the Huh7 cells, and subjecting RNA extracted from the cells in the obtained culture to Northern blot hybridization, using a probe capable of specifically detecting the introduced RNA, but such confirmation method is not limited thereto. Specific operations to confirm that the RNA can be autonomously replicated are found in descriptions regarding confirmation of expression of HCV protein or detection of HCV genomic RNA in the example of the present specification.

2. Production of HCV Particles

The HCV genomic RNA-replicating cells produced as described above are able to generate HCV virus particles in vitro. That is to say, the HCV genomic RNA-replicating cells of the present invention are cultured in a suitable medium, and the generated virus particles are then collected from a culture (preferably, a culture solution), thereby easily obtaining HCV particles.

The virus particle-generating ability of the HCV genomic RNA-replicating cells can be confirmed by any known virus detection method. For example, a culture solution containing cells that presumably generate virus particles is fractionated in a sucrose density gradient manner, and the density, HCV core protein concentration, and HCV genomic RNA amount of each fraction are then measured. As a result, when the peak of the HCV core protein corresponds to that of the HCV genomic RNA, and when the density of a fraction in which the peak is detected is lower than the density of the same fraction, which is fractionated after the culture supernatant has been treated with 0.25% NP40 (polyoxyethylene(9)octylphenyl ether) (for example, between 1.15 mg and 1.22 mg), it can be confirmed that the cells have virus particle-generating ability.

HCV virus particles released into the culture solution can also be detected using an antibody reacting with a core protein, an E1 protein, or an E2 protein. Moreover, it is also possible to indirectly detect the existence of HCV virus particles by amplifying HCV genomic RNA contained in HCV virus particles in the culture solution and then detecting the amplified product according to the RT-PCR method using specific primers.

3. Infection of Other Cells with the HCV Particles of the Present Invention

The HCV virus particles generated by the method of the present invention has infectious ability to cells (preferably, HCV-sensitive cells). The present invention also provides a method for producing a hepatitis C virus-infected cell, which comprises culturing HCV genomic RNA-replicating cells and then infecting other cells (preferably, HCV-sensitive cells) with virus particles contained in the obtained culture (preferably, a culture solution). The term "HCV-sensitive cells" is used herein to mean cells having infectivity to HCV. Such HCV-sensitive cells are preferably hepatic cells or lymphocyte cells, but examples are not limited thereto. Specific examples of such hepatic cells may include primary hepatic cells, Huh7 cells, HepG2 cells, IMY-N9 cells, HeLa cells, and 293 cells. Specific examples of such lymphocyte cells may include Molt4 cells, HPB-Ma cells, and Daudi cells. However, examples are not limited thereto.

When cells (for example, HCV-sensitive cells) are infected with HCV particles generated in the HCV genomic RNA-replicating cells of the present invention, HCV genomic RNA is replicated in the infected cells, and virus particles are then formed. Thereafter, by allowing cells to be infected with the virus particles generated in the HCV genomic RNA-replicating cells of the present invention, HCV genomic RNA can be replicated in the cells, and virus particles can be further produced.

When animals that can be infected with the HCV virus, such as chimpanzees, are infected with the HCV virus particles generated in the HCV genomic RNA-replicating cells of the present invention, the particles may cause hepatitis derived from HCV to the animals.

4. Purification of HCV Particles

A solution containing HCV viruses used in purification of the HCV particles may be derived from one or more selected from the blood derived from patient infected with HCV, HCV-infected cultured cells, a cell culture medium containing cells that generate HCV particles as a result of genetic recombination, and a solution obtained from homogenate of the cells.

A solution containing HCV viruses is subjected to centrifugation and/or filtration through a filter, so as to eliminate cells and cell residues. The solution obtained by elimination of such residues can be concentrated at a magnification between 10 and 100 times, using an ultrafiltration membrane with molecular weight cut-off between 100,000 and 500,000.

The solution containing HCV, from which residues have been eliminated, can be purified by either one of chromatography and density gradient centrifugation as described below, or by the combined use of chromatography with density gradient centrifugation in any order. Representative chromatography and density gradient centrifugation methods will be described below, but the present invention is not limited thereto.

Gel filtration chromatography can be used to purify HCV particles, preferably using a chromatography carrier having, as a gel matrix, a crosslinked polymer consisting of allyl dextran and N,N'-methylenebisacrylamide, and more preferably using Sephacryl® S-300, S-400, or S-500.

Ion exchange chromatography can be used to purify HCV particles, preferably using Q-Sepharose® as an anion exchange resin, and preferably using SP Sepharose® as a cation exchange resin.

Affinity chromatography can be used to purify HCV particles, preferably using, as a carrier, a resin as a ligand to which a substrate selected from heparin, sulfated cellulofine, lectin, and various pigments is allowed to bind. Such affinity chromatography can be used to purify HCV particles, more preferably using HiTrap Heparin HP®, HiTrap Blue HP®, HiTrap Benzamidine FF®, sulfated cellulofine, or carriers to which LCA, ConA, RCA-120, and WGA bind. Such affinity chromatography can be used to purify HCV particles, most preferably using sulfated cellulofine as a carrier. Unexpectedly, HCV particles have been purified at a magnification of 30 times, with regard to the ratio of the total protein mass in the solution to the number of HCV RNA copies before and after the purification.

In purification by density gradient centrifugation, as a solute that forms a density gradient, cesium chloride, sucrose, Nycodenz®, or a sugar polymer such as Ficoll® or Percoll®, can preferably be used. More preferably, sucrose can be used. In addition, as a solvent used herein, water or a buffer solution such as a phosphate buffer, a Tris buffer, an acetate buffer, or glycine buffer, can preferably be used.

The temperature applied to purification is preferably between 0° C. and 40° C., more preferably between 0° C. and 25° C., and most preferably between 0° C. and 10° C.

In a purification method involving density gradient centrifugation, the centrifugal force applied to the purification is preferably between $1\times10^4$ and $1\times10^9$ g, more preferably between $5\times10^4$ and $1\times10^7$ g, and most preferably between $5\times10^4$ and $5\times10^5$ g.

With regard to the combined use of purification methods, density gradient centrifugation and column chromatography may be combined in any order. Preferably, after HCV particles have been purified by multiple types of column chromatography, the resultant is subjected to density gradient centrifugation. More preferably, anion exchange column chromatography, and then, affinity chromatography are performed, so as to obtain a fraction containing HCV particles, and thereafter, the obtained fraction is purified by density gradient centrifugation. Most preferably, a fraction containing HCV particles obtained by column chromatography using Q-Sepharose® is further purified using a column with sulfated cellulofine, and thereafter, the obtained fraction containing HCV particles are purified by density gradient centrifugation. Moreover, dialysis or ultrafiltration can be carried out between the process of column chromatography and the process of density gradient centrifugation, so as to conduct substitution of a solute in the solution containing HCV particles and/or concentration of the HCV particles.

5. Other Embodiments of the Present Invention

HCV genomic RNA is replicated at high efficiency in the HCV genomic RNA-replicating cells of the present invention. Accordingly, using the HCV genomic RNA-replicating cells of the present invention, HCV genomic RNA can be produced at high efficiency.

In the present invention, HCV genomic RNA-replicating cells are cultured, and RNA is extracted from the culture (cultured cells and/or a culture medium). The extracted RNA is then electrophoresed, so as to isolate and purify the separated HCV genomic RNA, thereby producing HCV genomic RNA. The thus produced RNA comprises an HCV genomic sequence. By providing such a method for producing the RNA comprising the HCV genomic sequence, it becomes possible to analyze the HCV genome more in detail.

Moreover, the HCV genomic RNA-replicating cells of the present invention can preferably be used to produce an HCV protein. Such an HCV protein may be produced by any known method. For example, HCV genomic RNA is introduced into cells, so as to produce recombinant cells. Thereafter, the recombinant cells are cultured, and a protein is recovered from the obtained culture (cultured cells and/or a culture medium) by common methods.

HCV virus particles may have hepatic cell directivity. Thus, a hepatic cell-directed virus vector can be produced using the HCV genomic RNA of the present invention. This virus vector is preferably used for gene therapy. In the present invention, RNA encoding a foreign gene is incorporated into HCV genomic RNA, and the RNA is then introduced into cells, so as to introduce the above foreign gene into the cells. Thereafter, the foreign gene can be replicated and then expressed in the cells.

Furthermore, RNA is produced by exchanging the E1 protein coding sequence and/or E2 protein coding sequence in the HCV genomic RNA with the coat protein of a virus derived from other living species. The produced RNA is then introduced into cells, so as to produce virus particles. Thus, it becomes also possible to allow the cells of various living species to be infected with the RNA. In this case also, a foreign gene is further incorporated into the HCV genomic RNA, and the obtained RNA can be used as a cell-directed virus vector for allowing the foreign gene to express in various types of cells, depending on the directivity of a recombinant virus coat protein.

The present invention also relates to a method for producing a virus vector containing a foreign gene, which comprises inserting RNA encoding the foreign gene into HCV genomic RNA, introducing genomic RNA into cells, and culturing the cells, so as to allow the cells to generate virus particles.

The present invention also provides a method for producing a hepatitis C vaccine or a vaccine against the virus used for genetic recombination of a coat protein, using the HCV particles of the present invention or a portion thereof as an antigen, or using particles produced by genetic recombination of the virus coat protein for alteration of cell directivity or a portion thereof as an antigen. Moreover, a neutralizing antibody to HCV infection can also be produced, using the HCV particles of the present invention or a portion thereof as an antigen, or using particles produced by genetic recombination of the virus coat protein for altering of cell directivity or a portion thereof as an antigen.

The HCV genomic RNA-replicating cells of the present invention, or HCV-infected cells that are infected with virus particles generated in the HCV genomic RNA-replicating cells can be used, for example, for replication of HCV or reconstruction of the virus particles, or as a test system for screening for a substance that promotes or inhibits the release of the virus particles (an anti-hepatitis C virus substance). Specifically, for example, such cells are cultured in the presence of a test substance, and HCV genomic RNA or virus particles contained in the obtained culture is detected. Thereafter, it is determined whether or not the above test substance promotes or inhibits the replication of replicon RNA or HCV genomic RNA, the formation of such virus particles, or the release thereof, thereby screening for a substance that promotes or inhibits the growth of hepatitis C viruses. In this case, HCV genomic RNA contained in the culture may be detected by measuring the amount of the HCV genomic RNA in the RNA extracted from the aforementioned cells, the ratio thereof, or the presence or absence thereof. Virus particles contained in the culture (mainly, a culture solution) may be detected by measuring the amount of an HCV protein contained in the culture solution, the ratio thereof, or the presence or absence thereof.

HCV particles generated in the HCV genomic RNA-replicating cells of the present invention and HCV-sensitive cells can be used as test systems for screening for a substance that promotes or inhibits the binding of HCV to cells. Specifically, for example, HCV-sensitive cells are cultured together with HCV particles generated in the HCV genomic RNA-replicating cells of the present invention in the presence of a test substance. Thereafter, HCV genomic RNA or virus particles is detected in the obtained culture. It is determined whether or not the above test substance promotes or inhibits the replication of the HCV genomic RNA or the formation of the virus particles, thereby screening for a substance that promotes or inhibits the growth of hepatitis C viruses.

Such HCV genomic RNA or virus particles can be detected in accordance with the aforementioned means or the examples that will be described later. The above-described test system can be used for production or evaluation of a preventive agent, a therapeutic agent, or a diagnostic agent for hepatitis C virus infection.

Specific examples of the use of the aforementioned test system of the present invention are given below.

(1) Screening for a substance that inhibits the growth of HCV and the infection therewith Examples of a substance that inhibits the growth of HCV and the infection therewith may include: an organic compound that directly or indirectly affects the growth of HCV and the infection therewith; and an antisense oligonucleotide that hybridizes with the target sequence of HCV genome or a complementary strand thereof, so as to directly or indirectly affect the growth of HCV or the translation of an HCV protein.

(2) Evaluation of various substances having antiviral activity in cell culture

An example of the aforementioned various substances may be a substance obtained using rational drug design or high throughput screening (for example, isolated and purified enzyme).

(3) Identification of novel target to be attacked used for treatment of patients infected with HCV In order to identify a host cell protein playing an important role in replication of an HCV virus, the HCV genomic RNA-replicating cells of the present invention can be used, for example.

(4) Evaluation of ability of HCV virus to acquire resistance to agents or the like, and identification of mutation associated with such resistance (5) Production of virus protein used as antigen that can be used for development, production, and evaluation of diagnostic agent or therapeutic agent for hepatitis C virus infection (6) Production of virus protein and attenuated HCV used as antigens that can be used for development, production, and evaluation of vaccine against hepatitis C virus infection

EXAMPLES

The present invention will be more specifically described based on the following examples and drawings. However, these examples are not intended to limit the technical scope of the present invention.

Example 1

Production of HCV Genomic RNA

1. Construction of Expression Vector

Figure 1:
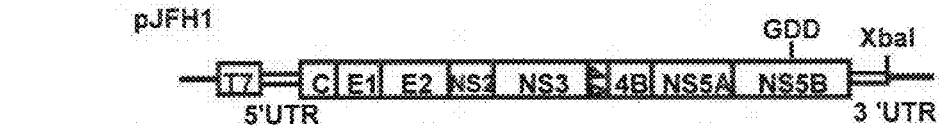

DNA corresponding to the total virus genomic region of a hepatitis C virus JFH1 strain (genotype 2a) isolated from patients suffering from fulminant hepatitis was obtained from a JFH1 clone comprising the full-length genomic cDNA of the above virus strain (Kato T. et al., J. Med. Virol. 64 (2001) pp. 334-339). The obtained DNA was then inserted downstream of a T7 RNA promoter sequence that had been inserted into a pUC19 plasmid. Specifically, an RT-PCR fragment obtained by amplification of the virus RNA of the JFH1 strain was cloned into a pGEM-T EASY vector (Promega), so as to obtain various plasmid DNA such as pGEM1-258, pGEM44-486, pGEM317-849, pGEM617-1323, pGEM1141-2367, pGEM2285-3509, pGEM3471-4665, pGEM4547-5970, pGEM5883-7003, pGEM6950-8035, pGEM7984-8892, pGEM8680-9283, pGEM9231-9634, and pGEM9594-9678 (Kato T. et al., Gastroenterology, 125 (2003) pp. 1808-1817). The virus genomic cDNA contained in each plasmid was ligated to one another by the PCR method and the use of restriction enzymes, and thus the full-length genomic cDNA was cloned. A T7 RNA promoter sequence was inserted upstream thereof, so as to obtain a JFH1 clone (pJFH1) (FIG. 1). It is to be noted that the full-length cDNA sequence of pJFH1 has been registered with International DNA Databank (DDBJ/EMBL/GenBank) under Accession No. AB047639.

Subsequently, with regard to an NS5B region in pJFH1 (nucleotide sequence: SEQ ID NO: 2; amino acid sequence: SEQ ID NO: 3), an amino acid motif GDD corresponding to the active center of RNA polymerase encoded by the above region was mutated to GND, so as to produce a mutant plasmid clone pJFH1/GND. Since the amino acid sequence of the active center of an NS5B protein encoded by the mutant plasmid clone pJFH1/GND is mutated, this clone cannot express an active NS5B protein necessary for replication of HCV RNA.

Subsequently, an E1 region and E2 region were deleted from JFH1, so as to produce pJFH1/ΔE1-E2. Moreover, the full-length HCV cDNA of a J6CF strain (GenBank Accession No. AF177036) that differs from the JFH1 strain, and that of a JCH1 strain (Kato T., et al., J. Med. Virol. 64 (2001) pp. 334-339), were inserted downstream of a T7 RNA promoter sequence that had been inserted into a pUC19 plasmid, so as to produce pJ6CF and pJCH1, respectively. Furthermore, the NS5B coding region of pJCH1 was substituted with the NS5B of JFH1, so as to produce pJCH1/NS5B(jfh1).

2. Production of HCV Genomic RNA

In order to produce template DNA used for RNA synthesis, each of the pJFH1, pJFH1/GND, pJFH1/ΔE1-E2, pJ6CF, pJCH1, and pJCH1/NS5B(jfh1) was cleaved with the restriction enzyme XbaI. Thereafter, 10 to 20 μg of each of these XbaI cleavage fragments was incubated with Mung Bean Nuclease 20 U (the total amount of reaction solution: 50 μl) at 30° C. for 30 minutes. Mung Bean Nuclease is an enzyme that catalyzes a reaction of selectively digesting a single-stranded portion in double-stranded DNA. In general, when RNA is synthesized directly using the aforementioned XbaI cleavage fragment as a template, replicon RNA, to the 3'-terminus of which 4 nucleotides CUAG that constitute a part of an XbaI recognition sequence are redundantly added, is synthesized. Thus, in the present example, such an XbaI cleavage fragment was treated with Mung Bean NuClease, so as to eliminate the 4 nucleotides CTAG from XbaI cleavage the fragment. Thereafter, the thus Mung Bean Nuclease-treated solution containing an XbaI cleavage fragment was subjected to a protein elimination treatment according to common methods, so that the XbaI cleavage fragment, from which the 4 nucleotides CTAG had been eliminated, could be purified. The purified fragment was used as template DNA.

Subsequently, RNA was synthesized in vitro from the above template DNA. Such RNA was synthesized by reacting 20 μl of a reaction solution containing 0.5 to 1.0 μg of the template DNA at 37° C. for 3 to 16 hours, using MEGAscript manufactured by Ambion.

After completion of the RNA synthesis, DNAse (2 U) was added to the reaction solution, and the mixture was then allowed to react at 37° C. for 15 minutes. Thereafter, RNA was further extracted with acidic phenol, and the template DNA was eliminated. Thus, several types of HCV RNA synthesized from the aforementioned template DNA derived from pJFH1 and pJFH1/GND were named as rJFH1, rJFH1/GND, rJFH1/ΔE1-E2, rJ6CF, rJCH1, and rJCH1/NS5B (jfh1).

With regard to the thus obtained HCV RNA, rJFH1 is RNA produced using DNA under GenBank Accession No. AB047639 as a template; JFH1/GND is RNA produced using, as a template, DNA obtained by substituting G at nucleotide 8618 with A, with respect to the DNA under GenBank Accession No. AB047639; rJFH1/ΔE1-E2 is RNA produced using, as a template, DNA comprising a deletion of the DNA sequence portion 989-2041, with respect to the DNA under GenBank Accession No. AB047639; rJ6CF is RNA produced using DNA under GenBank Accession No. AF177036 as a template; rJCH1 is RNA produced using DNA under GenBank Accession No. AB047640 as a template; and rJCH1/NS5B(jfh1) is RNA produced using, as a template, DNA obtained by ligating the DNA sequence portion 1-3866 of the DNA under GenBank Accession No. AB047640, to the DNA sequence portion 3867-9678 of the DNA under GenBank Accession No. AB047639, using the restriction enzyme AvrII site. The nucleotide sequences of these RNA can be confirmed.

Example 2

Generation of HCV Genomic RNA-Replicating Cells and Virus Particles in Cells

1. Replication of HCV Genome and Generation of Virus Particles in Cells

Each of the above-synthesized full-length HCV genomic RNA (rJFH1 and rJFH1/GND) was adjusted such that the total RNA level became 10 μg. Subsequently, the mixed RNA was introduced into Huh7 cells by the electroporation method. The Huh7 cells treated by electroporation were inoculated into a culture dish, and they were then cultured for 12 hours, 24 hours, 48 hours, and 72 hours. Thereafter, the cells were recovered, and RNA was then extracted from the cells. The extracted RNA was analyzed by the Northern blot method. Such Northern blot analysis was carried out in accordance with Molecular Cloning, A laboratory Manual, 2nd edition, J. Sambrook, E. F. Fritsch, T. Maniatis, Cold Spring Harbor Laboratory Press (1989). The RNA extracted from the cells was subjected to denatured agarose electrophoresis. After completion of the electrophoresis, the RNA was transcribed on a positive charge nylon membrane. A 32P-labeled DNA or RNA probe produced from pJFH1 was allowed to hybridize with the RNA transcribed on the membrane, as described above. Thereafter, the membrane was washed, and then exposed to a film, thereby detecting an RNA band specific to HCV genome.

Figure 2:
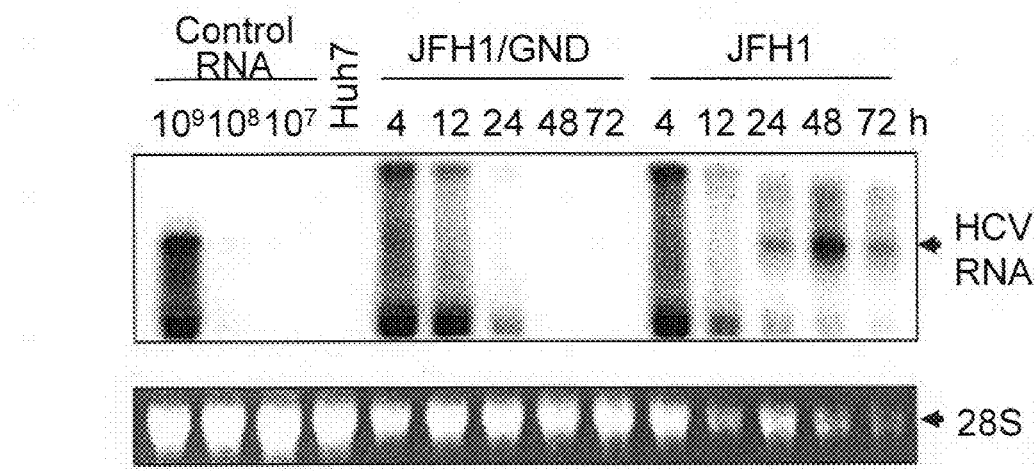

As shown in FIG. 2, when the cells were transfected with JFH1/GND, the introduced RNA band was confirmed as a weak signal, 4 hours after the transfection. However, such a signal was time dependent attenuation, and 24 hours later, almost no signal bands were confirmed.

On the other hand, when the cells were transfected with rJFH1, 4 to 12 hours after the transfection, the signal strength of the introduced RNA band was almost the same as in the case of introduction of JFH1/GND. Thereafter, the signal was attenuated once, but a clear RNA band signal was confirmed from 24 hours later onward. This signal was specific to HCV. In other words, it was considered that a portion of the introduced rJFH1 RNA replicated and grew. Such replication was not observed in rJFH1/GND obtained by mutating the active motif of NS5B that was an RNA-replicating enzyme. Thus, it was confirmed that the activity of NS5B is important for replication of the full-length RNA of HCV. The same experiment was carried out using the JCH1 strain (Kato T. et al., J. Med. Virol. 69 (2001) pp. 334-339), which had been isolated from patients with chronic hepatitis by the present inventors. In the case of this strain, replication of HCV RNA was not confirmed at all.

2. Detection of HCV Protein

A protein was extracted in time course dependent manner from cells transfected with rJFH1 or rJFH1/GND RNA according to common methods, and it was then analyzed by SDS-PAGE and the Western blot method. For such analysis, Huh7 cells were transiently transfected with expression plasmid DNA including an NS3, NS5A, core, or E2 gene, and the obtained cell extract was used as a positive control (NS3 protein). Moreover, a protein extracted from untransfected Huh7 cells was used as a negative control. A protein sample extracted from each cell clone was blotted onto a PVDF membrane (Immobilon-P, manufactured by Millipore). Thereafter, an anti-NS3-specific antibody (furnished from Dr. Moradpour; Wolk B. et al, J. Virology. 2000; 74: 2293-2304), an anti-NS5A-specific antibody (produced by inserting the NS5A region of JFH1 into an expression vector and using it to a mouse according to DNA immunization procedures), an anti-core-specific antibody (clone 2H9 antibody), and an anti-E2-specific antibody (produced by synthesizing the peptide of GTTTVGGAVARSTN (SEQ ID NO: 4) in the JFH1 E2 region and the peptide of CDLEDRDRSQLSPL (SEQ ID NO: 5) therein, and then immunizing a rabbit with the two synthetic peptides), were used to detect NS3, NS5A, core, and E2 proteins encoded by JFH1 RNA. Furthermore, as an intrinsic control, an actin protein was detected using an anti-actin antibody.

Figure 3:
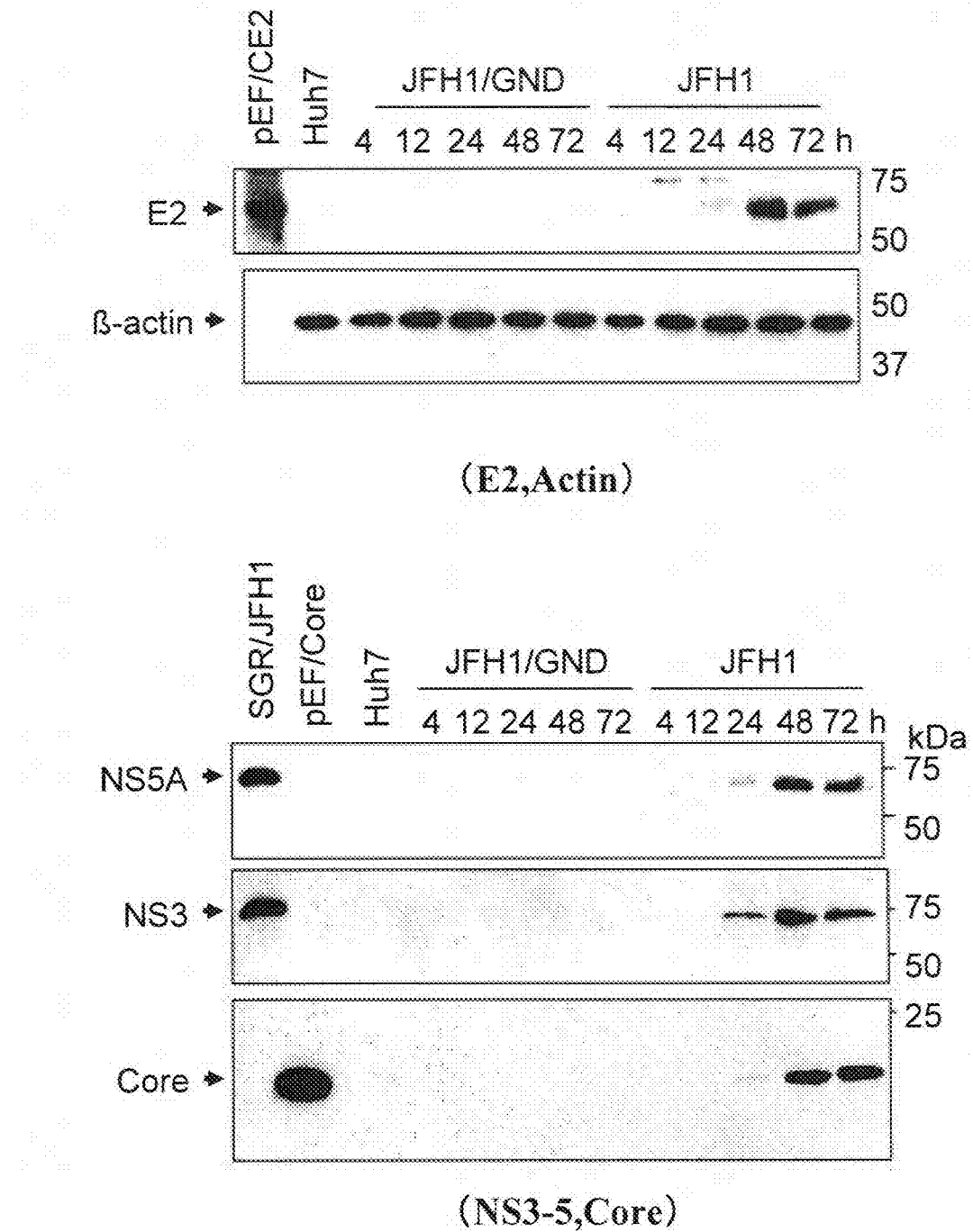

As shown in FIG. 3, in the cells transfected with rJFH1, from 24 hours after the transfection, NS3, NS5A, core, and E2 proteins were detected, and it was confirmed that the increase of expression level was time course dependent. In contrast, in the cells transfected with rJFH1/GND, or in the untransfected Huh7 cells, none of such NS3, NS5A, core, and E2 proteins was detected. It was found that these proteins were expressed therein as a result of autonomous replication of the transfected rJFH1.

From the results obtained in 1 and 2 above, it was confirmed that rJFH1 is replicated in cells established by transfection with rJFH1.

3. Detection of HCV Core Protein in Transfected Cell Culture Medium

Huh7 cells, into which rJFH1, rJFH1/GND, rJFH1/ΔE1-E2, rJ6CF, and rJCH1 had been introduced by electroporation, were inoculated into a culture dish. The cells were then cultured therein for 2 hours, 12 hours, 24 hours, 48 hours, and 72 hours. Thereafter, an HCV core protein contained in the culture medium was measured. Such measurement was carried out using Ortho HCV antigen IRMA test (Aoyagi et al., J. Clin. Microbiol., 37 (1999) pp. 1802-1808).

Figure 4:
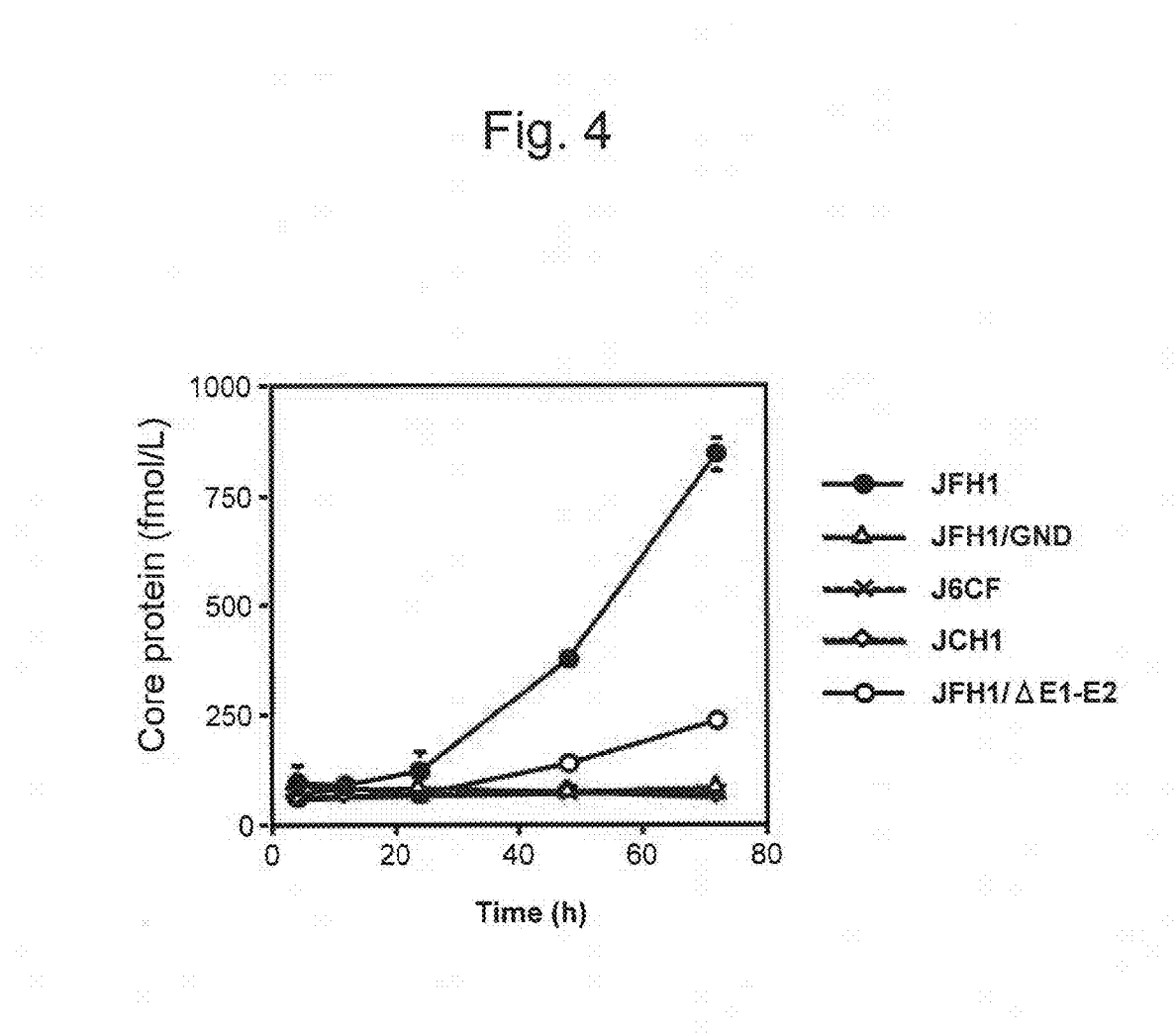

As shown in FIG. 4, a core protein was detected in the culture medium, 48 to 72 hours after the transfection with rJFH1. On the other hand, in the culture medium of the cells transfected with rJFH1/GND, rJ6CF, and rJCH1, no HCV core proteins were detected. In the culture medium of the cells transfected with rJFH1/ΔE1-E2, a small amount of HCV core protein was detected. rJFH1/GND, rJ6CF, and rJCH1 cannot autonomously replicate in Huh7 cells, whereas rJFH1 and rJFH1/ΔE1-E2 can autonomously replicate therein. Thus, it was revealed that autonomous replication of the introduced HCV RNA is essential for the release of such a core protein, and further that E1 and E2 are necessary for allowing a large amount of core protein to stably release out of the cells.

4. Detection of HCV Particles in Transfected Cell Culture Medium

In order to analyze whether or not the core protein released into the culture medium in the aforementioned example is secreted in the form of virus particles, the culture medium obtained 6 days after the transfection with rJFH1 was fractionated in a sucrose density gradient manner. That is, 2 ml of 60% (weight/weight) sucrose solution (dissolved in 50 mM Tris, pH 7.5/0.1 M NaCl/1 mM EDTA), 1 ml of 50% sucrose solution, 1 ml of 40% sucrose solution, 1 ml of 30% sucrose solution, 1 ml of 20% sucrose solution, and 1 ml of 10% sucrose solution were laminated on a centrifuge tube, and further, 4 ml of the culture supernatant of a sample was laminated thereon. This tube was then centrifuged at 400,000 RPM at 4° C. for 16 hours, using Beckmann rotor SW41Ti. After completion of the centrifugation, 0.5 ml each of fraction was recovered from the bottom of the centrifuge tube. The density, the HCV core protein concentration, and the number of HCV RNA copies were assayed for each fraction. Detection of replicon RNA by quantitative RT-PCR was carried out by detecting RNA in the 5' untranslated region of HCV RNA according to the method of Takeuchi et al. (Takeuchi T. et al., Gastroenterology 116: 636-642 (1999)). Specifically, replicon RNA contained in RNA extracted from the cells was amplified by PCR using the following synthetic primers and the EZ rTth RNA PCR kit (Applied Biosystems), and it was then detected using the ABI Prism 7700 sequence detector system (Applied Biosystems).

```
R6-130-S17:
                                    (SEQ ID NO: 6)
5'-CGGGAGAGCCATAGTGG-3'

R6-290-R19:
                                    (SEQ ID NO: 7)
5'-AGTACCACAAGGCCTTTCG-3'

TaqMan Probe, R6-148-S21FT:
                                    (SEQ ID NO: 8)
5'-CTGCGGAACCGGTGAGTACAC-3'
```

Figure 5:
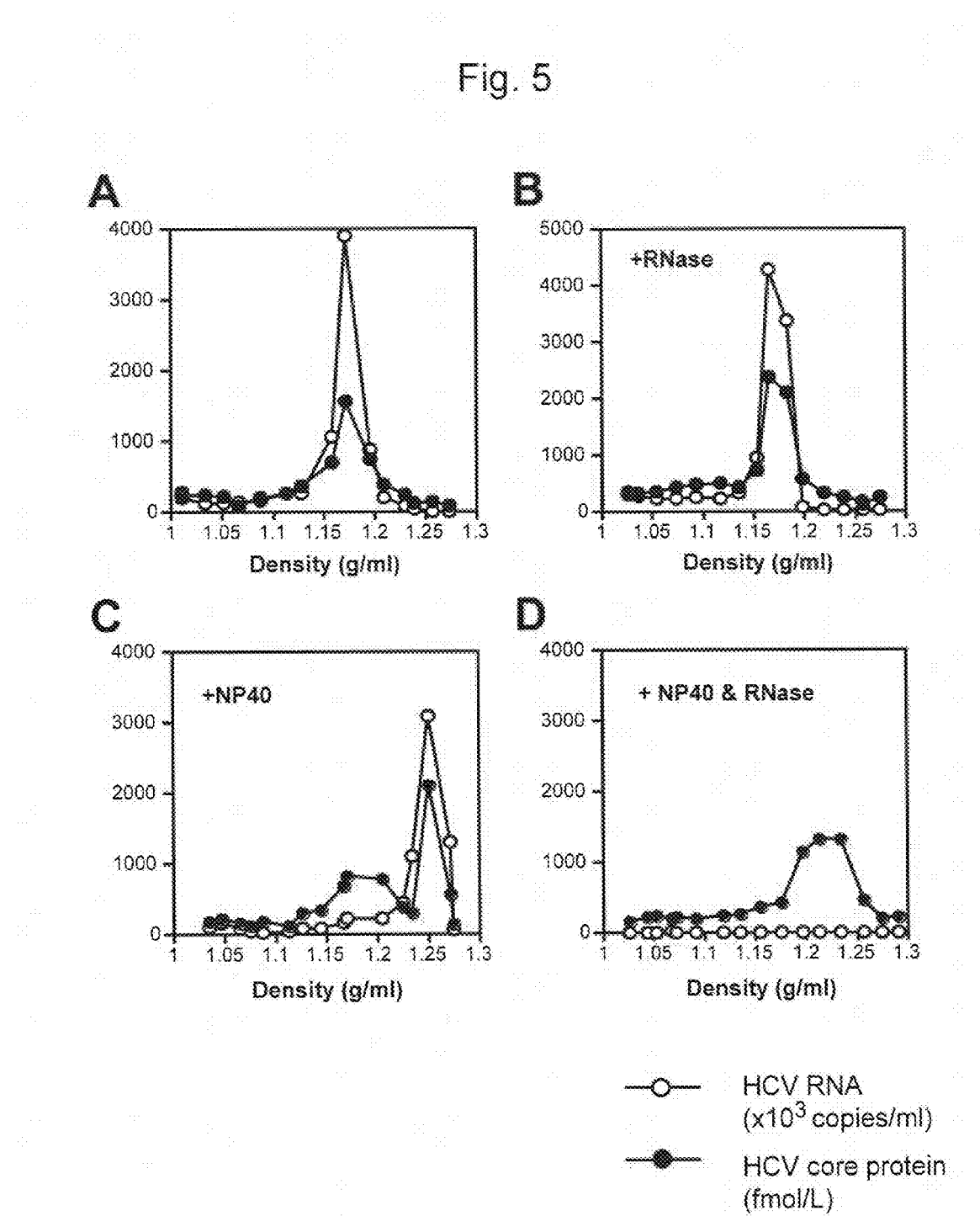

As shown in FIG. 5A, the peak of the core protein corresponded to that of HCV RNA in a fraction of 1.17 mg/ml. The density of this fraction was found to be approximately 1.17 mg/ml. This was a specific gravity lighter than that of a bound product consisting of a core protein and nucleic acid, which had previously been reported. If the core protein and HCV RNA existing in the 1.17 mg/ml fraction form HCV particles structure, it is considered that this fraction is resistant to nuclease. Hence, a culture solution obtained 6 days after the transfection with JFH1 was treated with 10 μg/ml RNAse A for 20 minutes, and it was then fractionated in a sucrose density gradient manner.

As a result, as shown in FIG. 5B, HCV RNA was decomposed, and the peak of a core protein and that of HCV RNA were detected in a fraction of 1.17 mg/ml, as in the case of being untreated with RNase A. That is to say, it was confirmed that the core protein and HCV RNA existing in the 1.17 mg/ml fraction formed HCV particles-like structure.

Thereafter, the culture solution was subjected to the same fractionation as described above, after it had been treated with 0.25% NP40. As a result, the peak of a core protein and that of HCV RNA shifted to 1.28 mg/ml (FIG. 5C). Thereafter, when the culture solution was simultaneously treated with 0.25% NP40 as well as with RNase A, the peak of HCV RNA disappeared (FIG. 5D). Thus, it was considered that a surface membrane with a low specific gravity containing lipids was exfoliated from the virus particles as a result of the treatment with NP40, so that the particles became core particles only consisting of nucleic acid and a core protein that do not have a virus-like structure, resulting in an increase in the specific gravity.

From these results, it was confirmed that virus RNA was replicated by transfection of Huh7 cells with rJFH1, and that virus particles are thereby formed and released into the culture solution.

5. Experiment Regarding Infectivity of Virus Particles in Culture Medium

Figure 6:
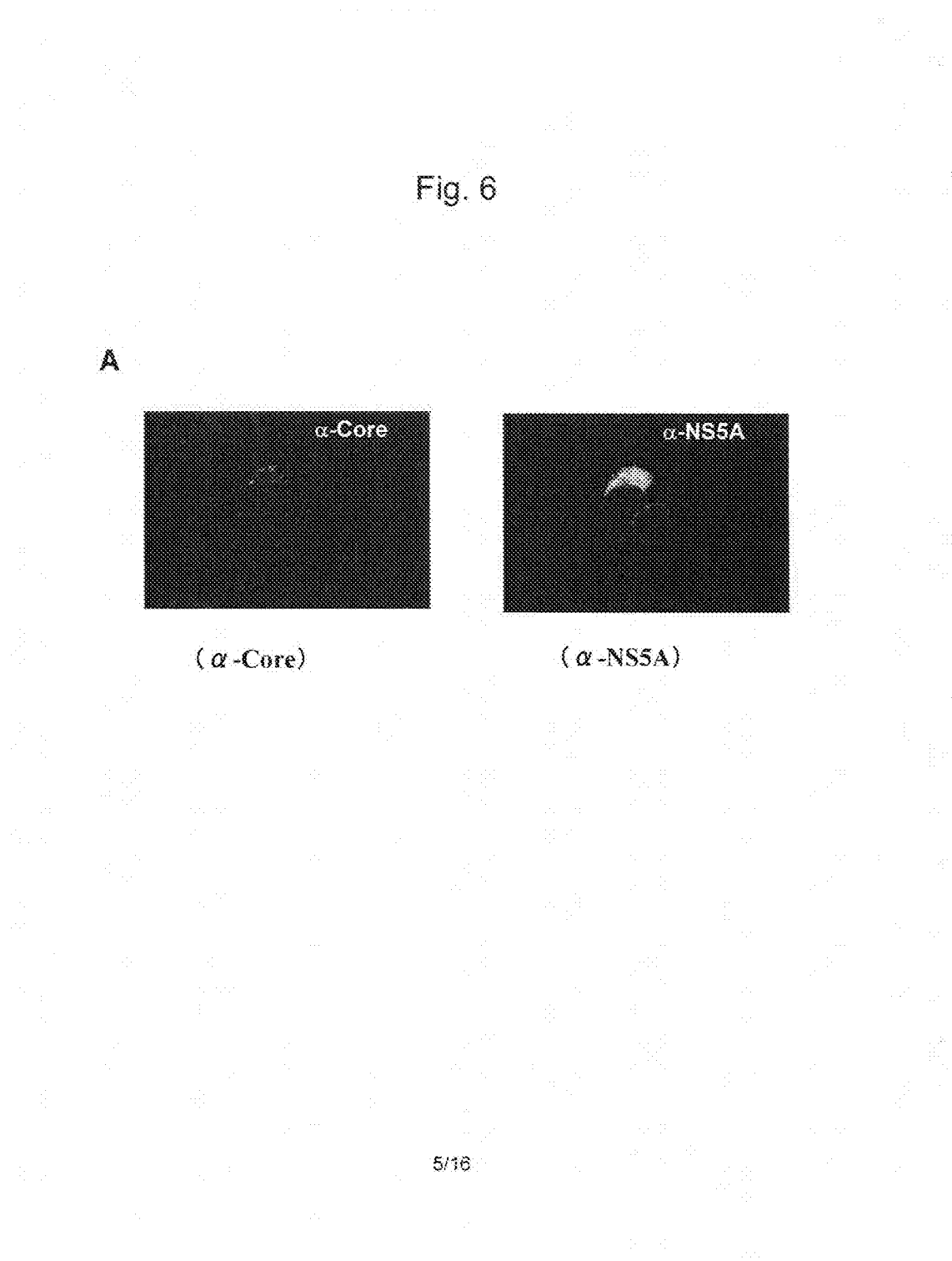

Huh7 cells were transfected with rJFH1, and the infectivity of HCV particles secreted into a culture medium was examined. The culture supernatant was recovered, 3 days after transfection of Huh7 cells with rJFH1 or rJFH1/ΔE1-E2. The recovered culture medium was centrifuged, and the centrifuged supernatant was recovered, followed by filtration through a 0.45 μm filter. In the presence of this culture medium, Huh7 cells that had not been transfected with RNA were cultured. 48 hours later, the cells were fluorescently immunostained with an anti-core antibody or an anti-NS5A antibody. As shown in FIG. 6A, in the case of the cells cultured in the presence of a culture medium obtained by transfection of Huh7 cells with rJFH1, expression of a core protein and an NS5A protein was observed in the cells. On the other hand, in the case of the cells cultured in the presence of a culture medium obtained by transfection of Huh7 cells with rJFH1/ΔE1-E2, such expression of a core protein and an NS5A protein was not observed in the cells (data not shown).

Subsequently, a culture supernatant was recovered 3 days after transfection of rHuh7 cells with JFH1, and it was then concentrated at a magnification of 30 times using an ultrafilter (cut off: 1×10$^5$ Da). Huh7 cells that had not been transfected with RNA were cultured in 100 μl of a culture medium containing the concentrated HCV particles on a 15-mm cover slip. 48 hours later, the cells were immunostained with an anti-core antibody, and the number of core antibody-stained positive cells, namely, infected cells was then counted. As a result, as shown in FIG. 6B, 394.0±26.5 infected cells were confirmed (approximately 0.51% in the total cells). Thereafter, it was confirmed whether or not this infection was caused by HCV particles that had been secreted in the culture medium as a result of the transfection of the Huh7 cells with rJFH1. That is to say, using a culture medium prepared by subjecting a culture solution used for infection to UV treatment, and another culture medium prepared without the step of transfection with RNA, Huh7 cells that had not been transfected with RNA were cultured on a 15-mm cover slip. 48 hours later, the cells were immunostained with an anti-core antibody, and the number of infected cells was then counted.

As a result, in the case where the cells were treated with UV, the number of infected cells was drastically decreased. In the case of culture medium prepared without the step of transfection with RNA, no infected cells were observed.

Moreover, it was examined whether or not the infectious HCV particles amplify RNA in the cells and then release new HCV particles into the culture medium. Huh7 cells that had not been transfected with RNA were cultured in 100 µl of a culture medium containing HCV particles prepared by concentration of a culture medium obtained 48 hours after transfection of Huh7 cells with rJFH1. Thereafter, cells and a culture medium were recovered per day, and RNA was recovered therefrom. The amount of HCV RNA was assayed by the aforementioned method. As a result, as shown in FIG. 6C, HCV RNA amplified to a certain amount in the cells, and the amount of HCV RNA increased with time dependent manner in the supernatant. On the other hand, the same examination was carried out using a culture solution obtained by transfection of Huh7 cells with rJFH1/ΔE1-E2. However, no HCV RNA was detected in the cells and in the culture solution.

From these results, it was confirmed that HCV particles secreted into the culture medium have infectivity as a result of the transfection of Huh7 cells with rJFH1 and also has ability to amplify HCV RNA in the infected cells and to produce new HCV particles.

6. Production of HCV Virus Particles Using rJCH1/NS5B (jfh1)

Figure 7:
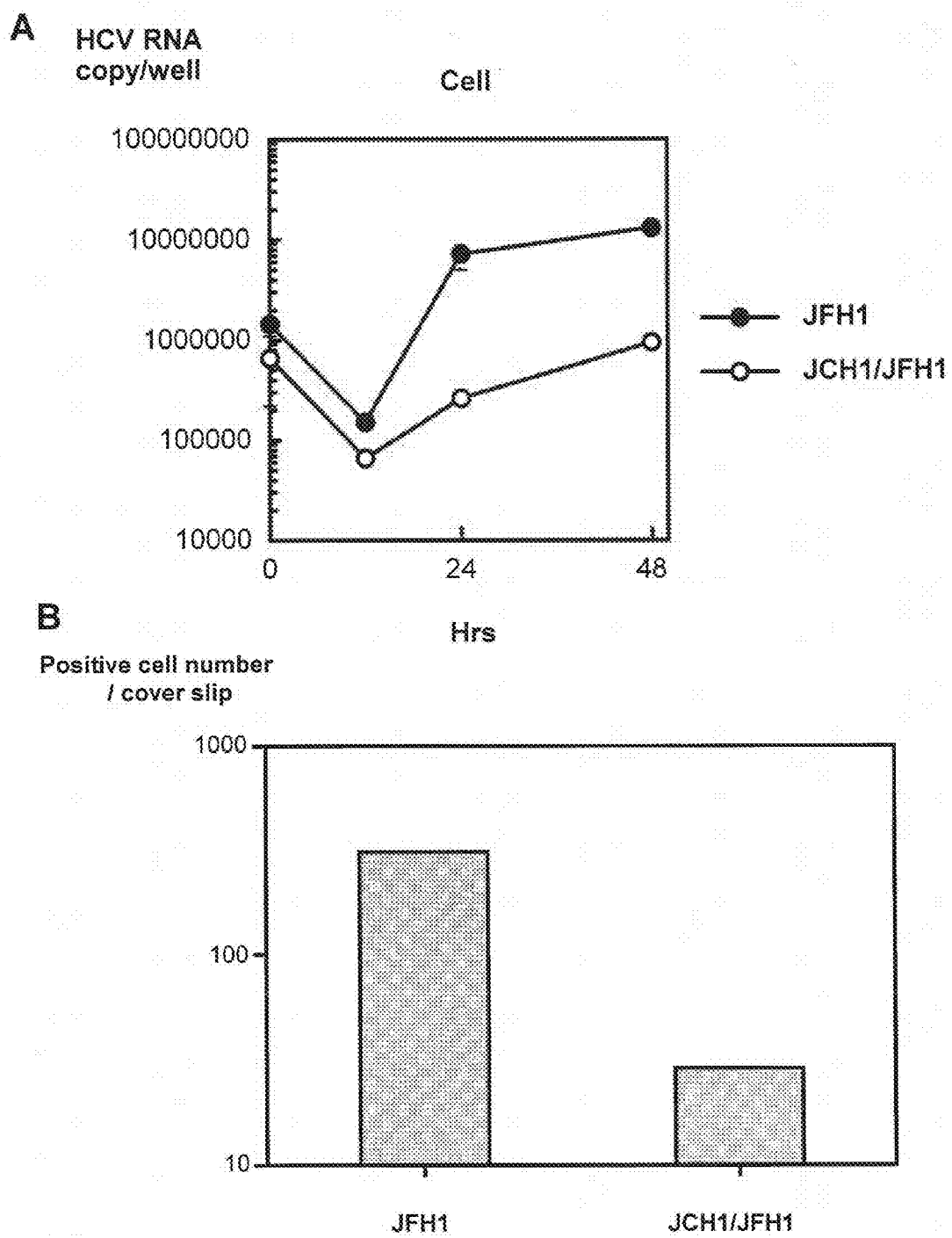
Figure 8:
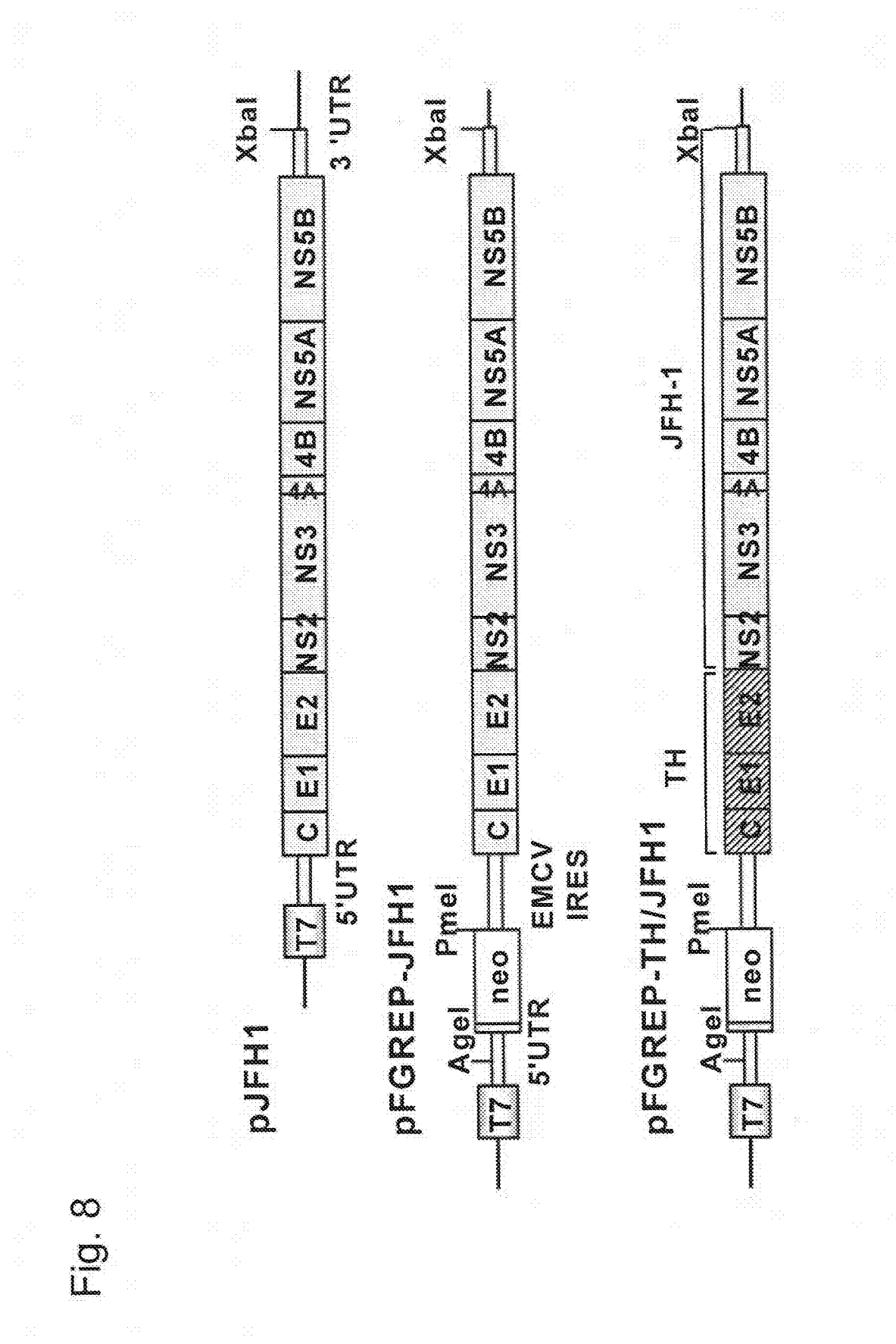
Figure 10:
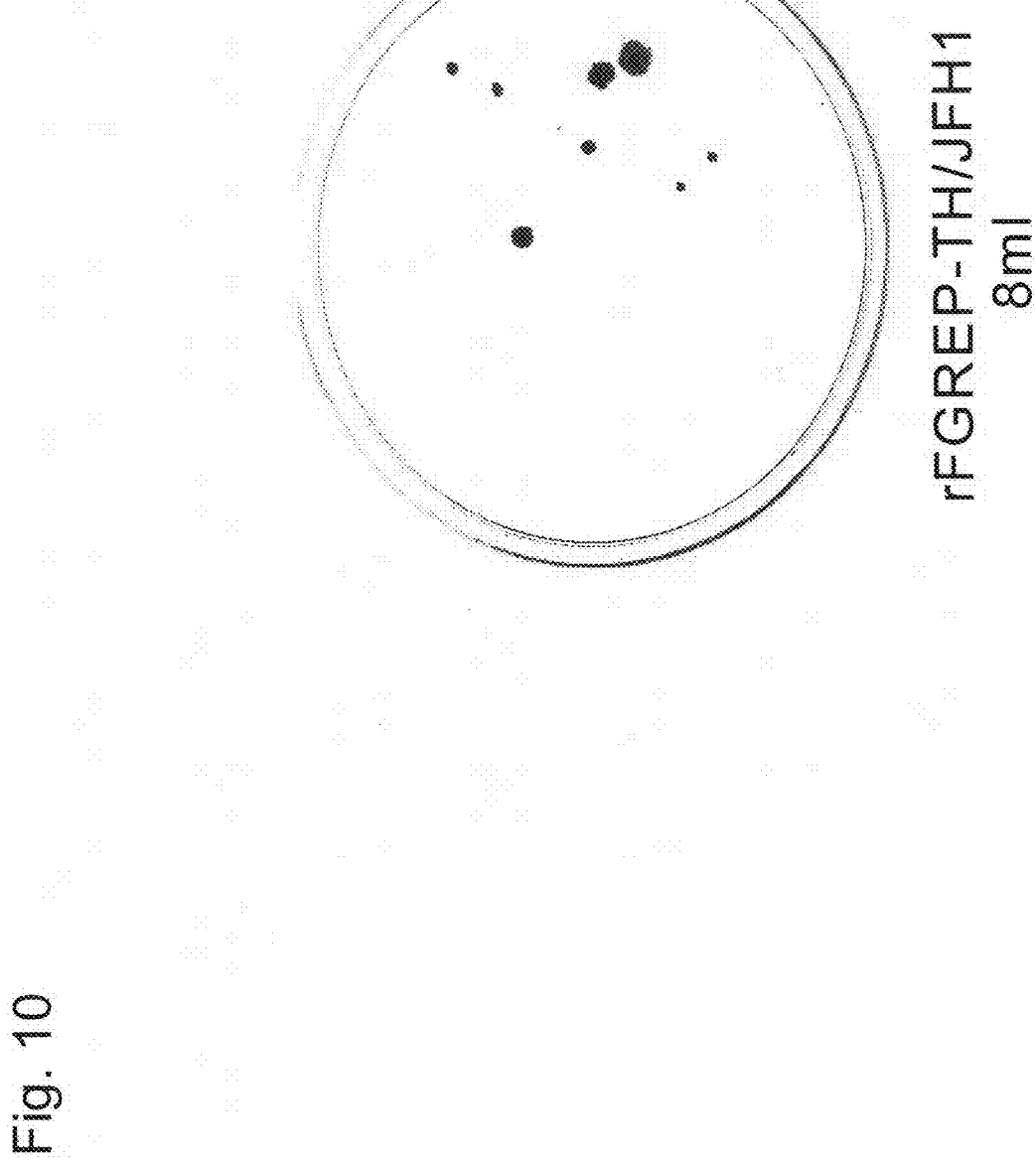
FIG. 10 shows the results regarding formation of colonies by infection with TH/JFH1 chimeric replicon culture supernatant.

It was examined whether or not HCV particles are secreted into a culture medium as a result of transfection of Huh7 cells with rJCH1/NS5B(jfh1), or whether or not the secreted HCV particles have infectivity. A culture solution obtained 6 days after transfection of Huh7 cells with rJCH1/NS5B(jfh1) was concentrated by the method described in section 5 above. In the presence of this culture medium, Huh7 cells that had not been transfected with RNA were cultured, and time dependent changes of the amount of HCV RNA in the cells were assayed. From 12 hours after initiation of the culture, the amount of HCV RNA in the cells increased with time dependent manner (FIG. 7A). Moreover, Huh7 cells, which had not been transfected with RNA, were cultured on a 15-mm cover slip, and the cells were then cultured in the presence of the concentrated culture medium. 48 hours later, the cells were immunostained with an anti-core antibody, and the number of core antibody-stained positive cells, namely, infected cells was then counted. As a result, as shown in FIG. 7B, infected cells were observed. From these results, it was revealed that HCV particles secreted into a culture medium acquire infectivity as a result of the transfection of Huh7 cells with rJCH1/NS5B(jfh1) and also has ability to amplify HCV RNA in the infected cells and to produce new HCV particles.

Accordingly, even in the case of a strain that cannot be autonomously replicated in vitro, such as an HCV strain isolated from patients, substitution of the HS5B region thereof with rJFH1 NS5B enables autonomous replication thereof in a culture cell system and generation of HCV particles.

Example 3

1. Production of HCV Virus Particles Using Con1/C-NS2/JFH-1

Huh7 cells were transfected with chimeric HCV RNA comprising the NS5B portion of a Con-1 strain with HCV genotype 1b and that of JFH-1, and then, it was examined whether or not HCV particles are secreted into a culture solution, and whether or not the secreted HCV particles have infectivity.

The sequence of a Con-1 strain with HCV genotype 1b corresponding to 1 to 1,026 (the core, E1, E2, p7, and NS2 regions of the Con1 strain) was ligated downstream of the 5'-UTR of a JFH-1 strain. Thereafter, the 1,031-3,030 region of the JFH-1 strain (from NS3 to NS5b) was further ligated downstream thereof. Thereafter, the 3'-UTR of the JFH-1 strain was further ligated downstream thereof, so as to produce a construct. Using this construct, rCon1/C-NS2/JFH-1 chimeric HCV RNA was produced by the method described in Example 1-2 above. Thereafter, Huh7 cells were transfected with the above RNA by the method described in Example 2-1 above. Huh7 cells were transfected with HCV RNA, and a core protein contained in a supernatant was measured over time. From approximately 48 hours onward, such a core protein was detected in the supernatant, and thus it could be confirmed that HCV particles were generated in the cell supernatant. Subsequently, the supernatant was concentrated at a magnification of 20 times by ultrafiltration, and the concentrate was then added to Huh7 cells. 48 hours after the culture, the cells were stained with a rabbit anti-NS3 antibody.

As a result, no anti-NS3 antibody positive cells were observed in mock and rJFH-1/ΔEE1-E2, but such anti-NS3 antibody positive cells were detected in rJFH-1 and rCon1/C-NS2/JFH-1. From these results, it could be confirmed that rCon1/C-NS2/JFH-1 can generate infectious HCV particles, as with JFH-1.

Example 4

Production of Full-Length Chimeric HCV Replicon RNA Derived From Full-Length Chimeric HCV Genomic RNA (1) Construction of Expression Vector DNA (JFH-1 clone: SEQ ID NO: 9) containing the full-length genomic cDNA of a JFH-1 strain (genotype 2a), which is a hepatitis C virus isolated from patients suffering from fulminant hepatitis, was inserted downstream of a T7 RNA promoter sequence in a pUC19 plasmid, so as to produce plasmid DNA.

Specifically, an RT-PCR fragment obtained by amplification of the virus RNA of the JFH-1 strain was cloned into a pGEM-T EASY vector (Promega), so as to obtain various plasmid DNA such as pGEM1-258, pGEM44-486, pGEM317-849, pGEM617-1323, pGEM1141-2367, pGEM2285-3509, pGEM3471-4665, pGEM4547-5970, pGEM5883-7003, pGEM6950-8035, pGEM7984-8892, pGEM8680-9283, pGEM9231-9634, and pGEM9594-9678 (Kato et al., Gastroenterology, (2003) 125: pp. 1808-1817). The virus genomic RNA-derived cDNA contained in each plasmid was ligated to one another by the PCR method and the use of restriction enzymes, and thus the full-length genomic cDNA was cloned. A T7 RNA promoter sequence was inserted upstream of the full-length virus genome. Hereinafter, the thus constructed plasmid DNA is referred to as pJFH1. It is to be noted that production of the aforementioned JFH-1 clone is described in JP Patent Publication (Kokai) No. 2002-171978 A and the document of Kato et al. (Kato et al., J. Med. Virol., (2001) 64(3): pp. 334-339). In addition, the nucleotide sequence of the full-length cDNA of the JFH-1 clone has been registered with International DNA Databank (DDBJ/EMBL/GenBank) under Accession No. AB047639.

Subsequently, EMCV-IRES (the internal ribosome entry site for encephalomyocarditis virus) and a neomycin resistance gene (neo; also referred to as a neomycin phosphotransferase gene) were inserted between the 5' untranslated region and core region of pJFH1, which was plasmid DNA, so as to construct pFGREP-JFHL which was plasmid DNA. Such construction was carried out in accordance with the procedures of Ikeda et al. (Ikeda et al., J. Virol., (2002) 76(6): pp. 2997-3006).

(2) Construction of Chimeric Expression Vector

The JFH1 strain is HCV derived from HCV with type 2a. A TH strain derived from HCV with type 1b (Wakita et al., J. Biol. Chem., (1994) 269, pp. 14205-14210; and Moradpour et al., Biochem. Biophys. Res. Commun., (1998) 246, pp. 920-924) was used, so as to produce a chimeric HCV vector. The core, E1, E2, and p7 portions of the pFGREP-JFH1 as produced above were substituted with those of the TH strain, so as to produce chimeric HCV, pFGREP-TH/JFH1.

In the present specification, the full-length RNA sequence of the aforementioned JFH1 strain (derived from a JFH-1 clone), and the partial RNA sequence of the TH strain used for producing the above chimeric body (partial genomic RNA (1-3748) comprising a portion corresponding to the region from the 5' untranslated region of the HCV TH strain to the NS3 region thereof), are shown in SEQ ID NOS: 9 and 10, respectively. In the aforementioned full-length genomic RNA sequence of the JFH-1 strain (SEQ ID NO: 9), the "5' untranslated region" corresponds to 1-340, the "core protein coding sequence" corresponds to 341-913, the "E1 protein coding sequence" corresponds to 914-1489, the "E2 protein coding sequence" corresponds to 1490-2590, the "NS2 protein coding sequence" corresponds to 2780-3430, the "NS3 protein coding sequence" corresponds to 3431-5323, the "NS4A protein coding sequence" corresponds to 5324-5486, the "NS4B protein coding sequence" corresponds to 5487-6268, the "NS5A protein coding sequence" corresponds to 6269-7663, and the "NS5B protein coding sequence" corresponds to 7664-9442.

(3) Production of Full-Length Chimeric HCV Replicon RNA

In order to produce template DNA used for the synthesis of full-length chimeric HCV replicon RNA, the expression vector pFGREP-TH/JFH1 as constructed above was cleaved with the restriction enzyme XbaI. Thereafter, 10 to 20 μg of the XbaI cleavage fragment was mixed into 50 μl of a reaction solution, and the obtained mixture was incubated with Mung Bean Nuclease 20 U at 30° C. for 30 minutes. Mung Bean Nuclease is an enzyme that catalyzes a reaction of selectively digesting a single-stranded portion in double-stranded DNA. In general, when RNA is synthesized directly using the aforementioned XbaI cleavage fragment as a template, replicon RNA, to the 3'-terminus of which 4 nucleotides CUAG that constitute a part of an XbaI recognition sequence are redundantly added, is synthesized. Thus, in the present example, such an XbaI cleavage fragment was treated with Mung Bean NuClease, so as to eliminate the 4 nucleotides CTAG from the XbaI fragment. Thereafter, the thus Mung Bean Nuclease-treated solution containing the XbaI cleavage fragment was subjected to a protein elimination treatment according to common methods, so that the XbaI cleavage fragment, from which the 4 nucleotides CTAG had been eliminated, was purified. The purified fragment was used as template DNA.

Subsequently, RNA was synthesized from the template DNA in vitro using T7 RNA polymerase. MEGAscript manufactured by Ambion was used for such RNA synthesis. 20 μl of a reaction solution containing 0.5 to 1.0 μg of the template DNA was allowed to react in accordance with instructions provided from manufacturer.

After completion of the synthesis of RNA, DNase (2 U) was added to the reaction solution, and the obtained mixture was reacted at 37° C. for 15 minutes. Thereafter, RNA was extracted with acidic phenol, and the template DNA was eliminated. Thus, RNA synthesized from the aforementioned template DNA derived from pFGREP-TH/JFH1 was named as rFGREP-TH/JFH1. The nucleotide sequence of chimeric HCV genomic RNA in the rFGREP-TH/JFH is shown in SEQ ID NO: 11. Such rFGREP-TH/JFH is an example of the full-length chimeric HCV replicon RNA of the present invention.

Example 5

Production of Full-Length Chimeric HCV Replicon RNA-Replicating Cells and Establishment of Cell Clone (1) Introduction of Full-Length Chimeric HCV Genomic RNA into Cells Different amounts of the full-length chimeric HCV genomic RNA (rFGREP-TH/JFH1) as synthesized above were mixed with total cellular RNA extracted from Huh7 cells, resulting in the total amount of RNA of 10 μg. Subsequently, the mixed RNA was introduced into Huh7 cells by the electroporation method. After the cells had been cultured for 16 to 24 hours, G418 was added thereto at different amounts. The culture was continued while the culture solution was exchanged with a fresh one, twice a week. After completion of the culture for 21 days, surviving cells were stained with crystal violet. The number of the stained colonies was counted, and the number of colonies obtained per weight of RNA used for transfection was then calculated. In addition, in several culture dishes, the colonies of surviving cells were cloned, and the culture was continued. RNA, genomic DNA, and a protein were extracted from the cloned cells, and thereafter, detection of full-length chimeric HCV replicon RNA, the presence or absence of incorporation of a neomycin resistance gene into genomic DNA, and expression of an HCV protein were examined. The results are shown in detail below.

(2) Colony Formation Ability

As a result of the aforementioned transfection, colony formation by cells was observed even in a case where the G418 concentration was 1.0 mg/ml. It was considered that rFGREP-TH/JFH1 replicon RNA autonomously replicated in Huh7 cells transfected with the rFGREP-TH/JFH1 replicon RNA, and that a neomycin resistance gene was persistently expressed, so that G418 resistance was maintained. Thus, the cells were able to grow, and the Huh7 cells acquired colony formation ability.

Example 6

Infectivity of Chimeric HCV Virus in Culture Supernatant

Experiment Regarding Infectivity of Chimeric HCV Virus Particles in Culture Supernatant Huh7 cells were transfected with rFGREP-TH/JFH1, and a culture supernatant containing the established full-length chimeric HCV replicon RNA-replicating cell clones was then recovered. The culture supernatant was added to Huh7 cells that had not been infected, so that the Huh7 cells were infected with virus particles in the culture supernatant. On the day following infection, 0.3 mg/ml G418 was added to the culture medium containing the infected Huh7 cells, and the mixture was further cultured for 21 days. After completion of the culture, the cells were fixed and then strained with crystal violet. As a result, colony formation was observed in the cells infected with the culture supernatant containing the full-length chimeric HCV replicon RNA-replicating cell clones obtained by transfection with rFGREP-TH/JFH1. This shows that the full-length chimeric HCV replicon RNA-replicating cell clones obtained by transfection with rFGREP-TH/JFH1 generate infectious HCV, and also that the HCV has infectivity to new cells.

Example 7

Purification of HCV Particles (1) Gel Filtration

FIG. 11 shows distribution of HCV particles in each fraction by gel filtration chromatography. The used gel carriers were Sephacryl® S300, S400, and S500. A solution containing HCV particles used for column chromatography was purified using column chromatography containing each of the above gel carriers. A buffer used for purification comprised 10 mM Tris-hydrochloride, 1 mM ethylenediaminetetraacetic acid, and 100 mM sodium chloride (pH 8.0). As a result, in the case of using Sephacryl® S-300, HCV particles were obtained at a passing fraction called Void fraction. Thus, using Sephacryl® S-300, HCV particles were separated from proteins with small molecular weights, so that the salt concentration of the solution could be changed. The ratio of the HCV core protein to the total protein mass was 3.78 when compared with the HCV particles before column purification, and thus, the ratio of the HCV particles to the total protein increased. On the other hand, in the case of using Sephacryl® S-400 and S-500, since HCV particles were obtained at a fraction eluted depending on molecular weight, the particles can be separated from other proteins with different molecular weights.

(2) Ion Exchange Chromatography

FIG. 12 shows distribution of HCV particles in each fraction by ion exchange chromatography. The used gel carriers were SP Sepharose HP® and Q Sepharose HP®.

In the case of a column using SP Sepharose HP®, the column was equilibrated with a 50 mM citric acid buffer (pH 6.2). A solution containing HCV particles, which had been concentrated using an ultrafilter with a fractional molecular weight between 100,000 and 500,000 and then diluted with a 50 mM citric acid buffer (pH 6.2), was added to the column. Thereafter, a 50 mM citric acid buffer (pH 6.2) was passed through the column, at a volume approximately 10 times larger than that of the column. Subsequently, 50 mM citric acid buffers (pH 6.2), to which each of 0.1 M NaCl, 0.3 M NaCl, and 1 M NaCl had been added, were successively passed through the column, at a volume approximately 3 times larger than that of the column. Thereafter, a 50 mM citric acid buffer (pH 6.2), to which 1 M NaCl had been added, was passed through the column, at a volume approximately 5 times larger than that of the column (1 M NaClW fraction). As a result, HCV particles were eluted in the fraction of the 50 mM citric acid buffer (pH 6.2), to which 0.1 M NaCl had been added.

In the case of a column using Q Sepharose HP®, the column was equilibrated with a 50 mM Tris-HCl buffer (pH 8.0). A solution containing HCV particles, which had been concentrated using an ultrafilter with a fractional molecular weight between 100,000 and 500,000 and then diluted with a 50 mM Tris-HCl buffer (pH 8.0), was added to the column. Thereafter, a 50 mM Tris-HCl buffer (pH 8.0) was passed through the column, at a volume approximately 10 times larger than that of the column. Subsequently, 50 mM Tris-HCl buffers (pH 8.0), to which each of 0.1 M NaCl, 0.3 M NaCl, and 1 M NaCl had been added, were successively passed through the column, at a volume approximately 3 times larger than that of the column. Thereafter, a 50 mM Tris-HCl buffer (pH 8.0), to which 1 M NaCl had been added, was passed through the column, at a volume approximately 5 times larger than that of the column (1 M NaClW fraction). As a result, HCV particles were eluted in the fraction of the 50 mM Tris-HCl buffer (pH 8.0), to which 0.3 M NaCl had been added. The ratio of the HCV core protein to the total protein mass was 2.32 when compared with the HCV particles before column purification, and thus, the ratio of the HCV particles to the total protein increased.

(3) Affinity Chromatography

FIG. 13 shows distribution of HCV particles in each fraction by lectin affinity chromatography. In the affinity chromatography, carriers, to which each of RCA-120, ConA, LCA, and WGA binds, were used.

In the case of ConA, LCA, and WGA affinity chromatography, the column was equilibrated with a phosphate buffered saline. A solution containing HCV particles, which had been concentrated using an ultrafilter with a molecular weight cut-off between 100,000 and 500,000 and then diluted with a phosphate buffered saline, was added to the column. Thereafter, a phosphate buffered saline was passed through the column, at a volume approximately 10 times larger than that of the column. Subsequently, a phosphate buffered saline, to which 0.35 M lactose had been added, was passed through the column, at a volume approximately 3 times larger than that of the column. Thereafter, a phosphate buffered saline, to which 0.5 M lactose had been added, was passed through the column, at a volume approximately 5 times larger than that of the column. As a result, in the case of LCA and ConA affinity chromatography, no specific binding to the carrier was observed. In the case of WGA affinity chromatography, HCV particles were eluted in the fraction of the phosphate buffered saline, to which 0.35 M lactose had been added.

In the case of RCA-120 affinity chromatography, the column was equilibrated with a phosphate buffered saline. A solution containing HCV particles, which had been concentrated using an ultrafilter with a fractional molecular weight between 100,000 and 500,000 and then diluted with a phosphate buffered saline, was added to the column. Thereafter, a phosphate buffered saline was passed through the column, at a volume approximately 10 times larger than that of the column. Subsequently, a phosphate buffered saline, to which 0.38 M lactose had been added, was passed through the column, at a volume approximately 3 times larger than that of the column. Thereafter, a phosphate buffered saline, to which 0.38 M lactose had been added, was passed through the column, at a volume approximately 5 times larger than that of the column. As a result, in the case of RCA-120 affinity chromatography, HCV particles were eluted in the fraction of the phosphate buffered saline, to which 0.38 M lactose had been added.

FIG. 14 shows distribution of HCV particles in each fraction by heparin and sulfated cellulofine affinity chromatography.

In each affinity chromatography, the column was equilibrated with a 20 mM phosphate buffer (pH 7.0). A solution containing HCV particles, which had been concentrated using an ultrafilter with a molecular weight cut-off between 100,000 and 500,000 and then diluted with a 20 mM phosphate buffer (pH 7.0), was added to the column. Thereafter, a phosphate buffer (pH 7.0) was passed through the column, at a volume approximately 10 times larger than that of the column. Subsequently, phosphate buffers (pH 7.0), to which any one of 0.1 M, 0.3 M, 0.5 M, and 1 M NaCl had been added, were successively passed through the column, at a volume approximately 3 times larger than that of the column. Thereafter, a 20 mM phosphate buffer (pH 7.0), to which 1 M NaCl had been added, was passed through the column, at a volume approximately 5 times larger than that of the column. As a result, in the case of heparin affinity chromatography, HCV particles were eluted in the fraction of the 20 mM phosphate buffer (pH 7.0), to which 0.3 M NaCl had been added. The ratio of the HCV core protein to the total protein mass was 0.36 when compared with the HCV particles before column purification, and thus, the ratio of the HCV particles to the total protein decreased. In the case of sulfated cellulofine affinity chromatography, HCV particles were eluted in the fraction of the 20 mM phosphate buffer (pH 7.0), to which 0.1 M NaCl had been added.

FIG. 15 shows distribution of HCV particles in each fraction by blue dye affinity chromatography.

In blue dye affinity chromatography, a carrier obtained by binding Cibacron Blue F3G-A to agarose particles was used for the column. The column was equilibrated with a 20 mM phosphate buffer (pH 7.0). A solution containing HCV particles, which had been concentrated using an ultrafilter with a molecular weight cut-off between 100,000 and 500,000 and then diluted with a 20 mM phosphate buffer (pH 7.0), was added to the column. Thereafter, a phosphate buffered saline was passed through the column, at a volume approximately 10 times larger than that of the column. Subsequently, 20 mM phosphate buffers (pH 7.0), to which either 1 M or 2 M NaCl had been added, were successively passed through the column, at a volume approximately 3 times larger than that of the column. Thereafter, a 20 mM phosphate buffer (pH 7.0), to which 2 M NaCl had been added, was passed through the column, at a volume approximately 5 times larger than that of the column. As a result, HCV particles were eluted in a column nonbonding fraction. The ratio of the HCV core protein to the total protein mass was 3.33 when compared with the HCV particles before column purification, and thus, the ratio of the HCV particles to the total protein increased.

(4) Sucrose Density Gradient Centrifugation

HCV particles were purified by the combined use of column chromatography with sucrose density gradient centrifugation, with reference to the aforementioned examples.

First, HCV particles were purified using Q Sepharose HP®. The column was equilibrated with a 50 mM Tris-HCl buffer (pH 8.0). A solution containing HCV particles, which had been concentrated using an ultrafilter with a fractional molecular weight between 100,000 and 500,000 and then diluted with a 50 mM Tris-HCl buffer (pH 8.0), was added to the column. Thereafter, a 50 mM Tris-HCl buffer (pH 8.0) was passed through the column, at a volume approximately 10 times larger than that of the column. Subsequently, 50 mM Tris-HCl buffer (pH 8.0), to which each of 0.1 M NaCl, 0.3 M NaCl, and 1 M NaCl had been added, were successively passed through the column, at a volume approximately 3 times larger than that of the column. Thereafter, a 50 mM Tris-HCl buffer (pH 8.0), to which 1 M NaCl had been added, was passed through the column, at a volume approximately 5 times larger than that of the column (1 M NaClW fraction). As a result, as shown in FIG. 16A, HCV particles were eluted in the fraction of the 50 mM Tris-HCl buffer (pH 8.0), to which 0.3 M NaCl had been added; the fraction of the 50 mM Tris-HCl buffer (pH 8.0), to which 1 M NaCl had been added; and the 1 M NaClW fraction. Fractions containing HCV particles were collected. The ratio of the HCV core protein to the total protein mass was 2.29 when compared with the HCV particles before column purification, and thus, the ratio of the HCV particles to the total protein increased.

Second, HCV particles were purified by sulfated cellulofine chromatography. In each chromatography, the column was equilibrated with a 20 mM phosphate buffer (pH 7.0). A solution containing HCV particles obtained by concentrating using an ultrafilter with a molecular weight cut-off between 100,000 and 500,000, the fractions containing HCV particles purified with Q Sepharose HP®, and then diluting the resultant with a 20 mM phosphate buffer (pH 7.0), was added to the column. Thereafter, a phosphate buffer (pH 7.0) was passed through the column, at a volume approximately 10 times larger than that of the column. Subsequently, 20 mM phosphate buffers (pH 7.0), to which either 0.25 M or 1 M NaCl had been added, were successively passed through the column, at a volume approximately 3 times larger than that of the column. Thereafter, a 20 mM phosphate buffer (pH 7.0), to which 1 M NaCl had been added, was passed through the column, at a volume approximately 5 times larger than that of the column. As a result, as shown in FIG. 16B, HCV particles were mainly eluted in 20 mM phosphate buffer (pH 7.0), to which 1 M NaCl had been added. The ratio of the HCV core protein to the total protein mass in the 20 mM phosphate buffer (pH 7.0), to which 1 M NaCl had been added, was 31.4 when compared with the HCV particles before column purification. Thus, the ratio of the HCV particles to the total protein increased.

Further, HCV particles were purified by sucrose density gradient centrifugation. The fraction of the 20 mM phosphate buffer (pH 7.0), to which 1 M NaCl had been added by sulfated cellulofine chromatography, was concentrated using an ultrafilter with a molecular weight cut-off between 100,000 and 500,000, and then diluted with a TEN buffer (10 mM Tris-HCl buffer (pH 8.0), 0.1 M sodium chloride, and 1 mM ethylenediaminetetraacetic acid (pH 8.0)). A solution containing HCV particles was laminated on a solution obtained by lamination of 60%, 50%, 40%, 30%, 20%, and 10% sucrose solutions, and the obtained solution was centrifuged at 390 k×g for 18 hours at 4° C. Since the HCV particles were gathered to a fraction with a specific gravity of approximately 1.2, the fraction was collected. The ratio of the HCV core protein to the total protein mass in the collected fraction was 1.69 when compared with the HCV particles before column purification. Thus, the ratio of the HCV particles to the total protein increased.

In the fraction containing HCV particles purified by sucrose density gradient centrifugation, the ratio of the HCV core protein to the total protein mass was approximately 120 times purified, when compared with that before initiation of column chromatography. The final fraction contained $10^9$ copies/ml HCV particles.

All publications, patents and patent applications cited herein are incorporated herein by reference in their entirety.

INDUSTRIAL APPLICABILITY

The present invention enables production of HCV virus particles with various genotypes in a cultured cell system. That is to say, even in the case of an HCV strain that cannot be autonomously replicated in vitro, such as HCV strains isolated from patients, the RNA sequence portion thereof encoding NS3, NS4, NS5A, and NS5B proteins is substituted with an RNA sequence portion encoding the NS3, NS4, NS5A, and NS5B proteins of JFH1, so that the above HSV strain can be autonomously replicated in a cultured cell system, thereby producing HCV particles. The HCV particles purified by the present invention can be directly used as a vaccine for medical use. The HCV genomic RNA or virus particles provided by the present invention can also be used as a virus vector for a foreign gene. Moreover, the method of the present invention can also be used for studies regarding an HCV infection process, or for production of a screening system for various substances that affect such an HCV infection process.

Sequence Listing Free Text

SEQ ID NO: 1 sequence encoding NS3 to NS5 proteins of JFH1 (cDNA sequence)
SEQ ID NO: 2 sequence encoding NS5B proteins of JFH1 (cDNA sequence)
SEQ ID NO: 3 NS5B protein of JFH1
SEQ ID NO: 4 Synthetic peptide designed based on JFH1 E2 fragment
SEQ ID NO: 5 Synthetic peptide designed based on JFH1 E2
SEQ ID NO: 6 Primer (R6-130-517)
SEQ ID NO: 7 Primer (R6-290-R19)
SEQ ID NO: 8 TaqMan probe (R6-148-S21FT)
SEQ ID NO: 9 full-length Hepatitis C virus genomic RNA derived from JFH1 strain (JFH-1 clone)
SEQ ID NO: 10 genomic RNA sequence comprising 5' UTR to NS3 region of TH1 strain
SEQ ID NO: 11 Chimera Hepatitis C virus genomic RNA derived from HCV JFH1 strain(JFH-1 clone) and HCV TH strain

SEQUENCE LISTING

```
<160> NUMBER OF SEQ ID NOS: 11

<210> SEQ ID NO 1
<211> LENGTH: 6012
<212> TYPE: DNA
<213> ORGANISM: Hepatitis C virus
<220> FEATURE:
<221> NAME/KEY: misc_feature
<222> LOCATION: (1)..(6012)
<223> OTHER INFORMATION: sequence encoding NS3 to NS5 proteins of JFH1
      (cDNA sequence)

<400> SEQUENCE: 1
gctcccatca ctgcttatgc ccagcaaaca cgaggcctcc tgggcgccat agtggtgagt      60 atgacgggc gtgacaggac agaacaggcc ggggaagtcc aaatcctgtc cacagtctct     120
cagtccttcc tcggaacaac catctcgggg gttttgtgga ctgtttacca cggagctggc     180
aacaagactc tagccggctt acggggtccg gtcacgcaga tgtactcgag tgctgagggg     240
gacttggtag gctggcccag ccccctggg accaagtctt tggagccgtg caagtgtgga     300
gccgtcgacc tatatctggt cacgcggaac gctgatgtca tcccggctcg gagacgcggg     360
gacaagcggg gagcattgct ctccccgaga cccatttcga ccttgaaggg gtcctcgggg     420
gggccggtgc tctgccctag gggccacgtc gttgggctct tccgagcagc tgtgtgctct     480
cggggcgtgg ccaaatccat cgatttcatc ccgttgaaga cactcgacgt tgttacaagg     540
tctcccactt tcagtgacaa cagcacgcca ccggctgtgc cccagaccta tcaggtcggg     600
tacttgcatg ctccaactgg cagtggaaag agcaccaagg tccctgtcgc gtatgccgcc     660 cagggtaca aagtactagt gcttaacccc tcggtagctg ccaccctggg gtttggggcg     720
tacctatcca aggcacatgg catcaatccc aacattagga ctggagtcag gaccgtgatg     780
accggggagg ccatcacgta ctccacatat ggcaaatttc tcgccgatgg gggctgcgct     840
agcggcgcct atgacatcat catatgcgat gaatgccacg ctgtggatgc taccttccatt     900 ctcggcatcg gaacggtcct tgatcaagca gagacagccg gggtcagact aactgtgctg     960
gctacggcca caccccccgg gtcagtgaca accccccatc ccgatataga agaggtaggc     1020
ctcgggcggg agggtgagat cccccttctat ggagggcga ttccctatc ctgcatcaag     1080 ggagggagac acctgatttt ctgccactca agaaaaagt gtgacgagct cgcggcggcc     1140
cttcggggca tgggcttgaa tgccgtgca ctatatagag gttggacgt ctccataata     1200 ccagctcagg gagatgtggt ggtcgtcgcc accgacgccc tcatgacggg gtacactgga     1260
gactttgact ccgtgatcga ctgcaatgta gcggtcaccc aagctgtcga cttcagcctg     1320
gaccccacct tcactataac cacacagact gtcccacaag acgctgtctc acgcagtcag     1380
cgccgcgggc gcacaggtag aggaagacag ggcacttata ggtatgtttc cactggtgaa     1440
```

```
cgagcctcag gaatgtttga cagtgtagtg ctttgtgagt gctacgacgc aggggctgcg    1500
tggtacgatc tcacaccagc ggagaccacc gtcaggctta gagcgtattt caacacgccc    1560
ggcctacccg tgtgtcaaga ccatcttgaa ttttgggagg cagttttcac cggcctcaca    1620
cacatagacg cccacttcct ctcccaaaca aagcaagcgg gggagaactt cgcgtaccta    1680
gtagcctacc aagctacggt gtgcgccaga gccaaggccc ctcccccgtc ctgggacgcc    1740
atgtggaagt gcctggcccg actcaagcct acgcttgcgg gccccacacc tctcctgtac    1800
cgtttgggcc ctattaccaa tgaggtcacc ctcacacacc ctgggacgaa gtacatcgcc    1860
acatgcatgc aagctgacct tgaggtcatg accagcacgt gggtcctagc tggaggagtc    1920
ctggcagccg tcgccgcata ttgcctggcg actggatgcg tttccatcat cggccgcttg    1980
cacgtcaacc agcgagtcgt cgttgcgccg gataaggagg tcctgtatga ggcttttgat    2040
gagatggagg aatgcgcctc tagggcggct ctcatcgaag aggggcagcg gatagccgag    2100
atgttgaagt ccaagatcca aggcttgctg cagcaggcct ctaagcaggc ccaggacata    2160
caacccgcta tgcaggcttc atggcccaaa gtggaacaat tttgggccag acacatgtgg    2220
aacttcatta gcggcatcca atacctcgca ggattgtcaa cactgccagg aaccccgcg     2280 gtggcttcca tgatggcatt cagtgccgcc ctcaccagtc cgttgtcgac cagtaccacc    2340
atccttctca acatcatggg aggctggtta gcgtcccaga tcgcaccacc cgcggggcc     2400 accggctttg tcgtcagtgg cctggtgggg gctgccgtgg gcagcatagg cctgggtaag    2460
gtgctggtgg acatcctggc aggatatggt gcgggcattt cggggcccct cgtcgcattc    2520
aagatcatgt ctggcgagaa gccctctatg gaagatgtca tcaatctact gcctgggatc    2580
ctgtctccgg gagccctggt ggtggggtc atctgcgcgg ccattctgcg ccgccacgtg    2640 ggaccgggg agggcgcggt ccaatggatg aacaggctta ttgcctttgc ttccagagga    2700
aaccacgtcg cccctactca ctacgtgacg gagtcggatg cgtcgcagcg tgtgacccaa    2760
ctacttggct ctcttactat aaccagccta ctcagaagac tccacaattg gataactgag    2820
gactgcccca tcccatgctc cggatcctgg ctccgcgacg tgtgggactg ggtttgcacc    2880
atcttgacag acttcaaaaa ttggctgacc tctaaattgt tccccaagct gcccggcctc    2940
cccttcatct cttgtcaaaa ggggtacaag ggtgtgtggg ccggcactgg catcatgacc    3000
acgcgctgcc cttgcggcgc caacatctct ggcaatgtcc gctgggctc tatgaggatc    3060 acagggccta aaacctgcat gaacacctgg cagggggacct ttcctatcaa ttgctacacg    3120
gagggccagt gcgcgccgaa aacccccacg aactacaaga ccgccatctg gagggtggcg    3180
gcctcggagt acgcggaggt gacgcagcat gggtcgtact cctatgtaac aggactgacc    3240
actgacaatc tgaaaattcc ttgccaacta ccttctccag agttttctc ctgggtggac    3300 ggtgtgcaga tccataggtt tgcacccaca ccaaagccgt ttttccggga tgaggtctcg    3360
ttctgcgttg gcttaattc ctatgctgtc ggtcccagc ttccctgtga acctgagccc    3420
gacgcagacg tattgaggtc catgctaaca gatccgcccc acatcacggc ggagactgcg    3480
gcgcggcgct ggcacggggg atcacctcca tctgaggcga gctcctcagt gagccagcta    3540
tcagcaccgt cgctgcgggc cacctgcacc acccacagca acacctatga cgtggacatg    3600
gtcgatgcca acctgctcat ggagggcggt gtggctcaga cagagcctga gtccagggtg    3660
cccgttctgg actttctcga gccaatggcc gaggaagaga gcgaccttga gccctcaata    3720
ccatcggagt gcatgctccc caggagcggg tttccacggg ccttaccggc ttgggcacgg    3780
```

```
cctgactaca acccgccgct cgtggaatcg tggaggaggc cagattacca accgcccacc    3840
gttgctggtt gtgctctccc cccccccaag aaggccccga cgcctccccc aaggagacgc    3900
cggacagtgg gtctgagcga gagcaccata tcagaagccc tccagcaact ggccatcaag    3960
acctttggcc agccccctc gagcggtgat gcaggctcgt ccacggggc gggcgccgcc       4020
gaatccggcg gtccgacgtc ccctggtgag ccggcccct cagagacagg ttccgcctcc      4080
tctatgcccc ccctcgaggg ggagcctgga gatccggacc tggagtctga tcaggtagag    4140
cttcaacctc cccccaggg gggggggta gctcccggtt cgggctcggg gtcttggtct       4200
acttgctccg aggaggacga taccaccgtg tgctgctcca tgtcatactc ctggaccggg    4260
gctctaataa ctccctgtag ccccgaagag gaaaagttgc caatcaaccc tttgagtaac    4320
tcgctgttgc gataccataa caaggtgtac tgtacaacat caaagagcgc ctcacagagg    4380
gctaaaaagg taacttttga caggacgcaa gtgctcgacg cccattatga ctcagtctta    4440
aaggacatca agctagcggc ttccaaggtc agcgcaaggc tcctcacctt ggaggaggcg    4500
tgccagttga ctccacccca ttctgcaaga tccaagtatg gattcggggc caaggaggtc    4560
cgcagcttgt ccgggagggc cgttaaccac atcaagtccg tgtggaagga cctcctggaa    4620
gacccacaaa caccaattcc cacaaccatc atggccaaaa atgaggtgtt ctgcgtggac    4680
cccgccaagg ggggtaagaa accagctcgc ctcatcgttt accctgacct cggcgtccgg    4740
gtctgcgaga aaatggccct ctatgacatt acacaaaagc ttcctcaggc ggtaatggga    4800
gcttcctatg gcttccagta ctcccctgcc caacgggtgg agtatctctt gaaagcatgg    4860
gcggaaaaga aggaccccat gggttttttcg tatgataccc gatgcttcga ctcaaccgtc    4920
actgagagag acatcaggac cgaggagtcc atataccagg cctgctccct gcccgaggag    4980
gcccgcactg ccatacactc gctgactgag agactttacg taggagggcc catgttcaac    5040
agcaagggtc aaacctgcgg ttacagacgt tgccgcgcca gcggggtgct aaccactagc    5100
atgggtaaca ccatcacatg ctatgtgaaa gccctagcgg cctgcaaggc tgcggggata    5160
gttgcgccca caatgctggt atgcggcgat gacctagtag tcatctcaga aagccagggg    5220
actgaggagg acgagcggaa cctgagagcc ttcacggagg ccatgaccag gtactctgcc    5280
cctcctggtg atccccccag accggaatat gacctggagc taataacatc ctgttcctca    5340
aatgtgtctg tggcgttggg cccgcggggc cgccgcagat actacctgac cagagaccca    5400
accactccac tcgcccgggc tgcctgggaa acagttagac actcccctat caattcatgg    5460
ctgggaaaca tcatccagta tgctccaacc atatgggttc gcatggtcct aatgacacac    5520
ttcttctcca ttctcatggt ccaagacacc ctggaccaga acctcaactt tgagatgtat    5580
ggatcagtat actccgtgaa tcctttggac cttccagcca taattgagag gttacacggg    5640
cttgacgcct tttctatgca cacatactct caccacgaac tgacgcgggt ggcttcagcc    5700
ctcagaaaac ttggggcgcc accccctcagg gtgtggaaga gtcgggctcg cgcagtcagg    5760
gcgtccctca tctcccgtgg agggaaagcg gccgtttgcg gccgatatct cttcaattgg    5820
gcggtgaaga ccaagctcaa actcactcca ttgccggagg cgcgcctact ggacttatcc    5880
agttggttca ccgtcggcgc cggcggggc gacattttc acagcgtgtc gcgcgcccga    5940
ccccgctcat tactcttcgg cctactccta cttttcgtag gggtaggcct cttcctactc    6000
cccgctcggt ag                                                         6012

<210> SEQ ID NO 2
<211> LENGTH: 1773
```

```
<212> TYPE: DNA
<213> ORGANISM: Hepatitis C virus
<220> FEATURE:
<221> NAME/KEY: CDS
<222> LOCATION: (1)..(1773)
<223> OTHER INFORMATION: sequence encoding NS5B protein of JFH1 (cDNA
      sequence)

<400> SEQUENCE: 2 tcc atg tca tac tcc tgg acc ggg gct cta ata act ccc tgt agc ccc     48
Ser Met Ser Tyr Ser Trp Thr Gly Ala Leu Ile Thr Pro Cys Ser Pro
1               5                   10                  15 gaa gag gaa aag ttg cca atc aac cct ttg agt aac tcg ctg ttg cga     96
Glu Glu Glu Lys Leu Pro Ile Asn Pro Leu Ser Asn Ser Leu Leu Arg
            20                  25                  30 tac cat aac aag gtg tac tgt aca aca tca aag agc gcc tca cag agg    144
Tyr His Asn Lys Val Tyr Cys Thr Thr Ser Lys Ser Ala Ser Gln Arg
        35                  40                  45 gct aaa aag gta act ttt gac agg acg caa gtg ctc gac gcc cat tat    192
Ala Lys Lys Val Thr Phe Asp Arg Thr Gln Val Leu Asp Ala His Tyr
    50                  55                  60 gac tca gtc tta aag gac atc aag cta gcg gct tcc aag gtc agc gca    240
Asp Ser Val Leu Lys Asp Ile Lys Leu Ala Ala Ser Lys Val Ser Ala
65                  70                  75                  80 agg ctc ctc acc ttg gag gag gcg tgc cag ttg act cca ccc cat tct    288
Arg Leu Leu Thr Leu Glu Glu Ala Cys Gln Leu Thr Pro Pro His Ser
                85                  90                  95 gca aga tcc aag tat gga ttc ggg gcc aag gag gtc cgc agc ttg tcc    336
Ala Arg Ser Lys Tyr Gly Phe Gly Ala Lys Glu Val Arg Ser Leu Ser
            100                 105                 110 ggg agg gcc gtt aac cac atc aag tcc gtg tgg aag gac ctc ctg gaa    384
Gly Arg Ala Val Asn His Ile Lys Ser Val Trp Lys Asp Leu Leu Glu
        115                 120                 125 gac cca caa aca cca att ccc aca acc atc atg gcc aaa aat gag gtg    432
Asp Pro Gln Thr Pro Ile Pro Thr Thr Ile Met Ala Lys Asn Glu Val
    130                 135                 140 ttc tgc gtg gac ccc gcc aag ggg ggt aag aaa cca gct cgc ctc atc    480
Phe Cys Val Asp Pro Ala Lys Gly Gly Lys Lys Pro Ala Arg Leu Ile
145                 150                 155                 160 gtt tac cct gac ctc ggc gtc cgg gtc tgc gag aaa atg gcc ctc tat    528
Val Tyr Pro Asp Leu Gly Val Arg Val Cys Glu Lys Met Ala Leu Tyr
                165                 170                 175 gac att aca caa aag ctt cct cag gcg gta atg gga gct tcc tat ggc    576
Asp Ile Thr Gln Lys Leu Pro Gln Ala Val Met Gly Ala Ser Tyr Gly
            180                 185                 190 ttc cag tac tcc cct gcc caa cgg gtg gag tat ctc ttg aaa gca tgg    624
Phe Gln Tyr Ser Pro Ala Gln Arg Val Glu Tyr Leu Leu Lys Ala Trp
        195                 200                 205 gcg gaa aag aag gac ccc atg ggt ttt tcg tat gat acc cga tgc ttc    672
Ala Glu Lys Lys Asp Pro Met Gly Phe Ser Tyr Asp Thr Arg Cys Phe
    210                 215                 220 gac tca acc gtc act gag aga gac atc agg acc gag gag tcc ata tac    720
Asp Ser Thr Val Thr Glu Arg Asp Ile Arg Thr Glu Glu Ser Ile Tyr
225                 230                 235                 240 cag gcc tgc tcc ctg ccc gag gag gcc cgc act gcc ata cac tcg ctg    768
Gln Ala Cys Ser Leu Pro Glu Glu Ala Arg Thr Ala Ile His Ser Leu
                245                 250                 255 act gag aga ctt tac gta gga ggg ccc atg ttc aac agc aag ggt caa    816
Thr Glu Arg Leu Tyr Val Gly Gly Pro Met Phe Asn Ser Lys Gly Gln
            260                 265                 270 acc tgc ggt tac aga cgt tgc cgc gcc agc ggg gtg cta acc act agc    864
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Thr | Cys | Gly | Tyr | Arg | Arg | Cys | Arg | Ala | Ser | Gly | Val | Leu | Thr | Thr | Ser |      |
|     |     | 275 |     |     |     | 280 |     |     |     |     | 285 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| atg | ggt | aac | acc | atc | aca | tgc | tat | gtg | aaa | gcc | cta | gcg | gcc | tgc | aag | 912  |
| Met | Gly | Asn | Thr | Ile | Thr | Cys | Tyr | Val | Lys | Ala | Leu | Ala | Ala | Cys | Lys |      |
|     | 290 |     |     |     |     | 295 |     |     |     |     | 300 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gct | gcg | ggg | ata | gtt | gcg | ccc | aca | atg | ctg | gta | tgc | ggc | gat | gac | cta | 960  |
| Ala | Ala | Gly | Ile | Val | Ala | Pro | Thr | Met | Leu | Val | Cys | Gly | Asp | Asp | Leu |      |
| 305 |     |     |     |     | 310 |     |     |     |     | 315 |     |     |     |     | 320 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gta | gtc | atc | tca | gaa | agc | cag | ggg | act | gag | gag | gac | gag | cgg | aac | ctg | 1008 |
| Val | Val | Ile | Ser | Glu | Ser | Gln | Gly | Thr | Glu | Glu | Asp | Glu | Arg | Asn | Leu |      |
|     |     |     |     | 325 |     |     |     |     | 330 |     |     |     |     | 335 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aga | gcc | ttc | acg | gag | gcc | atg | acc | agg | tac | tct | gcc | cct | cct | ggt | gat | 1056 |
| Arg | Ala | Phe | Thr | Glu | Ala | Met | Thr | Arg | Tyr | Ser | Ala | Pro | Pro | Gly | Asp |      |
|     |     |     | 340 |     |     |     |     | 345 |     |     |     |     | 350 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ccc | ccc | aga | ccg | gaa | tat | gac | ctg | gag | cta | ata | aca | tcc | tgt | tcc | tca | 1104 |
| Pro | Pro | Arg | Pro | Glu | Tyr | Asp | Leu | Glu | Leu | Ile | Thr | Ser | Cys | Ser | Ser |      |
|     |     | 355 |     |     |     |     | 360 |     |     |     |     | 365 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aat | gtg | tct | gtg | gcg | ttg | ggc | ccg | cgg | ggc | cgc | cgc | aga | tac | tac | ctg | 1152 |
| Asn | Val | Ser | Val | Ala | Leu | Gly | Pro | Arg | Gly | Arg | Arg | Arg | Tyr | Tyr | Leu |      |
| 370 |     |     |     |     | 375 |     |     |     |     | 380 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| acc | aga | gac | cca | acc | act | cca | ctc | gcc | cgg | gct | gcc | tgg | gaa | aca | gtt | 1200 |
| Thr | Arg | Asp | Pro | Thr | Thr | Pro | Leu | Ala | Arg | Ala | Ala | Trp | Glu | Thr | Val |      |
| 385 |     |     |     |     | 390 |     |     |     |     | 395 |     |     |     |     | 400 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aga | cac | tcc | cct | atc | aat | tca | tgg | ctg | gga | aac | atc | atc | cag | tat | gct | 1248 |
| Arg | His | Ser | Pro | Ile | Asn | Ser | Trp | Leu | Gly | Asn | Ile | Ile | Gln | Tyr | Ala |      |
|     |     |     |     | 405 |     |     |     |     | 410 |     |     |     |     | 415 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cca | acc | ata | tgg | gtt | cgc | atg | gtc | cta | atg | aca | cac | ttc | ttc | tcc | att | 1296 |
| Pro | Thr | Ile | Trp | Val | Arg | Met | Val | Leu | Met | Thr | His | Phe | Phe | Ser | Ile |      |
|     |     |     | 420 |     |     |     |     | 425 |     |     |     |     | 430 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctc | atg | gtc | caa | gac | acc | ctg | gac | cag | aac | ctc | aac | ttt | gag | atg | tat | 1344 |
| Leu | Met | Val | Gln | Asp | Thr | Leu | Asp | Gln | Asn | Leu | Asn | Phe | Glu | Met | Tyr |      |
|     | 435 |     |     |     |     | 440 |     |     |     |     | 445 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gga | tca | gta | tac | tcc | gtg | aat | cct | ttg | gac | ctt | cca | gcc | ata | att | gag | 1392 |
| Gly | Ser | Val | Tyr | Ser | Val | Asn | Pro | Leu | Asp | Leu | Pro | Ala | Ile | Ile | Glu |      |
| 450 |     |     |     |     | 455 |     |     |     |     | 460 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| agg | tta | cac | ggg | ctt | gac | gcc | ttt | tct | atg | cac | aca | tac | tct | cac | cac | 1440 |
| Arg | Leu | His | Gly | Leu | Asp | Ala | Phe | Ser | Met | His | Thr | Tyr | Ser | His | His |      |
| 465 |     |     |     | 470 |     |     |     |     | 475 |     |     |     |     | 480 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gaa | ctg | acg | cgg | gtg | gct | tca | gcc | ctc | aga | aaa | ctt | ggg | gcg | cca | ccc | 1488 |
| Glu | Leu | Thr | Arg | Val | Ala | Ser | Ala | Leu | Arg | Lys | Leu | Gly | Ala | Pro | Pro |      |
|     |     |     |     | 485 |     |     |     |     | 490 |     |     |     |     | 495 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctc | agg | gtg | tgg | aag | agt | cgg | gct | cgc | gca | gtc | agg | gcg | tcc | ctc | atc | 1536 |
| Leu | Arg | Val | Trp | Lys | Ser | Arg | Ala | Arg | Ala | Val | Arg | Ala | Ser | Leu | Ile |      |
|     |     |     | 500 |     |     |     |     | 505 |     |     |     |     | 510 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tcc | cgt | gga | ggg | aaa | gcg | gcc | gtt | tgc | ggc | cga | tat | ctc | ttc | aat | tgg | 1584 |
| Ser | Arg | Gly | Gly | Lys | Ala | Ala | Val | Cys | Gly | Arg | Tyr | Leu | Phe | Asn | Trp |      |
|     |     | 515 |     |     |     |     | 520 |     |     |     |     | 525 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gcg | gtg | aag | acc | aag | ctc | aaa | ctc | act | cca | ttg | ccg | gag | gcg | cgc | cta | 1632 |
| Ala | Val | Lys | Thr | Lys | Leu | Lys | Leu | Thr | Pro | Leu | Pro | Glu | Ala | Arg | Leu |      |
|     | 530 |     |     |     |     | 535 |     |     |     |     | 540 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctg | gac | tta | tcc | agt | tgg | ttc | acc | gtc | ggc | gcc | ggc | ggg | ggc | gac | att | 1680 |
| Leu | Asp | Leu | Ser | Ser | Trp | Phe | Thr | Val | Gly | Ala | Gly | Gly | Gly | Asp | Ile |      |
| 545 |     |     |     |     | 550 |     |     |     |     | 555 |     |     |     |     | 560 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ttt | cac | agc | gtg | tcg | cgc | gcc | cga | ccc | cgc | tca | tta | ctc | ttc | ggc | cta | 1728 |
| Phe | His | Ser | Val | Ser | Arg | Ala | Arg | Pro | Arg | Ser | Leu | Leu | Phe | Gly | Leu |      |
|     |     |     |     | 565 |     |     |     |     | 570 |     |     |     |     | 575 |     |      |

|     |     |     |     |     |     |     |     |     |     |     |     |     |     |      |
| --- | --- | --- | --- | --- | --- | --- | --- | --- | --- | --- | --- | --- | --- | ---- |
| ctc | cta | ctt | ttc | gta | ggg | gta | ggc | ctc | ttc | cta | ctc | ccc | gct | cgg | 1773 |
| Leu | Leu | Leu | Phe | Val | Gly | Val | Gly | Leu | Phe | Leu | Leu | Pro | Ala | Arg |      |
|     |     |     | 580 |     |     |     |     | 585 |     |     |     |     | 590 |     |      |

<210> SEQ ID NO 3
<211> LENGTH: 591
<212> TYPE: PRT
<213> ORGANISM: Hepatitis C virus
<220> FEATURE:
<221> NAME/KEY: misc_feature
<222> LOCATION: (1)..(591)
<223> OTHER INFORMATION: NS5B protein of JFH1

<400> SEQUENCE: 3

```
Ser Met Ser Tyr Ser Trp Thr Gly Ala Leu Ile Thr Pro Cys Ser Pro
1               5                   10                  15

Glu Glu Glu Lys Leu Pro Ile Asn Pro Leu Ser Asn Ser Leu Leu Arg
            20                  25                  30

Tyr His Asn Lys Val Tyr Cys Thr Thr Ser Lys Ser Ala Ser Gln Arg
        35                  40                  45

Ala Lys Lys Val Thr Phe Asp Arg Thr Gln Val Leu Asp Ala His Tyr
    50                  55                  60

Asp Ser Val Leu Lys Asp Ile Lys Leu Ala Ala Ser Lys Val Ser Ala
65                  70                  75                  80

Arg Leu Leu Thr Leu Glu Glu Ala Cys Gln Leu Thr Pro Pro His Ser
                85                  90                  95

Ala Arg Ser Lys Tyr Gly Phe Gly Ala Lys Glu Val Arg Ser Leu Ser
            100                 105                 110

Gly Arg Ala Val Asn His Ile Lys Ser Val Trp Lys Asp Leu Leu Glu
        115                 120                 125

Asp Pro Gln Thr Pro Ile Pro Thr Thr Ile Met Ala Lys Asn Glu Val
130                 135                 140

Phe Cys Val Asp Pro Ala Lys Gly Gly Lys Lys Pro Ala Arg Leu Ile
145                 150                 155                 160

Val Tyr Pro Asp Leu Gly Val Arg Val Cys Glu Lys Met Ala Leu Tyr
                165                 170                 175

Asp Ile Thr Gln Lys Leu Pro Gln Ala Val Met Gly Ala Ser Tyr Gly
            180                 185                 190

Phe Gln Tyr Ser Pro Ala Gln Arg Val Glu Tyr Leu Leu Lys Ala Trp
        195                 200                 205

Ala Glu Lys Lys Asp Pro Met Gly Phe Ser Tyr Asp Thr Arg Cys Phe
    210                 215                 220

Asp Ser Thr Val Thr Glu Arg Asp Ile Arg Thr Glu Glu Ser Ile Tyr
225                 230                 235                 240

Gln Ala Cys Ser Leu Pro Glu Glu Ala Arg Thr Ala Ile His Ser Leu
                245                 250                 255

Thr Glu Arg Leu Tyr Val Gly Gly Pro Met Phe Asn Ser Lys Gly Gln
            260                 265                 270

Thr Cys Gly Tyr Arg Arg Cys Arg Ala Ser Gly Val Leu Thr Thr Ser
        275                 280                 285

Met Gly Asn Thr Ile Thr Cys Tyr Val Lys Ala Leu Ala Ala Cys Lys
    290                 295                 300

Ala Ala Gly Ile Val Ala Pro Thr Met Leu Val Cys Gly Asp Asp Leu
305                 310                 315                 320

Val Val Ile Ser Glu Ser Gln Gly Thr Glu Glu Asp Glu Arg Asn Leu
                325                 330                 335

Arg Ala Phe Thr Glu Ala Met Thr Arg Tyr Ser Ala Pro Pro Gly Asp
            340                 345                 350

Pro Pro Arg Pro Glu Tyr Asp Leu Glu Leu Ile Thr Ser Cys Ser Ser
```

355                 360                 365
Asn Val Ser Val Ala Leu Gly Pro Arg Gly Arg Arg Tyr Tyr Leu
        370                 375                 380

Thr Arg Asp Pro Thr Thr Pro Leu Ala Arg Ala Ala Trp Glu Thr Val
385                 390                 395                 400

Arg His Ser Pro Ile Asn Ser Trp Leu Gly Asn Ile Ile Gln Tyr Ala
                405                 410                 415

Pro Thr Ile Trp Val Arg Met Val Leu Met Thr His Phe Phe Ser Ile
        420                 425                 430

Leu Met Val Gln Asp Thr Leu Asp Gln Asn Leu Asn Phe Glu Met Tyr
        435                 440                 445

Gly Ser Val Tyr Ser Val Asn Pro Leu Asp Leu Pro Ala Ile Ile Glu
        450                 455                 460

Arg Leu His Gly Leu Asp Ala Phe Ser Met His Thr Tyr Ser His His
465                 470                 475                 480

Glu Leu Thr Arg Val Ala Ser Ala Leu Arg Lys Leu Gly Ala Pro Pro
                485                 490                 495

Leu Arg Val Trp Lys Ser Arg Ala Arg Ala Val Arg Ala Ser Leu Ile
        500                 505                 510

Ser Arg Gly Gly Lys Ala Ala Val Cys Gly Arg Tyr Leu Phe Asn Trp
        515                 520                 525

Ala Val Lys Thr Lys Leu Lys Leu Thr Pro Leu Pro Glu Ala Arg Leu
530                 535                 540

Leu Asp Leu Ser Ser Trp Phe Thr Val Gly Ala Gly Gly Asp Ile
545                 550                 555                 560

Phe His Ser Val Ser Arg Ala Arg Pro Arg Ser Leu Leu Phe Gly Leu
                565                 570                 575

Leu Leu Leu Phe Val Gly Val Gly Leu Phe Leu Leu Pro Ala Arg
        580                 585                 590

<210> SEQ ID NO 4
<211> LENGTH: 14
<212> TYPE: PRT
<213> ORGANISM: Artificial Sequence
<220> FEATURE:
<223> OTHER INFORMATION: Synthetic peptide designed based on JFH1 E2
      fragment

<400> SEQUENCE: 4

Gly Thr Thr Thr Val Gly Gly Ala Val Ala Arg Ser Thr Asn
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic peptide designed based on JFH1 E2

<400> SEQUENCE: 5

Cys Asp Leu Glu Asp Arg Asp Arg Ser Gln Leu Ser Pro Leu
1               5                   10

<210> SEQ ID NO 6
<211> LENGTH: 17
<212> TYPE: DNA
<213> ORGANISM: Artificial Sequence
<220> FEATURE:
<223> OTHER INFORMATION: Synthetic primer (R6-130-S17)

```
<400> SEQUENCE: 6
cgggagagcc atagtgg                                                        17

<210> SEQ ID NO 7
<211> LENGTH: 19
<212> TYPE: DNA
<213> ORGANISM: Artificial Sequence
<220> FEATURE:
<223> OTHER INFORMATION: Synthetic primer (R6-290-R19)

<400> SEQUENCE: 7
agtaccacaa ggcctttcg                                                      19

<210> SEQ ID NO 8
<211> LENGTH: 21
<212> TYPE: DNA
<213> ORGANISM: Artificial Sequence
<220> FEATURE:
<223> OTHER INFORMATION: Synthetic TaqMan probe (R6-148-S21FT)

<400> SEQUENCE: 8
ctgcggaacc ggtgagtaca c                                                   21

<210> SEQ ID NO 9
<211> LENGTH: 9678
<212> TYPE: RNA
<213> ORGANISM: Homo sapiens
<220> FEATURE:
<221> NAME/KEY: misc_feature
<222> LOCATION: (1)..(9678)
<223> OTHER INFORMATION: full-length Hepatitis C virus genomic RNA
      derived from JFH1 strain(JFH-1 clone)

<400> SEQUENCE: 9
accugccccu aauaggggcg acacuccgcc augaaucacu ccccugugag gaacuacugu          60
cuucacgcag aaagcgccua gccauggcgu uaguaugagu gucguacagc cuccaggccc         120
cccccucccg ggagagccau aguggucugc ggaaccggug aguacaccgg aauugccggg         180
aagacugggu ccuuucuugg auaaacccac ucuaugcccg ccauuuggg cgugcccccg          240 caagacugcu agccgaguag cguuggguug cgaaaggccu guguacugc cugauaggg           300 cgcuugcgag ugccccggga ggucucuag accgugcacc augagcacaa auccuaaacc         360
ucaaagaaaa accaaaagaa acaccaaccg ucgcccagaa gacguuaagu ucccgggcgg         420
cggccagauc guuggcggag uauacuuguu gccgcgcagg ggccccaggu uggguguegc         480 cacgacaagg aaaacuucgg agcgguccca gccacguggg agacgccagc ccauccccaa        540
agaucggcgc uccacuggca aggccugggg aaaaccaggu cgccccuggc cccuauaugg        600
gaaugaggga cucggcuggg caggauggcu ccugucccc cgaggcucuc gccccuccug          660
gggccccacu gaccccggc auaggucgcg caacgugggu aaagucaucg acacccuaac          720
guguggcuuu gccgaccuca uggguacau cccgucgua ggcgccccgc uuaguggcgc          780
cgccagagcu gucgcgcacg gcgugagagu ccuggaggac ggggguaauu augcaacagg        840
gaaccuaccc gguuuccccu uuucuaucuu cuugcuggcc cuguguccu gcaucaccgu        900 uccggucucu gcgcccagg ugaagaauac caguagcagc uacaugguga ccaaugacug        960
cuccaaugac agcaucacuu ggcagcucga ggcugcgguu cccacguccu ccgggugcgu       1020
cccgugcgag agagugggga auacgucacg guguugggug ccagucucgc caaacauggc      1080
ugugcggcag cccggugccc ucacgcaggg ucugcggacg cacaucgaua ugguugugau      1140
```

```
guccgccacc uucugcucug cucucuacgu gggggaccuc uguggcgggg ugaugcucgc    1200
ggcccaggug uucaucgucu cgccgcagua ccacugguuu gugcaagaau gcaauugcuc    1260
caucuacccu ggcaccauca cuggacaccg cauggcaugg gacaugauga ugaacugguc    1320
gcccacggcc accaugaucc uggcguacgu gaugcgcguc cccgagguca ucauagacau    1380
cguuagcggg gcucacuggg gcgucauguu cggcuuggcc uacuucucua ugcagggagc    1440
gugggcgaag gucauuguca uccuucugcu ggccgcuggg guggacgcgg gcaccaccac    1500
cguuggaggc gcuguugcac guccaccaa cgugauugcc ggcguguuca gccauggccc    1560
ucagcagaac auucagcuca uuaacaccaa cggcaguugg cacaucaacc guacugccuu    1620
gaauugcaau gacuccuuga acaccggcuu ucucgcggcc uuguucuaca ccaaccgcuu    1680
uaacucguca ggguguccag ggcgccuguc cgccugccgc aacaucgagg cuuuccggau    1740 agggugggc acccuacagu acgaggauaa ugucaccaau ccagaggaua ugaggccgua    1800
cugcuggcac uaccccccaa agccguguggg cguagucccc gcgaggucug ugugggccc    1860 agugaucugu uuccccccca gcccgguagu aguggcacg accgcagac guggagugcc    1920 caccuacaca uggggagaga augagacaga ugucuuccua cugaacagca cccgaccgcc    1980
gcagggcuca uгguucggcu gcacguggau gaaucccacu gguuucacca agacuugugg    2040
cgcgccaccu ugccgcacca gagcugacuu caacgccagc acggacuugu ugugcccuac    2100
ggauuguuuu aggaagcauc cugaugccac uuauauuaag ugggucug ggcccuggcu    2160 cacaccaaag ugccuggucc acuacccuua cagacucugg cauuaccccu gcacagucaa    2220
uuuuaccauc uucaagauaa gaauguaugu aggggggguu gagcacaggc ucacggccgc    2280
augcaacuuc acucgugggg aucgcugcga cuuggaggac agggacagga gucagcuguc    2340
uccucuguug cacucuacca cggaaugggc cauccugccc ugcaccuacu cagacuuacc    2400
cgcuuuguca acuggucuuc uccaccuuca ccagaacauc guggacguac aauacaugua    2460
uggccucuca ccugcuauca caaaauacgu cguucgaugg gagugggugg uacucuuauu    2520
ccugcucuua gcggacgcca gagucugcgc cugcuugugg augcucaucu uguugggcca    2580
ggccgaagca gcauuggaga aguuggucgu cuugcacgcu gcgagugcgg cuaacugcca    2640
uggccuccua uauuugcca cuucuucgu ggcagcuugg cacaucaggg gucgggguggu    2700 ccccuugacc accauugcc ucacuggccu auggcccuuc ugccuacugc ucauggcacu    2760
gccccggcag gcuuaugccu augacgcacc ugugcacgga cagauaggcg uggguuuguu    2820
gauauugauc accccuuuca cacucacccc ggggauauaag acccuccucg gccagugucu    2880 gugguggguug ugcuaucucc ugacccuggg ggaagccaug auucaggagu ggguaccacc    2940
caugcaggug cgcggcggcc gcgauggcau cgcguggggcc gucacuauau ucugcccggg    3000
ugguguguuu gacauuacca aauggcuuuu ggcguugcuu gggccugcuu acccucuuaag    3060 ggccgcuuug acacaugugc cguacuucgu cagagcucac gcucugauaa ggguaugcgc    3120
uuuggugaag cagcucgcgg ggguaggua uguucaggug gcgcuauugg cccuggcag    3180 guggacuggc accuacaucu ugaccaccu cacaccuaug ucggacuggg ccgcuagcgg    3240
ccugcgcgac uuagcggucg ccgguggaacc caucaucuuc agccgauggg agaagaaggu    3300
caucgucugg ggagcggaga cggcugcaug uggggacauu cuacauggac uucccggucu    3360
cgcccgacuc ggccaggaga uccccucgg cccagcugau ggcuacaccu ccaaggggug    3420
gaagcuccuu gcucccauca cugcuuaugc ccagcaaaaca cgaggccucc ugggcgcau    3480 aguggugagu augacggggc gugacaggac agaacaggcc ggggaagucc aaauccuguc    3540
```

```
cacagucucu cagaccuucc ucggaacaac caucucgggg guuuugugga cuguuuacca    3600
cggagcuggc aacaagacuc uagccggcuu acggggyccg gucacgcaga uguacucgag    3660
ugcugagggg gacuugguag gcuggccag ccccccuggg accaagucuu uggagccgug     3720
caagugugga gccgucgacc uauaucuggu cacgcggaac gcugaugyuca ucccggcucg    3780 gagacgcggg gacaagcggg gagcauugcu cuccccgaga cccauuucga ccuugaaggg    3840
guccucgggg gggccggugc ucugcccuag gggccacguc guugggcucu uccgagcagc    3900
ugugugcucu cggggcgugg ccaaauccau cgauuucauc cccguugaga cacucgacgu    3960
uguuacaagg ucucccacuu ucagugacaa cagcacgcca ccggcugugc cccagaccua    4020
ucaggucggg uacuugcaug cuccaacugg caguggaaag agcaccaagg ucccugucgc    4080
guaugccgcc caggguaca aaguacuagu gcuuaacccc ucgguagcug ccacccuggg     4140 guuugggggcg uaccuaucca aggcacaugg caucaauccc aacauuagga cuggagucag   4200
gaccgugaug accggggagg ccaucacgua cuccacauau ggcaaauuuc ucgccgaugg    4260
gggcugcgcu agcggcgccu augacaucau cauaugcgau gaaugccacg cuguggaugc    4320
uaccuccauu cucggcaucg gaacggcccu ugaucaagca gagacagccg gggcagacu     4380 aacugugcug gcuacggcca cacccccgg gucagugaca acccccccauc ccgauauaga    4440 agagguaggc cucgggcggg aggguggagau ccccuucuau ggggggcga uuccccuauc    4500 cugcaucaag ggagggagac accugauuuu cugccacuca aagaaaaagu gugacgagcu    4560
cgcggcggcc cuucgggggca ugggcuugaa gccgguggca acuauagag gguuggacgu    4620 cuccauaaua ccagcucagg gagauguggu ggucgucgcc accgacgccc ucaugacggg    4680
guacacugga gacuuugacu ccgugaucga cugcaaugua gcggucaccc aagcugucga    4740
cuucagccug gaccccaccu ucacuauaac cacacagacu gucccacaag acgcugucuc    4800
acgcagucag cgccgcgggc gcacaggguag aggaagacag ggcacuuaua gguauguuuc    4860
cacuggugaa cgagccucag gaauguuuga caguguagug cuuugugagu gcuacgacgc    4920 aggggucugcg ugguacgauc ucacaccagc ggagaccacc gucaggcuua gagcguauuu    4980
caacacgccc ggccuacccg ugucaagga ccaucuugaa uuuugggagg caguuuucac    5040
cggccucaca cacauagacg cccacuuccu cucccaaaca aagcaagcgg gggagaacuu    5100
cgcgnaccua guagccuacc aagcuacggu gugcgccaga gccaaggccc cucccccguc    5160
cugggacgcc auguggaagu gccugggccccg acucaagccu acgcuugcgg ccccacacc    5220 ucuccuguac cguuugggcc cuauuaccaa ugaggucacc cucacacacc cugggacgaa    5280
guacaucgcc acaugcaugc aagcugaccu ugaggucaug accagcacgu ggcuucagc    5340 uggaggaguc cuggcagccg ucgccgcaua uugccggcg acuggaugcg uuuccaucau    5400
cggccgcuug cacgucaacc agcgagucgu cguucgccg gauaaggagg uccuguauga    5460
ggcuuuugau gagauggagg aaugcgccuc uaggggcggcu cucaucgaag aggggcagcg    5520 gauaagccgag auguugaagu ccaagaucca aggcuugcug cagcaggcuu cuaagcaggc    5580
ccaggacaua caacccgcua ugcaggcuuc augggccaaa guggaacaau uugggccag     5640 acacauggg aacuucauua gcggcaucca auaccgcga ggauuggucaa cacugccagg    5700 gaaccccgcg gguggcuucca ugauggcauu cagugccgcc cucaccagau cguugucgac    5760 cagauaccacc auccuucuca acaucaugggg aggcugguua gcgucccaga ucgaccacc    5820 cgcgggggcc accggccuug cucgugcaggg ccugguggg gcugccguggg gacagcaagg    5880
```

```
ccuggguaag gugcuggugg acauccuggc aggauauggu gcgggcauuu cggggggcccu    5940
cgucgcauuc aagaucaugu cuggcgagaa gcccucuaug gaagauguca ucaaucuacu    6000
gccugggauc cugucuccgg gagcccuggu ggugggggguc aucugcgcgg ccauucugcg    6060
ccgccacgug ggaccggggg agggcgcggu ccaauggaug aacaggcuua uugccuuugc    6120
uuccagagga aaccacgucg cccccuacuca cuacgugacg gagucggaug cgucgcagcg    6180
ugugacccaa cuacuuggcu cucuuacuau aaccagccua cucagaagac uccacaauug    6240
gauaacugag gacugcccca ucccaugcuc cggauccugg cuccgcgacg uggggacug     6300
ggguuugcacc aucuugacag acuucaaaaa uuggcugacc ucuaaauugu ccccaagcu    6360
gcccggccuc cccuucaucu cuugucaaaa gggguacaag ggugugugg ccggcacugg     6420
caucaugacc acgcgcugcc cuugcggcgc caacaucucu ggcaaugucc gccugggcuc    6480
uaugaggauc acagggccua aaaccugcau gaacaccugg caggggaccu uccuaucaa    6540
uugcuacacg gagggccagu gcgcgccgaa accccccacg aacuacaaga ccgccaucug    6600
gagggugcg gccucggagu acgcggaggu gacgcagcau gggucguacu ccuauguaac    6660
aggacugacc acugacaauc ugaaaauucc uugccaacua ccuucuccag aguuuuucuc    6720
cugggguggac ggugugcaga uccauagguu ugcacccaca ccaaagccgu uuuuccggga   6780
ugaggcucg uucugcguug ggcuuaauuc cuaugcuguc gggucccagc uucccuguga    6840
accgagcccc gacgcagacg uauugaggc caugcuaaca gauccgccccc acaucacggc   6900
ggagacugcg gcgcggcgcu uggcacggg aucaccucca ucugaggcga gcuccucagu    6960
gagccagcua ucagcaccgu cgcugcggc caccugcacc acccacagca acaccuauga    7020
cguggacaug gucgaugcca accugcucau ggagggcggu guggcucaga cagagccuga    7080
guccagggug cccguuucugg acuuucucga gccaauggcc gaggaagaga gcgaccuuga    7140
gcccucaaua ccaucggagu gcaugcuccc caggagcggg uuccacggg ccuuaccggc     7200
uugggcacgg ccugacuaca acccgccgcu cguggaaucg uggaggaggc cagauuacca    7260
accgcccacc guugcugguu gugcucuccc cccccccaag aaggcccga cgccucccc     7320
aaggagacgc cggacagugg gucugagcga gagcaccaua ucagaagccc uccagcaacu    7380
ggccaucaag accuuuggcc agcccccuc gagcggugau gcaggcucgu ccacggggc     7440
gggcgccgcc gaaucggcg guccgacguc cccuggugag ccggccccu cagagacagg    7500
uuccgccucc ucuaugcccc cccucgaggg ggagccugga gauccggacc uggagucuga    7560
ucagguagag cuucaaccuc cccccagggg ggggggua gccccggu cgggcucggg         7620
gucuuggucu acuugcuccg aggaggacga uaccaccgug ugcugcca ugucauacuc       7680
cuggaccggg gcucuaauaa cucccuguag ccccgaagag gaaaguugc caaucaaccc     7740
uuugaguaac ucgcuguugc gauaccauaa caaggguguac uguacaacau caaagagcgc    7800
cucacagagg gcuaaaaagg uaacuuuuga caggacgcaa gugcucgacg cccauuauga    7860
cucagucuua aaggacauca agcuagcggc uuccaagguc agcgcaaggc uccucaccuu    7920
ggaggaggcg ugccagguga cuccaccccc uuucugcaaga uccaaguaug gauucggggc    7980
caagggaguc cgcagcuugu ccgggagggc cguuaaccac aucaaguccg uggaagga      8040
ccuccuggaa gacccacaaa caccaauuc cacaaccauc auggccaaaa augaggguu      8100
cugcgggac cccgccaagg ggguaagaa accagcucgc cucaucguuu acccugaccu       8160
cggcguccgg gucugcgaga aaauggcccu cuaugacauu acacaaaagc uuccucaggc    8220
gguaaugggga gcuuccuaug gcuuccagua cuccccugcc caacgggugg aguaucucuu    8280
```

```
gaaagcaugg gcggaaaaga aggaccccau ggguuuuucg uaugauaccc gaugcuucga   8340
cucaaccguc acugagagag acaucaggac cgaggagucc auauaccagg ccugcucccu   8400
gcccgaggag gcccgcacug ccauacacuc gcugacugag agacuuuacg uaggagggcc   8460
cauguucaac agcaaggguc aaaccugcgg uuacagacgu ugccgcgcca gcggggugcu   8520
aaccacuagc augggguaaca ccaucacaug cuaugugaaa gcccuagcgg ccugcaaggc   8580
ugcggggaua guugcgccca caaugcuggu augcggcgau gaccuaguag ucaucucaga   8640
aagccagggg acugaggagg acgagcggaa ccugagagcc uucacggagg ccaugaccag   8700
guacucugcc ccuccuggug aucccccag accggaauau gaccuggagc uaauaaacauc   8760 cuguuccuca aaugugucug uggcguuggg cccgcggggc cgccgcagau acuaccugac   8820
cagagaccca accacuccac ucgcccgggc ugccugggaa acaguuagac acucccccuau   8880 caauucaugg cugggaaaca ucauccagua ugcuccaacc auaugggguuc gcauggucccu   8940 aaugacacac uucuucucca uucucauggu ccaagacacc cuggaccaga accucaacuu   9000
ugagauguau ggaucaguau acuccgugaa uccuuuggac cuuccagcca uaauugagag   9060
guuacacggg cuugacgccu uuucuaugca cacauacucu caccacgaac ugacgcgggu   9120
ggcuucagcc cucagaaaac uuggggcgcc accccucagg guguggaaga gucgggcucg   9180
cgcagucagg gcgucccuca ucucccgugg agggaaagcg gccguuugcg gccgauaucu   9240
cuucaauugg gcggugaaga ccaagcucaa acucacucca uugccggagg cgcgccuacu   9300
ggacuuaucc aguugguuca ccgucggcgc cggcgggggc gacauuuuuc acagcguguc   9360
gcgcgcccga ccccgcucau uacucuucgg ccuacuccua cuuuucguag ggguaggccu   9420
cuuccuacuc cccgcucggu agagcggcac acacuaggua cacuccauag cuaacuguuc   9480
cuuuuuuuuu uuuuuuuuuu uuuuuuuuuu uuuuuuuuuu uuuucuuuuu uuuuuuuuuc   9540
ccucuuucuu cccuucucau cuuauucuac uuucuuucuu gguggcucca ucuuagcccu   9600
agucacggcu agcugugaaa gguccgugag ccgcaugacu gcagagagug ccguaacugg   9660
ucucucugca gaucaugu                                                  9678
```

<210> SEQ ID NO 10
<211> LENGTH: 3748
<212> TYPE: DNA
<213> ORGANISM: Hepatitis C virus
<220> FEATURE:
<221> NAME/KEY: misc_feature
<222> LOCATION: (1)..(3748)
<223> OTHER INFORMATION: genomic RNA sequence comprising 5UTR to NS3 region of TH1 strain

<400> SEQUENCE: 10

```
gccagccccc gattgggggc gacactccac catagatcac tcccctgtga ggaactactg     60
tcttcacgca gaaagcgtct agccatggcg ttagtatgag tgtcgtgcag cctccaggac    120
ccccctcccc gggagagcca tagtggtctg cggaaccggt gagtacaccg gaattgccag    180
gacgaccggg tcctttcttg gatcaacccg ctcaatgcct ggagatttgg gcgtgccccc    240
gcgagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaaacgt aacaccaacc gccgcccaca ggacgtcaag ttcccgggcg    420
gtggccagat cgttggtgga gtttacctgt tgccgcgcag gggccccagg ttgggtgtgc    480
gcgcgactag gaagacttcc gagcggtcgc aacctcgtgg aaggcgacaa cctatcccca    540
```

-continued

```
aggatcgccg acccgagggc agggcctggg ctcagcccgg gtaccttgg cccctctatg    600
gcaacgaggg catgggtgg gcaggatggc tcctgtcacc ccgtggctcc cggcctagtt    660
ggggccccaa tgaccccgg cgcaggtcgc gtaatttggg taaagtcatc gatacccta     720
catgcggctt cgccgacctc atggggtaca ttccgctcgt cggcgctccc ttggggggcg   780
ctgccagggc cttggcgcat ggcgtccggg ttctggagga cggcgtgaac tatgcaacag   840
ggaatctgcc cggttgctct ttctctatct tcctcttggc tctgctgtcc tgtctaacca   900
tcccagcttc cgcttatgaa gtgcgcaacg tgtccggggt gtaccatgtc acgaacgact   960
gctccaactc gagcattgtg tacgagacag gggacatgat tatgcacacc cctgggtgcg  1020
tgccctgtgt tcgggagaac aactcctccc gctgctgggc agcgctcact cccacgctcg  1080
cggccaggaa cgccagcgtc cccaccacga caatacggcg ccacgtcgat ttgctcgttg  1140
gggcggctgc tttctgctcc gctatgtacg tgggggatct ctgcggatct gttttcctcg  1200
tctcccagtt gttcaccttc tcgcctcgcc ggcatgagac agtgcaggac tgcaattgtt  1260
caatctatcc cggccacgta tcaggtcacc gcatggcttg ggatatgatg atgaactggt  1320
cacctacaac agccctactg gtatcgcagt tactccggat cccacaagcc gtcgtggaca  1380
tggtggcggg ggcccactgg ggagtcctgg cgggccttgc ctactattcc atggcgggga  1440
actgggctaa ggttttgatt gtgctgctac tctttgccgg cgttgatggg gcgacctacg  1500
tgacgggggg gtcggaagcc agaggggcct ctggcttagc aaacctcttt tcatttgggg  1560
cgtctcagaa gatccagctc ataaatacca acggcagttg gcacatcaat agaactgccc  1620
tgaactgcaa tgactccctc cacactgggt ttcttgccgc gctattctac acacacaaat  1680
tcaacgcgtc cggatgtcca gagcgcatgg ccagctgccg ccccattgaa gagttcgctc  1740
aggggtatgg tcccatcact tatgctgagc cctcccctc ggaccagagg ccctattgct   1800
ggcactacgc gcctcgaccg tgtggtatca taccgcgtc gcaggtgtgt ggtccagtgt   1860
actgcttcac cccaagccct gttgtggtgg ggacgaccga tcgctccggt gccccacgt   1920
ataattgggg ggcgaatgag acggacgtgc tgtatctcaa caacgcgg ccgccgcaag    1980
gcaactggtt cggctgcaca tggatgaatg caccgggtt caccaagacg tgcggggcc    2040
ccccgtgcaa catcgggggg ggcggcaaca acaacaccct gacctgcccc acggactgtt  2100
tccgaaaaca ccccgaggcc acctacacca aatgtggttc gggaccttgg ttgacaccta  2160
ggtgcatggt cgactaccca tacaggctct ggcactaccc ctgcaccgtt aactttacca  2220
tctttaaggt taggatgtac gtgggaggtg tggagcacag gctcaacgcc gcatgcaatt  2280
ggaccgagg agagcgttgt aacttagagg acagggatag atcagagctt agcccgctgc   2340
tgctgtcaac aacagagtgg caggtgctac cttgttcctt caccacccta ccggctctgt  2400
ccactggttt gatccatctc caccagaaca tcgtggacgt gcaatacctg tacggtatag  2460
ggtcggcggt tgtctcctat gcaatcaaat gggaatatgt cttgttgctc ttcctcctcc  2520
tggcagacgc gcgcgtctgc gcctgcttgt ggatgatgct gctgatagct caagctgagg  2580
ccgccttaga gaacctggtg gtcctcaatg cggcgtccct ggctggagcg catggccttc  2640
tctctttcct tgtgttcttc tgtgccgctt ggtacatcaa gggcaggttg atccccgggg  2700
cggcgtatgc ttttttacgg cgtatggccgc tgctcctact cctgctggcg ttaccaccac  2760
gagcatacgc catggaccgg gagatggctg catcgtgcgg aggcgcggtt tttgtaggtc  2820
tggcattcct gaccttgtca ccacactata aggcattcct cgccaagctc atggtggt   2880
```

```
tacaatattt tatcaccaga gccgaggccc atttgcaagt gtggatcccc cccctcaacg    2940 tccgggggg ccgcgatgcc atcatcctcc tcacatgcgc gatccatcca gaccttatct    3000
ttgacatcac caaactcttg ctcgccatgc tcggtccact catggtgctc caggctggca    3060
taactagagt gccgtacttc gtgcgcgctc aagggctcat cgtgcatgc atgttggtgc    3120 ggaaagtcgc tggggtcat tatgtccaaa tggccctcat gaagctggcc tcgctgacag    3180
gtacgtacgt ttacgaccat cttactccac tgcgggactg ggcccacggg ggcctacgag    3240
accttgcggt ggcagttgag cccgtcatct tctctgacat ggagaccaaa atcatcactt    3300
ggggagcaga caccgcggcg tgtggggaca tcatctcggg tctgcccgtc tccgcccgaa    3360
gggggaggga gatatttctg gaccggccg acaagatcag agagcagggg tggcgactcc    3420
ttgcccccat cacggcctat tcccaacaga cgcgaggcct actcggctgc atcatcacta    3480
gcctcacagg ccgggacaag aaccaggtcg aggggaggt tcaagtggtc tctaccgcaa    3540
cgcaatcttt cctggcgacc tgcgtcaacg gcgtgtgttg gactgtctac catggtgccg    3600
gctcgaaaac tctagccggc ccgaagggac caatcaccca aatgtacacc aatgtagacc    3660
aggacctcgt cggctggcag gcgcccccg gggcgcgctc cttaacacca tgcacctgcg    3720
gcagctcgga cctttacttg gtcacgag                                       3748

<210> SEQ ID NO 11
<211> LENGTH: 11102
<212> TYPE: RNA
<213> ORGANISM: Homo sapiens
<220> FEATURE:
<221> NAME/KEY: misc_feature
<222> LOCATION: (1)..(11102)
<223> OTHER INFORMATION: Chimera Hepatitis C virus genomic RNA derived
      from HCV JFH1 strain(JFH-1 clone) and HCV TH strain

<400> SEQUENCE: 11 accugcccu aauagggcg acacuccgcc augaaucacu ccccugugag gaacuacugu       60
cuucacgcag aaagcgccua gccauggcgu uaguaugagu gucguacagc cuccaggccc     120 cccccuccg ggagagccau aguggucugc ggaaccggug aguacaccgg aauugccggg     180
aagacugggu ccuucuugg auaaacccac ucuaugcccg ccauuuggg cgugcccccg       240 caagacugcu agccgaguag cguugggu ug cgaaaggccu uguggu acug ccugauaggg     300 cgcuugcgag ugccccggga ggucucuag accgugcacc augagcacaa auccuaaacc      360
ucaaagaaaa accaaaagaa acaccaaccg ucgcccaaug auugaacaag auggauugca     420
cgcagguucu ccggccgcuu gguggagag gcuauucggc uaugacuggg cacaacagac      480
aaucggcugc ucugaugccc ccguguuccg gcugucagcg cagggcgcc gguucuuuu       540 ugucaagacc gaccguccg gugcccugaa ugaacgcag gacgaggcag gcggcuauc        600 guggcuggcc acgacgggcg uuccuugcgc agcugugcuc gacguuguca cugaagcggg     660
aagggacugg cugcuauugg gcgaaguccc ggggcaggau cuccugucau cucaccuugc     720
uccugccgag aaaguauccca ucauggcuga ugcaaugcgg cggcugcaua cgcuugaucc    780
ggcuaccugc ccauucgacc accaagcgaa acaucgcauc gagcgagcac guacucggau    840
ggaagccggu cuugucgauc aggaugaucu ggacgaagag caucgggc ucgcgccagc       900 cgaacuguuc gccaggcuca aggcgcgcau gcccgacggc gaggaucucg ucgugaccca     960
uggcgaugcc ugcuugccga auaucauggu ggaaaauggc cgcuuuucug gauucaucga    1020
cuguggccgg cugggugugg cggaccgcua ucaggacaua gcguuggcua cccgugauau    1080
```

```
ugcugaagag cuuggcggcg aaugggcuga ccgcuuccuc gugcuuuacg guaucgccgc    1140
ucccgauucg cagcgcaucg ccuucuaucg ccuucuugac gaguucuucu gaguuuaaac    1200
ccucucccuc cccccccccu aacguuacug gccgaagccg cuuggaauaa ggccggugug    1260
cguuugucua uauguuauuu uccaccauau ugccgucuuu uggcaaugug agggcccgga    1320
aaccuggccc ugucuucuug acgagcauuc cuaggggucu uccccucuc gccaaaggaa     1380 ugcaaggucu guugaauguc gugaaggaag caguuccucu ggaagcuucu ugaagacaaa    1440
caacgucugu agcgacccuu ugcaggcagc ggaacccccc accggcgac aggugccucu     1500 gcggccaaaa gccacgugua uaagauacac cugcaaaggc ggcacaaccc cagugccacg    1560
uugugaguug gauaguugug gaaagaguca aauggcucuc cucaagcgua uucaacaagg    1620
ggcugaagga ugcccagaag guaccccauu guagggauc ugaucugggg ccucggugca     1680
caugcuuuac augcuuuag ucgagguuaa aaaaacgucu aggcccccg aaccacgggg      1740 acgugguuuu ccuuugaaaa acacgaugau accaugagca cgaauccuaa accucaaaga    1800
aaaaccaaac guaacaccaa ccgccgccca caggacguca aguucccggg cggguggccag   1860 aucguuggug gaguuuaccu guugccgcgc agggggccca gguugggugu gcgcgcgacu    1920
aggaagacuu ccgagcgguc gcaaccucgu ggaaggcgac aaccuauccc caaggaucgc    1980
cgacccgagg gcagggccug ggcucagccc ggguacccuu ggccccucua uggcaacgag    2040
ggcauggggu gggcaggaug gcuccuguca ccccguggcu cccggccuag uuggggcccc    2100
aaugaccccc ggcgcaagguc gcguaauuug gguaaaguca ucgauacccu uacaugcggc   2160
uucgccgacc ucauggggua cauuccgcuc gucggcgcuc ccuuggggg cgcugccagg    2220 gccuuggcgc auggcguccg gguucuggag gacggcguga acuaugcaac agggaaucug    2280
cccgguugcu cuuucucuau cuccucuug gcucugcugu ccugcuaac caucccagcu     2340 uccgcuuaug aagugcgcaa cguguccggg guguaccaug ucacgaacga cugcuccaac    2400
ucgagcauug uguacgagac agggacaug auuaugcaca ccccugggug cgugcccugu     2460
guucgggaga caacuccuc ccgcugcugg gcagcgcuca cucccacgcu cgcggccagg     2520
aacgccagcg uccccaccac gacaauacgg cgccacgucg auuugcucgu uggggcggcu    2580 gcuucugcu ccgcuaugua cguggggau ucugcggau cuguuuccu cgucuccag         2640 uuguucaccu ucucgccucg ccggcaugag acagugcagg acugcaauug uucaaucuau    2700
cccggccacg uaucaggucu ccgcaugguu ugggauauga ugaugaacug gucaccuaca    2760
acagcccuac ugguaucgca guuacuccgg aucccacaag ccgucgugga cauggugccg    2820
ggggcccacu ggggaguccu ggcgggccuu gccacuauau ccauggcggg gaacugggcu    2880
aagguuuuga uugugcugcu acucuuugcc ggcuugaug ggcgaccua cgugacgggg      2940 gggucggaag ccagaggggc cucuggcuua gcaaaccucu uuucauuugg ggcgucucag    3000
aagauccagc ucauaaauac caacggcagu uggcacauca auagaacugc ccugaacugc    3060
aaugacuccc uccacacugg guucuugcc gcgcuauucu acacacacaa auucaacgcg     3120 uccggaugu cagagcgcau ggccagcugc cgccccauug aagagucgc ucagggguau      3180 ggucccauca cuuaugcuga gcccuccccc ucgaccagga gggccuauug cuggacuac     3240 gcgccucgac cguggguau cauaccgcg ucgcaggugu gguccagu guacugcuuc        3300 accccaagcc cuguugauggu ggggacgacc gaucgcuccg gugcccccac guauaauugg   3360
ggggcgaaug agacgacgu gcuguaucuc aacaacacgc ggccgccgca aggcaacugg    3420
uucggcugca caugaugaa uggcaccgg uucaccaaga cgugcggggg cccccugc       3480
```

-continued

```
aacaucgggg ggggcggcaa caacaacacc uugaccugcc ccacggacug uuccggaaa      3540
caccccgagg ccaccuacac caaauguggu ucgggaccuu gguugacacc uaggugcaug     3600
gucgacuacc cauacaggcu cuggcacuac cccugcaccg uuaacuuuac caucuuuaag    3660
guuaggaugu acguggggagg uguggagcac aggcucaacg ccgcaugcaa uuggacccga   3720
ggagagcguu guaacuuaga ggacagggau agaucagagc uuagcccgcu gcugcuguca    3780
acaacagagu ggcaggugcu accuuguucc uucaccaccc uaccggcucu guccacuggu   3840
uugauccauc uccaccagaa caucguggac gugcaauacc uguacgguau agggucggcg   3900
guugucuccu augcaaucaa augggaauau gcuuguugc cuuccuccu ccuggcagac     3960
gcgcgcgucu gcgccugcuu guggaugaug cugcugauag cucaagcuga ggccgccuua   4020
gagaaccugg uggucucaa ucgcgcgucc cuggcuggag cgcauggccu ucucucuuuc    4080
cuugguucu ucugugccgc uugguacauc aagggcaggu ugauccccgg ggcggcguau    4140
gcuuuuacg gcguauggcc gcugcuccua cuccugcugg cguuaccacc acgagcauac    4200
gccaugacg caccugugca cggacagaua ggcgugggu uguugauauu gaucacccuc     4260
uucacacuca ccccggggua uaagacccuc cucggccagu gucuggggug guuugugcuau  4320
cuccugaccc uggggggaagc caugauucag gaguggguac cacccaugca ggugcgcggc  4380
ggccgcgaug gcaucgcgug ggccgucacu auauucugcc cggguguggu guuugacauu   4440
accaaauggc uuuuggcguu gcuugggccu gcuuaccucu uaagggccgc uuugacacau   4500
gugccguacu ucgucagagc ucacgcucug auaagggugau gcgcuuuggu gaagcagcuc  4560
gcgggggggua gguauguuca gguggcgcua uuugcccuug gcagguggac uggcaccuac  4620
aucuaugacc accucacacc uaugucggac ugggccgcua gcggccugcg cgacuuagcg   4680
gucgccgugg aacccaucau cuucagccccg auggagaaga aggucaucgu cugggggagcg 4740
gagacggcug caugugggga cauucuacau ggacuucccg uguccgcccg acucggccag   4800
gagauccucc ucggcccagc ugauggcuac accccaaagg gguggaagcu ccuugcuccc   4860
aucacugcuu augcccagca aaacacgaggc cuccugggcg ccauaguggu gaguaugacg   4920
gggcgugaca ggacagaaca ggccggggaa guccaaaucc uguccacagu cucucaguccu   4980
uuccucggaa caaccaucuc gggggguuuug uggacuguuu accacggagc uggcaacaag  5040
acucuagccg gcuuacgggg uccggucacg cagaugauacu cgagucucga ggggggacuug  5100
guaggcuggc ccagcccccc uggggaccaag ucuuuggagc cgugcaagug uggagccguc   5160
gaccuauauc uggucacgcg gaacgcugau gucauccccgg cucggagacg cggggacaag   5220
cggggagcau ugcucucccc gagacccauu ucgaccuuga aggggucccuc ggggggggccg  5280
gugcucugcc cuaggggcca cgucguugggg cucuccgag cagcugugug cucucggggc    5340
guggccaaau ccaucgauuu cauccccguu gagacacucg acguuguuac aaggucuccc    5400
acuuucagug acaacagcac gccaccggcu gucccccaga ccuaucaggu cgggguacuug  5460
caugcuccaa cuggcagugg aaagagcacc aaggucccug ucgcguaugc cgcccagggg   5520
uacaaaguac uagugcuuaa ccccucggua gcugccaccc uggggguugg ggcguaccua   5580
uccaaggcac auggcaucaa ucccaacauu aggacuggag ucaggaccgu gaugaccggg   5640
gaggccauca cguacuccac auauggcaaa uuucucgccg augggggcug cgcuagcggc   5700
gccuaugaca ucaucauaug cgaugaaugc cacgcgugugg augcuaccuc cauucucggc   5760
aucggaacgg uccuugauca agcagagaca gccggggguca gacuaacugu gcuggcuacg   5820
```

```
gccacacccc ccgggucagu gacaaccccc caucccgaua uagaagaggu aggccucggg   5880
cgggagggug agauccccuu cuauggaggg gcgauucccc uauccugcau caagggaggg   5940
agacaccuga uuuucugcca cucaaagaaa aagugugacg agcucgcggc ggcccuucgg   6000
ggcaugggcu ugaaugccgu ggcauacuau agagggguugg acgucuccau aauaccagcu   6060
cagggagaug uggguggucgu cgccaccgac gcccucauga cggggguacac uggagacuuu   6120 gacuccguga ucgacugcaa uguagcgguc acccaagcug ucgacuucag ccuggaccccc   6180 accuucacua uaaccacaca gacugcccca caagacgcug ucucacgcag ucagcgccgc   6240
gggcgcacag guagaggaag acagggcacu uauagguaug uuuccacugg ugaacgagcc   6300
ucaggaaugu uugacagugu agugcuuugu gagugcuacg acgcaggggc ugcgugguac   6360
gaucucacac cagcggagac caccgucagg cuuagagcgu auuucaacac gcccggccua   6420
cccguguguc aagaccaucu ugaauuuugg gaggcaguuu ucaccggccu cacacacaua   6480
gacgcccacu uccucuccca aacaaagcaa gcggggaga acuucgcgua ccuaguagcc   6540
uaccaagcua cggugugcgc cagagccaag gccccucccc cguccuggga cgccaugugg   6600
aagugccugg cccgacucaa gccuacgcuu gcgggcccca caccucuccu guaccguuug   6660
ggcccuauua ccaaugaggu caccucaca caccccggga cgaaguacau cgccacaugc   6720
augcaagcug accuugaggu caugaccagc acgggguccc uagcuggagg aguccuggca   6780
gccgucgccg cauauugccu ggcgacugga ugcguuucca ucucggccg cuugcacguc   6840 aaccagcgag ucgucguugc gccggauaag gagguccugu augaggcuuu ugaugagaug   6900
gaggaaugcg ccucuaggggc ggcucucauc gaagagggggc agcggauagc cgagauguug   6960 aguccaaga uccaaggcuu gcugcagcag gccucuaagc aggcccagga cauacaaccc   7020
gcuaugcagg cuucauggcc caaaguggaa caauuuggggg ccagacacau guggaacuuc   7080
auuagcggca uccaauaccu cgcaggauug ucaacacugc cagggaaccc cgcgguggcu   7140
uccaugaugg cauucagugc cgcccucacc aguccguugu cgaccaguac caccauccuu   7200
cucaacauca ugggaggcug guuagcgucc cagaucgcac caccccgcggg ggccaccggc   7260 uuugucguca guggccuggu gggggcugcc gugggcagca uaggccuggg uaaggugcug   7320
guggacaucc uggcaggaua uggugcgggc auuucgggggg cccucgucgc auucaagauc   7380
augucuggcg agaagccccuc uauggaagau gucaucaauc uacugccugg gauccugucu   7440
ccgggagccc ugguggugggg ggucaucugc gcggccauuc ugcgccgcca cgugggaccg   7500
ggggagggcg cgguccaaug gaugaacagg cuuauugccu uugcuuccag aggaaaccac   7560 gucgcccccua cucacuacgu gacggagucg gaugcgucgc agcgugugac ccaacuacuu   7620
ggcucucuua cuauaaccag ccuacucaga agacuccaca auuggauaac ugaggacugc   7680
cccaucccau gcuccggauc cuggcuccgc gacgugggg acuggguuug caccaucuug   7740
acagacuuca aaaauggcu gaccucuaaa uguuucccca gcugccggg ccucccuuc   7800 aucucuuguc aaaaggggua caaggggugu gggccggca cuggcaucau gaccacgcgc   7860
ugcccuugcg gcgccaacau cucuggcaau guccgccugg gcuucuagag gaucacaggg   7920
ccuaaaaccu gcaugaacac cugguagggg accuuuccua ucaauugcua acgaggggc   7980 cagugcgcgc cgaaaccccc cacgaacuac aagaccgcca ucuggagggu ggcggccucg   8040
gaguacgcgg aggugacgca gcaugggucu acuccuaug uaacaggacu gaccacugac   8100
aaucugaaaa uuccuugcca acuaccuucu ccagaguuuu ucuccggguu ggacgggugu   8160
cagauccaua gguuugcacc cacaccaaag ccguuuuucc gggaugaggu cucguucgc   8220
```

-continued

```
guugggcuua auccuaugc ugucggguccc cagcuucccu gugaaccuga gcccgacgca   8280
gacguauuga gguccaugcu aacagauccg ccccacauca cggcggagac ucggcgcgg    8340
cgcuuggcac ggggaucacc uccaucugag gcgagcuccu cagugagcca gcuaucagca   8400
ccgucgcugc gggccaccug caccaccac agcaacaccu ugacgugga cauggucgau    8460
gccaaccugc ucauggaggg cggugugcu cagacagagc ugaguccag ggugcccguu    8520
cuggacuuuc ucgagccaau ggccgaggaa gagagcgacc uugagcccuc aauaccaucg   8580
gagugcaugc ucccccaggag cgggguucca cgggccuuac cggcuggggc acggccugac  8640
uacaacccgc cgcucgugga aucguggagg aggccagauu accaaccgcc caccguugcu   8700
gguugugcuc uccccccccc aagaaggcc ccgacgccuc cccaaggag acgccggaca    8760
gugggucuga gcgagagcac cauaucagaa gccucccagc aacuggccau caagaccuuu   8820
ggccagcccc ccucgagcgg ugaugcaggc ucguccacgg gggcgggcgc cgccgaaucc   8880
ggcgguccga cguccccugg ugagccggcc cccucagaga caggguccgc cuccucuaug   8940
cccccccucg aggggggagcc uggagauccg gaccuggagu cugaucaggu agagcuucaa  9000
ccucccccccc agggggggggg gguagcuccc gguucgggcu cgggggucuug gucuacuugc  9060
uccgaggagg acgauaccac cgugugcugc uccaugucau acuccuggac cggggcucua   9120
auaacucccu guagcccga agaggaaaag uugccaauca acccuuugag uaacucgcug    9180
uugcgauacc auaacaaggu guacuguaca acaucaaaga gcgccucaca gagggcuaaa   9240
aagguaacuu uugacaggac gcaagugcuc gacgccauu augacucagu cuuaaaggac     9300
aucaagcuag cggcuuccaa ggucagcgca aggcuccuca ccuuggagga ggcgugccag    9360
uugacuccac cccauucugc aagauccaag uauggauucg gggccaagga ggucgcgagc    9420
uuguccggga gggccguuaa ccacaucaag uccgugugga aggaccuccu ggaagaccca    9480
caaacaccaa uucccacaac caucauggcc aaaaaugagg uguucugcgu ggaccccgcc    9540
aaggggggua agaaaccagc ucgccucauc guuuacccug accucggcgu ccggucucgc    9600
gagaaaaugg cccucuauga cauuacacaa aagcuuccuc aggcgguaau gggagcuucc    9660
uauggcuucc aguacucccc ugcccaacgg guggaguauc ucuugaaagc augggcggaa    9720
aagaaggacc ccaugggguuu uucguaugau acccgaugcu ucgacucaac cgucacugag    9780
agagacauca ggaccgagga guccauauac caggccugcu cccugcccga ggaggcccgc    9840
acugccauac acucgcugac ugagagacuu uacguaggag ggcccauguu caacagcaag    9900
ggucaaaccu gccguuacag acguugccgc gccagcgggg ugcuaaccac uagcaugggu    9960
aacaccauca caugcuaugu gaaagcccua gcggccugca aggcugcggg gauaguugcg   10020
cccacaaugc ugguaugcgg cgaugaccua guaucaucu cagaaagcca ggggacgag    10080
gaggacgagc ggaaccugag agccuucacg gaggccauga ccagguacuc ugcccccccu    10140
ggugauccccc ccagaccgga auaugaccug gagcuaauaa cauccuguuc ucaaaaugug    10200
ucuguggcgu ugggcccgcg gggccgccgc agauacuacc ugaccagaga cccaaccacu    10260
ccacucgccc gggcugccug gaaaacaguu agacacuccc cuaucaauuc auggcuggga    10320
aacaucaucc aguaugcucc aaccauaugg guucgcaugg uccuaaugac acacuucuuc    10380
uccauucuca uggucaaaga cacccuggac cagaaccuca acuuugagau guauggauca    10440
guauacccg ugaauccuuu ggaccuucca gccauaauug agagguuaca cgggcuugac    10500
gccuuuucua ugcacacaua cucucaccac gaacugacgc ggguggcuuc agcccucaga   10560
```

-continued

| | |
|---|---|
| aaacuugggg cgccaccccu cagggugugg aagagucggg cucgcgcagu cagggcgucc | 10620 |
| cucaucuccc guggagggaa agcggccguu ugcggccgau aucucuucaa uugggcggug | 10680 |
| aagaccaagc ucaaacucac uccauugccg gaggcgcgcc uacuggacuu auccaguugg | 10740 |
| uucaccgucg gcgccggcgg gggcgacauu uuucacagcg ugucgcgcgc ccgaccccgc | 10800 |
| ucauuacucu ucggccuacu ccuacuuuuc guaggggguag gccucuuccu acuccccgcu | 10860 |
| cgguagagcg gcacacacua gguacacucc auagcuaacu guuccuuuuu uuuuuuuuuu | 10920 |
| uuuuuuuuuu uuuuuuuuuu uuuuuuuucu uuuuuuuuuu uuucccucuu ucuucccuuc | 10980 |
| ucaucuuauu cuacuuucuu ucuuggguggc uccaucuuag cccuagucac ggcuagcugu | 11040 |
| gaaagguccg ugagccgcau gacugcagag agugccguaa cuggucucuc ugcagaucau | 11100 |
| gu | 11102 |

The invention claimed is:

1. A modified hepatitis C virus genomic RNA comprising genomic RNA portions of two or more strains of hepatitis C viruses, which comprises a 5' untranslated region, a core protein coding sequence, an E1 protein coding sequence, an E2 protein coding sequence, a p7 protein coding sequence, an NS2 protein coding sequence, a partial RNA sequence encoding NS3, NS4A, NS4B, NS5A, and NS5B proteins of a JFH1 strain shown in SEQ ID NO:1, and a 3' untranslated region, wherein said modified hepatitis C virus genomic RNA is autonomously replicated and is capable of producing infectious hepatitis C virus particles in a cultured cell system, wherein the core protein coding sequence, the E1 protein coding sequence, the E2 protein coding sequence, and the p7 protein coding sequence are from the hepatitis C virus strain of genotype 1b, wherein the NS2 protein coding sequence is from the hepatitis C virus strain selected from the group consisting of genotype 1b and genotype 2a, and wherein the 5' untranslated region and the 3' untranslated region are from the JFH-1 strain, wherein the hepatitis C virus strain of genotype 1b is HCV-con 1 strain.

2. The modified hepatitis C virus genomic RNA according to claim 1, wherein the core protein coding sequence, the E1 protein coding sequence, the E2 protein coding sequence, the p7 protein coding sequence are from the HCV-con1 strain of genotype 1b, and the NS2 protein coding sequence is from an HCV-con1 strain of genotype 1b.

3. A hepatic cell-directed virus vector, which comprises the modified hepatitis C virus genomic RNA according to claim 1.

4. An isolated cell comprising the modified hepatitis C virus genomic RNA according to claim 1, wherein the hepatitis C virus genomic RNA is replicated and wherein the cell generates virus particles.

5. The isolated cell according to claim 4, wherein the cell is selected from the group consisting of a Huh-7 cell, a HepG2 cell, an IMY-N9 cell, a HeLa cell, and a 293 cell.

6. An isolated hepatitis C virus particle, which is obtained from a culture obtained by culturing the cell according to claim 4.

7. An immunogenic hepatitis C virus composition comprising the hepatitis C virus particle according to claim 6 as an antigen.

8. An isolated hepatitis C virus-infected cell, which is infected with the hepatitis C virus particle according to claim 6.

9. A method for producing hepatitis C virus particles, comprising culturing the cell according to claim 4 or 8 and recovering virus particles from the culture.

10. A method for producing a hepatitis C virus-infected cell, comprising culturing the cell according to claim 4 and infecting another cell with virus particles contained in the culture.

11. A method for screening an anti-hepatitis C virus substance, comprising culturing the cell according to claim 4 in the presence of a test substance and detecting hepatitis C virus RNA or virus particles in the culture, to evaluate the effects of the anti-hepatitis C virus test substance.

12. A method for screening an anti-hepatitis C virus substance, comprising culturing the cell according to claim 8 in the presence of a test substance and detecting hepatitis C virus RNA or virus particles in the culture, to evaluate the effects of the anti-hepatitis C virus test substance.

* * * * *